(12) United States Patent
Pausch

(10) Patent No.: US 7,115,724 B2
(45) Date of Patent: Oct. 3, 2006

(54) MURINE GENOMIC POLYNUCLEOTIDE SEQUENCE ENCODING A G-PROTEIN COUPLED RECEPTOR AND METHODS OF USE THEREFOR

(75) Inventor: Mark H. Pausch, Rocky Hill, NJ (US)

(73) Assignee: Wyeth, Madison, NJ (US)

( * ) Notice: Subject to any disclaimer, the term of this patent is extended or adjusted under 35 U.S.C. 154(b) by 534 days.

(21) Appl. No.: 10/208,483

(22) Filed: Jul. 30, 2002

(65) Prior Publication Data

US 2006/0075510 A1 Apr. 6, 2006

Related U.S. Application Data

(60) Provisional application No. 60/314,068, filed on Aug. 22, 2001.

(51) Int. Cl.
C07H 21/02 (2006.01)
C07H 21/04 (2006.01)
C12N 5/00 (2006.01)

(52) U.S. Cl. .................. 536/23.1; 536/23.5; 435/325

(58) Field of Classification Search .............. 536/23.1, 536/23.4, 23.5, 24.1, 24.31, 24.5; 435/325, 435/252.1
See application file for complete search history.

(56) References Cited

U.S. PATENT DOCUMENTS 6,060,272 A * 5/2000 Li et al. .................. 435/69.1

OTHER PUBLICATIONS

Adachi, J., et al., "Functional annotation of a full-length mouse cDNA collection", *Nature* 409, 865-690, 2001.
Boeynaems et al., "P2Y receptors: in the middle of the road," *TIPS* 21, 1-3, 2000.
Boyer et al., "Identification of a P2Y-purinergic receptor that inhibits adenylyl cyclase," *J Pharmacol Exp Ther.* 267, 1140-1146, 1993.
Cattaneo et al., "Identification of a new congenital defect of platelet function characterized by severe impairment of platelet responses to adenosine diphosphate," *Blood* 80, 2787-2796, 1992.
Chambers et al., "A G protein-coupled receptor for UDP-glucose ," *J. Biol. Chem.* 275, 10767-71, 2000.
Chen and Chen, ATP-induced arachadonic acid release in cultured astrocytes is mediated by Gi protein coupled P2Y1 and P2Y2 receptors, *Glia* 22, 360-370, 1998.
Harder et al, "P2-purinergic receptors," *Annu. Rev. Pharmacol. Toxicol.* 35, 541-579, 1995.
Hoffmann et al., "The role of amino acids in extracellular loops of the human P2Y1 receptor in surface expression and activation processes," *J Biol Chem.* 274, 14639-47, 1999.
Hollopeter et al., "Identification of the platelet ADP receptor targeted by antithrombotic drugs," *Nature* 409, 202-207, 2001.

Jacobs et al., "A genetic selection for isolating cDNAs encoding secreted proteins," *Gene* 198, 289-296, 1997.
Jantzen et al., "Evidence for two distinct G-protein-coupled ADP receptors mediating platelet activation," *Thromb Haemost* 81, 111-117, 1999.
Jiang et al., "A mutational analysis of residues essential for ligand recognition at the human P2Y1 receptor," *Mol Pharmacol.* 52, 499-507, 1997.
Kunapuli, "Multiple P2 receptor subtypes on platelets: a new interpretation of their function," *TIPS 19*, 391-394, 1998.
Mumberg et al., "Yeast vectors for the controlled expression of heterologous proteins in different genetic backgrounds," *Gene 156*, 119-122, 1995.
Nurden et al., "An inherited bleeding disorder linked to a defective interaction between ADP and its receptor on platelets," *J. Clin. Invest.* 95, 1612-1622, 1995.
Pausch et al., Heterologous G Protein-Coupled Receptors Expressed in *Saccharomyces cerevisiae*: Methods for Genetic Analysis and Ligand Identification. *In* "Identification and Expression of G Protein-Coupled Receptors." (Ed, L, R. Lynch) "Receptor Biochemistry and Methodology" (Series Eds. Sibley, D. and Strader, C.), pp. 196-212, Wiley, Inc., 1998.
Pausch, "GPCRs in *Saccharomyces cerevisiae*: HTS assays for drug discovery," *TIB 15*, 48-494, 1997.
Robinson and Dowd, "Heterogeneity and functional properties of subtypes of sodium-dependent glutamate transporters in the mammalian central nervous system," *Adv. Pharmacology 37*, 69-115, 1997.
Webb et al., "The P2Y purinoceptor in rat brain microvascular endothelial cells couple to inhibition of adenylate cyclase," *Br. J. Pharmacol. 119*, 1385-1392, 1996.
Zhang et al., "ADP is the cognate ligand for the orphan G protein-coupled receptor SP1999," *J. Biol. Chem.*, 276:8608-8615, 2001.
Leon, C. et al. Defective Platelet Aggregation and Increased Resistance to Thrombosis in Purinergic P2YI Receptor-Null Mice, *Journal of Clinical Investigation*. Dec. 1999, vol. 104, No. 12, pp. 1731-1737.
Enjyoji, K. et al. Targeted Disruption of cd39/ATP Diphosphorylase Results in Disordered Hemostatsis and Thromboregulation. *Nature Medicine*. Sep. 1999, vol. 5, No. 9, pp. 1010-1017.

(Continued)

*Primary Examiner*—Joseph Woitach
(74) *Attorney, Agent, or Firm*—Teresa O. Bittendender; Wyeth

(57) ABSTRACT

The present invention particularly relates to a newly identified murine genomic polynucleotide that encodes an ortholog of the human P2T receptor which is expressed at high levels in the central nervous system, the use of such polynucleotides and polypeptides, as well as the production of such polynucleotides and polypeptides. The invention relates also to identifying compounds which may be agonists, antagonists and/or inhibitors of P2T, and therefore potentially useful in therapy.

11 Claims, 4 Drawing Sheets

OTHER PUBLICATIONS

Leon, C. et al. The P2Y1 Receptor is Normal in a Patient Presenting a Severe Deficiency of ADP-Induced Platelet Aggregation. *Thrombosis and Hemostasis*. 1999. vol. 81, No. 5, pp. 775-781.

Sun, B. et al. P2X1 Purinoceptor in Human Platelets. *Journal of Biological Chemistry*. May 8, 1998, vol. 273, No. 19, pp. 11544-11547.

Jin, J. et al. Molecular Basis for ADP-Induced Platelet Aggregation. *Journal of Biological Chemistry*. Jan. 23, 1998, vol. 273, No. 4, pp. 2030-2034.

Cattaneo, M. et al. ADP Receptors and Clinical Bleeding Disorders. *Arterosclerosis Thrombosis and Vascular Biology*. Oct. 1999. vol. 19, pp. 2281-2285.

* cited by examiner

```
              _____TM1_____
mP2T    M?VPG?N??TSANTT?S?PGTSTLC?RDYKITQVLFPLLYTVLFFAGLITNSLAMRIFFQIR  60
rP2T    M?VPG???TSANTTS?PGTSTLCSRDYKITQVLFPLLYTVLFFAGLITNSLAMRIFFQIR    60
hP2T    ------M?A?D?N?TS?PG?T?SLC?RDYKITQVLFPLLYTVLFF?GLITN?LAMRIFFQIR   54

_____TM2_____                          _____TM3_____
mP2T    SKSNFIIFLKNTVISDLLMILTFPFKILSDAKLGAGPLRTLVCQVTSVTFYFTMYISISF   120
rP2T    SKSNFIIFLKNTVISDLLMILTFPFKILSDAKLGAG?LRTLVCQVTSVTFYFTMYISISF   120
hP2T    SKSNFIIFLKNTVISDLLMILTFPFKILSDAKLG?GPLRTFVCQVTSV?FYFTMYISISF   114

_____TM4_____
mP2T    LGLITIDRYLKTTRPFKTSSPSNLLGAKILSVVIWAFMFL?SLPNMILTNRRPKDKDVTK   180
rP2T    LGLITIDRYLKTTRPFKTSSPSNLLGAKILSV?IWAFMFLLSLPNMILTNRRPKDKD?TK   180
hP2T    LGLITIDRY?KTTRPFKTSN?PKNLLGAKILSVVIWAFMFLLSLPNMILTNR?P?DK?VKK  174

_____TM5_____
mP2T    CSFLKSEFGLVWHEIVNYICQVIFWINFLIVIVCYSLITKELYRSYVRTRGSAKVPKKKV   240
rP2T    CSFLKSEFGLVWHEIVNYICQVIFWINFLIVIVCYSLITKELYRSYVRTRGSAK?PKK?V   240
hP2T    CSFLKSEFGLVWHEIVNYICQVIFWINFLIVIVCY?LITKELYRSYVRTRG?GKVP?KKV   234

_____TM6_____                      _____TM7_____
mP2T    NVKVFIIIAVFFICFVPFHFARIPYTLSQTRAVFDC?AENTLFYVKESTLWLTSLNACLD   300
rP2T    N?KVFIIIAVFFICFVPFHFARIPYTLSQTRAVFDC?AENTLFYVKESTLWLTSLNACLD   300
hP2T    NVKVFIIIAVFFICFVPFHFARIPYTLSQTR?VFDC?AENTLFYVKESTLWLTSLNACLD   294 mP2T    PFIYFFLCKSFRNSL?SMLRCSN-STSTSG?NKKKGQEGG?PSEETPM                347
rP2T    PFIYFFLCKSFRNSLMSMLRCS-----TSG?NKKKGQEGGDPSEETPM                343
hP2T    PFIYFFLCKSFRNSL?SML?C?NSATS?S??NRKK?Q?GGDP?EETPM                342
```

MURINE GENOMIC POLYNUCLEOTIDE SEQUENCE ENCODING A G-PROTEIN COUPLED RECEPTOR AND METHODS OF USE THEREFOR

This application claims priority from a provisional application Ser. No. 60/314,068, filed on Aug. 22, 2001, the entire disclosure of which is hereby incorporated by reference.

FIELD OF THE INVENTION

The present invention relates generally to the fields of neuroscience, cell signaling and molecular biology. More particularly, the invention relates to a newly identified murine genomic polynucleotide that encodes an ortholog of the human P2T receptor which is expressed at high levels in the central nervous system, the use of such polynucleotides and polypeptides, as well as the production of such polynucleotides and polypeptides. The invention relates also to identifying compounds which may be agonists, antagonists and/or inhibitors of P2T, and therefore potentially useful in therapy.

BACKGROUND OF THE INVENTION

Platelets play a central role in blood clot formation critical to the maintenance of normal homeostasis (Harder et al., 1995). Pathological thrombus formation producing vascular occlusion can result in stroke, myocardial infarction and unstable angina. Platelet aggregation and shape change are induced by ADP released from damaged vessels and red blood cells. ADP also is secreted by platelets from dense granules on activation, potentiating the aggregation response induced by other agents. Three types of purinergic receptors mediate the platelet response to ADP: P2X, an ADP-gated ion channel and two types of G-protein coupled receptors: P2Y1, coupled to increases in intracellular calcium via Gq, and P2T ($P2Y_{ADP}$, $P2Y_{AC}$, $P2Y_{cyc}$, $P2T_{AC}$), an ADP receptor coupled to inhibition of adenylyl cyclase through Gi (Ralevic and Burnstock, 1998; Kunapuli, 1998; Jantzen et al., 1999; Boeynaerns et al., 2000). Interestingly, the P2T receptor is irreversibly inactivated by active metabolites of the anti-clotting drugs, ticlopidine and clopidogrel (Savi et al., 2000); and patients with a rare heritable clotting disorder lack P2T receptors (Catteneo et al., 1992; Nurden et al., 1995).

In addition, the P2T receptor may have a role in the central nervous system (CNS). ADP receptors with pharmacological properties similar to the platelet P2T receptor have been identified in B10 brain endothelial cells and rat C6 glioma cells (Webb et al., 1996; Boyer et al., 1993). Until recently however, the P2T G-protein-coupled receptor had remained uncloned (Zhang et al., 2001; Hollopeter et al., 2001).

In the CNS, nucleotides and related compounds are often released in concert with other neurotransmitters and act as signal transduction modulators. It has been reported that treatment of astrocytes with P2T selective agonists produces an increase in arachidonic acid release via a pertussis toxin sensitive G-protein-dependent mechanism (Chen and Chen, 1998). ADP-induced arachidonic acid release from astrocytes stimulates glycogenolysis, suggesting that the ADP receptor may be involved in regulation of glycogen metabolism in the CNS. Arachidonic acid acts directly on glial glutamate transporters to inhibit uptake of glutamate (Robinson and Dowd, 1997), further suggesting that glial ADP receptors may regulate neurotransmitter re-uptake. However, the exact role played by the P2T G-protein-coupled receptor in the CNS is not well understood.

It is well established that many medically significant biological processes are mediated by polypeptides participating in cellular signal transduction pathways that involve G proteins and second messengers, e.g., cAMP, $IP_3$ and diacylglycerol (Lefkowitz, 1991). Some examples of these polypeptides include G-proteins and G-protein-coupled receptors themselves (e.g., G-protein-coupled receptor families I, II, III and IV), G-protein-coupled receptors such as those for biogenic amine transmitters (e.g., epinephrine, norepinephrine and dopamine) (Kobilka et al., 1987(a); Kobilka et al., 1987(b); Bunzow et al., 1988), effector polypeptides (e.g., phospholipase C, adenyl cyclase and phosphodiesterase) and actuator polypeptides (e.g., polypeptide kinase A and polypeptide kinase C) (Simon et al., 1991).

One particular pathway of cellular signal transduction is the inositol phospholipid pathway. In this pathway, an extracellular signal molecule (e.g., epinephrine) binds to a G-protein-coupled receptor. The G-protein-coupled receptor (GPCR) subsequently associates with a specific trimeric G-protein, wherein the trimer is comprised of α, β and γ polypeptide subunits. In the GPCR/G-polypeptide associated state, there is an exchange of GDP for GTP at the G-polypeptide α-subunit, resulting in the dissociation of the α-subunit from the β/γ subunits. The GTP bound α-subunit is the active state of the polypeptide. The active α-subunit further activates phospholipase C, which catalyzes the cleavage of $PIP_2$ to $IP_3$ and diacylglycerol (DAG). The $IP_3$ and DAG serve as second messengers in further signal amplification (e.g., $Ca^{2+}$ release and phosphorylation). Hydrolysis of GTP to GDP, catalyzed by the G-protein itself, returns the G-protein to its basal, inactive form. Thus, following GPCR binding a ligand molecule, the ligand activates a G-protein. The G-protein serves a dual role, as an intermediate that relays the signal from receptor to effector, and as a clock that controls the duration of the signal.

GPCRs are membrane bound polypeptides, comprising a gene superfamily characterized as having seven putative transmembrane domains. GPCRs can be intracellularly coupled by heterotrimeric G-proteins to various intracellular enzymes, ion channels and transporters (see, Johnson et al., 1989). Different G-protein α-subunits preferentially stimulate particular effectors to modulate various biological functions in a cell.

The G-protein-coupled receptors include a wide range of biologically active receptors, such as hormone receptors, viral receptors, growth factor receptors and neuroreceptors. Examples of members of this family include, but are not limited to, dopamine, calcitonin, adrenergic, endothelin, cAMP, adenosine, muscarinic acetylcholine, serotonin, histamine, thrombin, kinin, follicle stimulating hormone, opsins, endothelial differentiation gene-1, rhodopsins, odorant, and cytomegalovirus receptors.

The seven transmembrane domains are believed to represent transmembrane α-helices connected by extracellular or cytoplasmic loops. GPCRs have been characterized as including these seven conserved hydrophobic stretches of about 20 to 30 amino acids, connecting at least eight divergent hydrophilic loops. Most GPCRs (also known as 7TM receptors) have single conserved cysteine residues in each of the first two extracellular loops which form disulfide bonds that are believed to stabilize functional polypeptide structure. The 7 transmembrane regions are designated as TM1, TM2, TM3, TM4, TM5, TM6, and TM7. TM3 has been implicated in several GPCRs as having a ligand binding site, such as the TM3 aspartate residue. TM5 serines, a TM6 asparagine and TM6 or TM7 phenylalanines or tyrosines are also implicated in ligand binding in certain receptor families.

Phosphorylation and lipidation (palmitylation or farnesylation) of cysteine residues can influence signal transduction of some GPCRs. Most GPCRs contain potential phosphorylation sites within the third cytoplasmic loop and/or the carboxy terminus. For several GPCRs, such as the β-adrenoreceptor, phosphorylation by polypeptide kinase A and/or specific receptor kinases mediates receptor desensitization.

Presently, more than 800 GPCRs from various eukaryotic species have been cloned, 140 of which are human GPCRs for which endogenous ligands are known (Stadel et al., 1997). In addition, several hundred therapeutic agents targeting GPCRs such as angiotensin receptors, calcitonin receptors, adrenoceptor receptors, serotonin receptors, leukotriene receptors, oxytocin receptors, prostaglandin receptors, dopamine receptors, histamine receptors, muscarinic acetylcholine receptors, opioid receptors, somatostatin receptors and vasopressin receptors have been successfully introduced onto the market for various indications (see Stadel et al., 1997). This indicates that these receptors have an established, proven history as therapeutic targets. The search for GPCR genes has also identified numerous genes whose products are members of the GPCR family, but for which their natural ligands are not known, commonly refered to as orphan receptors. In fact, more than 100 of the 240 human GPCRs identified (i.e., about 45%) are orphan receptors, and it is estimated that there are at least 400–1000 more GPCR genes that have yet to be identified (Stadel et al., 1997).

Thus, there is clearly a need for the identification and characterization of further GPCRs, their genes and their ligands, which can play a role in preventing, ameliorating or correcting dysfunctions or diseases, including, but not limited to, infections such as bacterial, fungal, protozoan and viral infections, particularly infections caused by HIV-1 or HIV-2; pain; cancers; anorexia; bulimia; asthma; Parkinson's disease; acute heart failure; hypotension; hypertension; platelet formation and aggregation; stroke; urinary retention; osteoporosis; angina pectoris; myocardial infarction; ulcers; asthma; allergies; benign prostatic hypertrophy; and psychotic and neurological disorders, including anxiety, schizophrenia, manic depression, delirium, dementia, severe mental retardation and dyskinesias, such as Huntington's disease or Gilles dela Tourett's syndrome.

SUMMARY OF THE INVENTION

The present invention relates to a newly identified murine genomic polynucleotide that encodes an ortholog of the human P2T receptor which is expressed at high levels in the central nervous system, the use of such polynucleotides and polypeptides, as well as the production of such polynucleotides and polypeptides. The invention relates also to identifying compounds which may be agonists, antagonists and/or inhibitors of P2T, and therefore potentially useful in therapy.

In particular embodiments, the invention is directed to an isolated murine genomic polynucleotide comprising the nucleic acid sequence of SEQ ID NO:1. In other embodiments, the isolated polynucleotide is selected from the group consisting of DNA, cDNA, RNA, antisense RNA and pre-mRNA. In yet other embodiments, the polynucleotide further comprises heterologous polynucleotides.

In another embodiment, the invention is directed to an isolated murine genomic polynucleotide comprising a nucleic acid sequence of SEQ ID NO:1 encoding a P2T receptor polypeptide comprising an amino acid sequence of SEQ ID NO:2. In a preferred embodiment, the polynucleotide encoding the polypeptide sequence of SEQ ID NO:2 is active in glial cells or platelet cells. In another embodiment, the polynucleotide is selected from the group consisting of DNA, cDNA, RNA, antisense RNA and pre-mRNA and may further comprise a polynucleotide encoding a heterologous polypeptide.

In yet another embodiment, the invention is directed to an isolated polynucleotide which hybridizes to a polynucleotide comprising the nucleic acid sequence of SEQ ID NO:1 or the complement of SEQ ID NO:1, under stringent hybridization conditions. In a particular embodiment, the polynucleotide hybridizes to the nucleic acid sequence comprised within nucleotide 1 to about nucleotide 45,167 of nucleic acid sequence SEQ ID NO:1 or the complement of SEQ ID NO:1. In another embodiment, the polynucleotide hybridizes to the nucleic acid sequence comprised within nucleotide 45,168 to about nucleotide 46,358 of nucleic acid sequence SEQ ID NO:1 or the complement of SEQ ID NO:1.

In certain other embodiments, the invention provides a recombinant expression vector comprising a polynucleotide encoding a murine P2T receptor polypeptide, wherein the polynucleotide comprises the nucleic acid sequence of SEQ ID NO:1 or a degenerate variant thereof. In a particular embodiment, the polynucleotide is selected from the group consisting of DNA, cDNA, RNA, pre-mRNA and antisense RNA. In another embodiment, the vector DNA is selected from the group consisting of plasmid, episomal, YAC and viral. In a preferred embodiment, the vector is a yeast expression plasmid. In another embodiment, the vector polynucleotide is operatively linked to one or more regulatory elements selected from the group consisting of a promoter, an enhancer, a splicing signal, a termination signal, a ribosomal binding signal and a polyadenylation signal.

In yet another embodiment, the invention is directed to a genetically engineered host cell, transfected, transformed or infected with a recombinant expression vector comprising a polynucleotide encoding a murine P2T receptor polypeptide, wherein the polynucleotide comprises the nucleic acid sequence of SEQ ID NO:1 or a degenerate variant thereof. In one preferred embodiment, the host cell is eukaryotic, wherein the eukaryotic cell is further selected from the group consisting of yeast, mammal, insect and plant. In yet another preferred embodiment, the host cell is prokaryotic. In still another embodiment, the polynucleotide is expressed to produce the encoded polypeptide, a biological equivalent thereof, or a fragment thereof.

In one particular embodiment the invention is directed to an antibody specific for a murine P2T receptor polypeptide comprising the amino acid sequence of SEQ ID NO:2. In a preferred embodiment, the antibody is selected from the group consisting of monoclonal, polyclonal, chimeric, humanized and single chain. In a more preferred embodiment, the antibody is monoclonal. In another preferred embodiment, the antibody is humanized.

In another particular embodiment the invention provides an antibody specific for a polynucleotide comprising the nucleic acid sequence of SEQ ID NO:1 or a degenerate variant thereof. In a preferred embodiment, the antibody binds to a nucleic acid sequence comprised within nucleotide 1 to about nucleotide 45,167 of nucleic acid sequence SEQ ID NO:1 or the complement of SEQ ID NO:1. In another embodiment, the antibody binds to a nucleic acid sequence comprised within nucleotide 45,168 to about nucleotide 46,358 of nucleic acid sequence SEQ ID NO:1 or the complement of SEQ ID NO:1. In another preferred embodiment, the antibody is selected from the group consisting of monoclonal, polyclonal, chimeric, humanized and single chain. In a more preferred embodiment, the antibody is monoclonal.

In still another embodiment, the invention is directed to a transgenic animal comprising a polynucleotide comprising the nucleic acid sequence of SEQ ID NO:1. In one preferred embodiment, the transgenic animal comprises a mutation which modulates P2T receptor activity. In a more preferred embodiment, the P2T receptor activity is in a glial cell. In another embodiment, the polynucleotide has at least one mutation selected from the group consisting of nucleotide deletion, nucleotide substitution and nucleotide insertion. In one preferred embodiment, the transgenic animal is heterozygous for the mutation. In yet another preferred embodiment, the transgenic animal is homozygous for the mutation. In still another embodiment, the animal is selected from the group consisting of mouse, rat, rabbit and hamster.

In one particular embodiment, the invention is directed to an RNA molecule which is antisense to a polynucleotide comprising the nucleic acid sequence of SEQ ID NO:1 or a degenerate variant thereof. In one preferred embodiment, the RNA is antisense to the polynucleotide of SEQ ID NO:1 from about nucleotide 1 to about nucleotide 45,167. In another preferred embodiment, the RNA is antisense from about nucleotide 987 to about nucleotide 1,046 of SEQ ID NO:1. In yet another preferred embodiment, the RNA is antisense from about nucleotide 35,843 to about nucleotide 35,976 of SEQ ID NO:1. In still another preferred embodiment, the RNA is antisense from about nucleotide 43,330 to about nucleotide 43,494 of SEQ ID NO:1. In yet another preferred embodiment, the RNA is antisense from about nucleotide 45,168 to about nucleotide 46,358 of SEQ ID NO:1.

The invention is directed in other embodiments to a method for assaying the effects of test compounds on the activity of a P2T receptor polypeptide comprising the steps of providing a transgenic animal comprising a polynucleotide encoding a murine P2T receptor polypeptide comprising the amino acid sequence of SEQ ID NO:2; administering a test compound to the animal; and determining the effects of the test compound on the activity of the P2T receptor polypeptide in the presence and absence of the test compound. In particular embodiments, the effects of the test compound on the animal are phenotypic. In a preferred embodiment, the receptor is expressed in glial cells or blood plasma cells of the animal. In yet another embodiment, the polynucleotide has at least one mutation selected from the group consisting of nucleotide deletion, nucleotide substitution and nucleotide insertion.

In one particular embodiment, the invention is directed to a method for assaying the effects of test compounds on the activity of a P2T receptor polypeptide comprising the steps of providing recombinant cells comprising a murine P2T receptor polypeptide comprising an amino acid sequence of SEQ ID NO:2; contacting the cells with a test compound; and determining the effects of the test compound on the activity of the P2T receptor polypeptide in the presence and absence of the test compound. In a preferred embodiment, determining the effects of the test compound are selected from the group consisting of measuring ADP levels, measuring $K^+$ levels, P2T kinase activity, measuring platelet morphology, measuring platelet aggregation, measuring P2T phosphorylation, measuring phosphatidyl inositol levels, measuring GTPase activity, measuring GTP levels, measuring cAMP levels, measuring GDP levels and measuring $Ca^{2+}$ levels. In another embodiment, the polynucleotide has at least one mutation selected from the group consisting of nucleotide deletion, nucleotide substitution and nucleotide insertion.

In still another embodiment, the invention is directed to a method for assaying the effects of test compounds on the activity of a P2T receptor polypeptide comprising the steps of providing yeast cells comprising a polynucleotide encoding a murine P2T receptor polypeptide comprising the amino acid sequence of SEQ ID NO:2 and a reporter gene operatively linked to the polynucleotide; contacting the cells with a test compound; and determining the effects of the test compound on the activity of the P2T receptor polypeptide by measuring expression levels of the reporter gene in the presence and absence of the test compound. In a preferred embodiment, the reporter gene is selected from the group consisting of β-galactosidase, HIS3, CAN1, CYH1, URA3, TRP1 and LYS2.

In yet another embodiment, the invention is directed to a method of producing a murine P2T receptor polypeptide comprising an amino acid sequence of SEQ ID NO:2 comprising transfecting, infecting or transforming a recombinant host cell with an expression vector comprising a polynucleotide comprising a nucleic acid sequence of SEQ ID NO:1 or a degenerate variant thereof; culturing the host cell under conditions sufficient for the production of the polypeptide; and isolating the polypeptide from the culture.

The invention further provides a method for the treatment of a subject in need of enhanced P2T receptor activity comprising administering to the subject a therapeutically effective amount of an agonist to the P2T receptor polypeptide; and/or administering to the subject a polynucleotide encoding a P2T receptor polypeptide comprising an amino acid sequence of SEQ ID NO:2, in a form so as to effect the production of the P2T polypeptide in vivo.

The invention is further directed to a method for the treatment of a subject in need of enhanced P2T receptor activity in the central nervous system comprising administering to the subject a therapeutically effective amount of an agonist to the P2T receptor polypeptide; and/or administering to the subject a polynucleotide encoding a P2T receptor polypeptide comprising an amino acid sequence of SEQ ID NO:2, in a form so as to effect the production of the P2T receptor polypeptide in vivo.

In another embodiment, the invention is directed to a method for the treatment of a subject in need of inhibiting P2T receptor polypeptide activity comprising administering to the subject a therapeutically effective amount of an antagonist to the P2T receptor polypeptide; and/or administering to the subject a polynucleotide that inhibits the expression of a polynucleotide encoding a P2T receptor polypeptide comprising an amino acid sequence of SEQ ID NO:2; and/or administering to the subject a therapeutically effective amount of a polypeptide that competes with a P2T receptor polypeptide for its ligand.

In yet another particular embodiment, the invention is directed to a method for the treatment of a subject in need of inhibiting P2T receptor polypeptide activity in the central nervous system comprising administering to the subject a therapeutically effective amount of an antagonist to the P2T receptor polypeptide; and/or administering to the subject a polynucleotide that inhibits the expression of a polynucleotide encoding a P2T receptor polypeptide comprising an amino acid sequence of SEQ ID NO:2; and/or administering to the subject a therapeutically effective amount of a polypeptide that competes with a P2T receptor polypeptide for its ligand.

In other embodiments the invention is directed to a method for the diagnosis of a central nervous system disease or the susceptibility to a central nervous system disease in a subject related to the expression or activity of a P2T receptor polypeptide in the subject comprising determining the presence or absence of a mutation in a polynucleotide encoding a P2T receptor polypeptide comprising the amino acid sequence of SEQ ID NO:2; and/or assaying for the presence of P2T expression in a sampled derived from the subject, wherein the P2T expressed is a polynucleotide encoding a P2T polypeptide comprising the amino acid sequence of SEQ ID NO:2.

In yet another embodiment, the invention provides a method of inhibiting expression of the P2T gene in a cell comprising providing the cell with a polynucleotide antisense to the nucleic acid sequence of SEQ ID NO:1. In a preferred embodiment, the cell is a glial cell or platelet cell.

In a further embodiment, the invention is directed to a neural cell line stably expressing a P2T polypeptide comprising the amino acid sequence of SEQ ID NO:2, a variant thereof or a fragment thereof. In a preferred embodiment, the cell is a glial cell.

In one particular embodiment, the invention is directed to a method for treating a subject for a nervous system disorder comprising modulating the activity of the P2T receptor polypeptide comprising the amino acid sequence of SEQ ID NO:2 and/or modulating the expression of a polynucleotide encoding a P2T receptor polypeptide comprising the amino acid sequence of SEQ ID NO:2.

In another embodiment, the invention provides a method for producing a transgenic animal whose genome comprises a functional disruption in a polynucleotide encoding a P2T receptor polypeptide, the method comprising providing a polynucleotide encoding a P2T receptor polypeptide having a functional disruption; introducing the disrupted polynucleotide into embryonic stem cells; selecting those embryonic stem cells that comprise the disrupted polynucleotide; introducing the embryonic stem cell into a blastocyst; transferring the blastocyst to a pseudopregnant animal; and allowing the transferred blastocyst to develop into an animal chimeric for the disruption. In a particular embodiment, the method further comprises breeding the chimeric animal with a wild-type animal to obtain animals heterozygous for the disruption. In another embodiment, the method further comprises breeding the heterozygous animal to generate animal homozygous for the disruption. In a preferred embodiment, the animal has a central nervous system disorder. In another preferred embodiment, the animal has a blood plasma disorder.

The invention is directed in a further embodiment, to a method for assaying the effects of test compounds on the binding interaction of a P2T receptor polypeptide and a P2T substrate polypeptide comprising the steps of providing yeast cells for a yeast two-hybrid system comprising a P2T receptor polypeptide having an amino acid sequence of SEQ ID NO:2 and a P2T substrate polypeptide; contacting the cells with a test compound; and determining the effect of the test compound on the binding interaction of the P2T receptor polypeptide and the P2T substrate polypeptide in the presence and absence of the test compound.

In a particular embodiment, the invention is directed to a method for inhibiting the expression of a P2T polynucleotide in a cell the method comprising providing the cell with a nucleic acid molecule antisense to the polynucleotide of SEQ ID NO:1.

In yet another embodiment, the invention is directed to a method of providing a P2T protein to a mammal comprising introducing into the mammal a homologously recombinant cell which produces the P2T protein, the homologously recombinant cell being generated by the method comprising providing a vertebrate cell, the genomic DNA of which comprises an endogenous P2T gene; providing a DNA construct comprising a targeting sequence of the nucleic acid sequence of SEQ ID NO:1 from about nucleotide 1 to about nucleotide 45,167 of SEQ ID NO:1, which is homologous to a target site upstream of the endogenous P2T gene, an exogenous regulatory sequence, an exon and an unpaired splice-donor site at the 3' end of the exon, wherein the exogenous regulatory sequence is operatively linked to the exon and transfecting the cell with the DNA construct, thereby generating a homologously recombinant cell in which the splice-donor site is operatively linked to the second exon of the endogenous gene and the exogenous regulatory sequence controls transcription of the construct-derived exon, the endogenous P2T gene and any sequence between the construct-derived exon and the endogenous P2T gene, to produce an RNA transcript that encodes a P2T protein.

In still another embodiment, the invention provides a method for the treatment of a subject in need of enhanced P2T receptor activity in platelet cells comprising administering to the subject a therapeutically effective amount of an agonist to the P2T receptor polypeptide; and/or administering to the subject a polynucleotide encoding a P2T receptor polypeptide comprising an amino acid sequence of SEQ ID NO:2, in a form so as to effect the production of the P2T receptor polypeptide in vivo.

In another particular embodiment, the invention is directed to a method for the treatment of a subject in need of inhibiting P2T receptor activity in platelet cells comprising administering to the subject a therapeutically effective amount of an antagonist to the P2T receptor polypeptide; and/or administering to the subject a polynucleotide that inhibits the expression of a polynucleotide encoding a P2T receptor polypeptide comprising an amino acid sequence of SEQ ID NO:2; and/or administering to the subject a therapeutically effective amount of a polypeptide that competes with a P2T receptor polypeptide for its ligand.

In still another embodiment, the invention is directed to a method for the diagnosis of a blood platelet disease or the susceptibility to a blood platelet disease in a subject related to the expression or activity of a P2T receptor polypeptide in the subject comprising determining the presence or absence of a mutation in a polynucleotide encoding a P2T receptor polypeptide comprising the amino acid sequence of SEQ ID NO:2; and/or assaying for the presence of P2T expression in a sampled derived from the subject, wherein the P2T expressed is a polynucleotide encoding a P2T polypeptide comprising the amino acid sequence of SEQ ID NO:2.

Other features and advantages of the invention will be apparent from the following detailed description, from the preferred embodiments thereof, and from the claims.

BRIEF DESCRIPTION OF THE DRAWINGS

FIG. 1 shows an amino acid sequence alignment of human (SEQ ID NO:11), rat (SEQ ID NO:11) and mouse (SEQ ID NO:2) P2T receptors. Non-conservative replacements are highlighted in black, conserved amino acid replacements are highlighted in grey. Putative transmembrane domains (TM1–7) are underlined. ClustalW was used to perform the alignment.

DETAILED DESCRIPTION OF THE INVENTION

Figure 2:
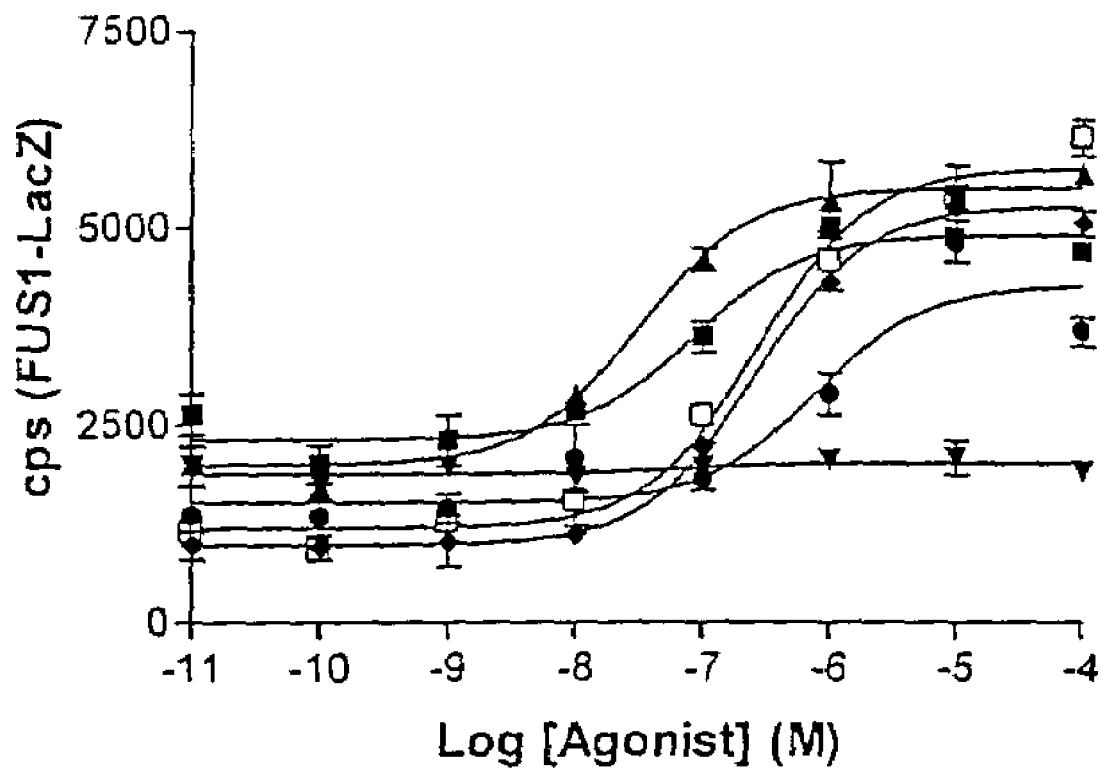
FIG. 2 shows the pharmacological characterization of mouse P2T receptor expressed in yeast cells. MPY578t5 cells containing pMP344 were assayed for agonist-induced stimulation of β-galactosidase activity. Symbols: square, 2MeSATP; triangle, 2MeSADP; inverted triangle, 2ClATP; diamond, ADP; circle, ATPγS; open square, ADPβS.

In an effort to identify genes encoding orphan G-protein coupled receptors (P2Ts), the present invention has identified a genomic polynucleotide sequence encoding a murine ortholog of the human P2T G-protein coupled receptor, hereinafter the P2T receptor. The murine ortholog of the human P2T receptor was identified by querying mouse genomic and cDNA databases using the human orphan GPCR sequence, EBI-2 (U.S. Pat. No. 6,060,272). A yeast-based GPCR expression technology (Pausch, 1997) was employed to demonstrate that the murine polynucleotide sequence of the invention encodes a GPCR with pharmacological properties equivalent to the human P2T receptor. The murine mRNA was expressed at high levels in the brain, particularly in glial cells and in various peripheral tissues, including those that contain platelets. Results of the present invention, using the yeast GPCR expression system (Pausch, 1997), are in excellent agreement with the three different measures of human P2T pharmacological activity.

Thus, the present invention relates to a newly identified murine genomic polynucleotide sequence that encodes a P2T receptor which is expressed at high levels in the central nervous system, the use of such polynucleotides and polypeptides, as well as the production of such polynucleotides and polypeptides. The invention relates also to identifying compounds which may be agonists, antagonists and/or inhibitors of P2T, and therefore potentially useful in therapy.

In certain embodiments the present invention relates to an isolated genomic polynucleotide comprising a nucleic acid sequence of SEQ ID NO:1, encoding a P2T receptor polypeptide or fragments thereof. In other embodiments the invention relates to P2T receptor polypeptides comprising an amino acid sequence of SEQ ID NO:2. In yet other embodiments, the invention provides recombinant vectors comprising a polynucleotide encoding a P2T receptor polypeptide. In another embodiment, a vector comprising a polynucleotide encoding a P2T receptor polypeptide is comprised within a host cell, wherein the vector expresses the polynucleotide to produce the encoded polypeptide or fragment thereof. In further embodiments, methods for assaying test compounds for their ability to modulate the activity of P2T receptor polypeptides, methods for producing P2T receptor polypeptides, and methods for the diagnosis of a disease or the susceptibility to a disease in a subject related to the expression or activity of a P2T receptor are provided, as well as methods for treating a subject in need of inhibiting or activating P2T activity.

A. Isolated Polynucleotides that Encode the P2T Receptor

Isolated and purified P2T polynucleotides of the present invention are contemplated for use in the production of P2T receptor polypeptides. Thus, in one aspect, the present invention provides isolated and purified polynucleotides that encode P2T receptor polypeptides. In particular embodiments, an isolated murine genomic polynucleotide comprises a nucleic acid sequence of SEQ ID NO:1 and encodes a P2T receptor polypeptide comprising an amino acid sequence of SEQ ID NO:2. In particular embodiments, a polynucleotide of the present invention is a DNA molecule. In a preferred embodiment, a polynucleotide of the present invention encodes a P2T receptor polypeptide comprising an amino acid sequence that has at least 95% identity to an amino acid sequence of SEQ ID NO:2, or a fragment thereof.

In another embodiment of the invention, an isolated and purified P2T polynucleotide is a genomic mouse cDNA sequence comprising the nucleic acid sequence of SEQ ID NO:1. The nucleic acid sequence of SEQ ID NO:1 comprises a 46,358 base pair nucleotide sequence encoding the mouse P2T promoter and transcript (see SEQ ID NO:1). The mouse P2T mRNA of SEQ ID NO:1 is encoded in four exons (Exon I, SEQ ID NO:3; Exon II, SEQ ID NO:4; Exon III, SEQ ID NO:5; and Exon IV, SEQ ID NO:6), three of which comprise the 5' untranslated region. The entire mouse P2T open reading frame is encoded in a single uninterrupted exon (Exon IV, SEQ ID NO:6) from nucleotide 45,167 to nucleotide 46,358 of SEQ ID NO:1.

In another aspect of the invention, an isolated and purified polynucleotide comprises a nucleic acid sequence that has at least 95% identity to the nucleic acid sequence selected of SEQ ID NO:1, a degenerate variant thereof, or a complement thereof.

As used herein, the term "polynucleotide" means a sequence of nucleotides connected by phosphodiester linkages. Polynucleotides are presented herein in the direction from the 5' to the 3' direction. A polynucleotide of the present invention can comprise from about 40 to about several hundred thousand base pairs. Preferably, a polynucleotide comprises from about 10 to about 3,000 base pairs. Preferred lengths of particular polynucleotide are set forth hereinafter.

A polynucleotide of the present invention can be a deoxyribonucleic acid (DNA) molecule, a ribonucleic acid (RNA) molecule, or analogs of the DNA or RNA generated using nucleotide analogs. The nucleic acid molecule can be single-stranded or double-stranded, but preferably is double-stranded DNA. Where a polynucleotide is a DNA molecule, that molecule can be a gene, a cDNA molecule or a genomic DNA molecule. Nucleotide bases are indicated herein by a single letter code: adenine (A), guanine (G), thymine (T), cytosine (C), inosine (I) and uracil (U).

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed herein.

In certain embodiments, an "isolated" polynucleotide is free of sequences which naturally flank the nucleic acid (i.e., sequences located at the 5' and 3' ends of th nucleic acid) in the genomic DNA of the organism from which the nucleic acid is derived. For example, in various embodiments, the isolated P2T nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., neuronal or red blood cells). However, the P2T nucleic acid molecule can be fused to other protein encoding or regulatory sequences and still be considered isolated.

However, in other embodiments, an isolated polynucleotide comprises a murine genomic polynucleotide sequence disclosed in SEQ ID NO:1.

Polynucleotides of the present invention may be obtained, using standard cloning and screening techniques, from a cDNA library derived from mRNA from human cells or from genomic DNA. Polynucleotides of the invention can also synthesized using well known and commercially available techniques.

The invention further encompasses nucleic acid molecules that differ from the nucleotide sequence shown in SEQ ID NO:1, (and fragments thereof) due to degeneracy of the genetic code and thus encode the same P2T receptor polypeptide as that encoded by the nucleotide sequence shown in SEQ ID NO:1.

In another preferred embodiment, an isolated polynucleotide of the invention comprises a nucleic acid molecule which is a complement of the nucleotide sequence shown in SEQ ID NO:1, or a fragment of this nucleotide sequence. A nucleic acid molecule which is complementary to the nucleotide sequence shown in SEQ ID NO:1 is one which is sufficiently complementary to the nucleotide sequence SEQ ID NO:1, such that it can hybridize to the nucleotide sequence shown in SEQ ID NO:1, thereby forming a stable duplex. Examples of hybridization stringency conditions are detailed in Table 1.

Orthologues and allelic variants of the murine P2T receptor polynucleotides can readily be identified using methods well known in the art. Allelic variants and orthologues of P2T will comprise a nucleotide sequence that is typically at least about 70–75%, more typically at least about 80–85%, and most typically at least about 90–95% or more homologous to the nucleotide sequence shown in SEQ ID NO:1, or a fragment of this nucleotide sequence. Such nucleic acid molecules can readily be identified as being able to hybridize, preferably under stringent conditions, to the nucleotide sequence shown in SEQ ID NO:1, or a fragment of this nucleotide sequence.

Moreover, the polynucleotide of the invention can comprise only a fragment of the coding region of a P2T polynucleotide or gene, such as a fragment of SEQ ID NO:1.

When the polynucleotides of the invention are used for the recombinant production of P2T receptor polypeptides of the present invention, the polynucleotide may include the coding sequence for the mature polypeptide, by itself, or the coding sequence for the mature polypeptide in reading frame with other coding sequences, such as those encoding a leader or secretory sequence, a pre-, or pro- or prepro-polypeptide sequence, or other fusion peptide portions. For example, a marker sequence which facilitates purification of the fused polypeptide can be encoded (see Gentz et al., 1989, incorporated herein by reference). The polynucleotide may also contain non-coding 5' and 3' sequences, such as transcribed, non-translated sequences, splicing and polyadenylation signals, ribosome binding sites and sequences that stabilize mRNA.

In addition to the P2T nucleotide sequences shown in SEQ ID NO:1, it will be appreciated by those skilled in the art that DNA sequence polymorphisms that lead to changes in the amino acid sequences of a P2T receptor polypeptide may exist within a population (e.g., a mouse, rat or human population). Such genetic polymorphism in the P2T gene or polynucleotide may exist among individuals within a population due to natural allelic variation. As used herein, the terms "gene" and "recombinant gene" refer to polynucleotides comprising an open reading frame encoding a P2T receptor polypeptide, preferably a mammalian P2T receptor polypeptide. Such natural allelic variations can typically result in 1–5% variance in the nucleotide sequence of the P2T polynucleotide. Any and all such nucleotide variations and resulting amino acid polymorphisms in a P2T polynucleotide that are the result of natural allelic variation are intended to be within the scope of the invention. Such allelic variation includes both active allelic variants as well as non-active or reduced activity allelic variants, the latter two types typically giving rise to a pathological disorder.

Moreover, nucleic acid molecules encoding P2T receptor polypeptides from other species, and thus which have a nucleotide sequence which differs from the murine sequence of SEQ ID NO:1, are intended to be within the scope of the invention. Polynucleotides corresponding to natural allelic variants and non-murine orthologues of the murine P2T cDNA of the invention can be isolated based on their homology to the murine P2T polynucleotides disclosed herein using the murine cDNA, or a fragment thereof, as a hybridization probe according to standard hybridization techniques under stringent hybridization conditions.

Thus, a polynucleotide encoding a polypeptide of the present invention, including homologs and orthologs from species other than murine, may be obtained by a process which comprises the steps of screening an appropriate library under stringent hybridization conditions with a labeled probe having the sequence of SEQ ID NO:1, or a fragment thereof; and isolating full-length cDNA and genomic clones containing the polynucleotide sequence (see, Table 1). Such hybridization techniques are well known to the skilled artisan, e.g., Sambrook et al., 1989, Molecular Cloning: A Laboratory Manual, Cold Spring Harbor Laboratory Press, Cold Spring Harbor, N.Y., chapters 9 and 11, and Ausubel et al., 1995, Current Protocols in Molecular Biology, eds., John Wiley & Sons, Inc., sections 2.10 and 6.3–6.4, incorporated herein by reference. The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low "processivity" (a measure of the ability of the enzyme to remain attached to the template during the polymerization reaction), failing to complete a DNA copy of the mRNA template during 1st strand cDNA synthesis.

Thus, in certain embodiments, the polynucleotide sequence information provided by the present invention allows for the preparation of relatively short DNA (or RNA) oligonucleotide sequences having the ability to specifically hybridize to gene sequences of the selected polynucleotides disclosed herein. The term "oligonucleotide" as used herein is defined as a molecule comprised of two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. Thus, in particular embodiments of the invention, nucleic acid probes of an appropriate length are prepared based on a consideration of a selected nucleotide sequence, e.g., a sequence such as that shown in SEQ ID NO:1. The ability of such nucleic acid probes to specifically hybridize to a polynucleotide encoding a P2T receptor lends them particular utility in a variety of embodiments. Most importantly, the probes can be used in a variety of assays for detecting the presence of complementary sequences in a given sample.

In certain embodiments, it is advantageous to use oligonucleotide primers. These primers may be generated in any manner, including chemical synthesis, DNA replication, reverse transcription, or a combination thereof. The sequence of such primers is designed using a polynucleotide of the present invention for use in detecting, amplifying or mutating a defined segment of a gene or polynucleotide that encodes a P2T receptor polypeptide from mammalian cells using polymerase chain reaction (PCR) technology.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

Polynucleotides which are identical or sufficiently identical to a nucleotide sequence contained in SEQ ID NO:1 or a fragment thereof, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding homologs and orthologs from species other than mouse) that have a high sequence similarity to of SEQ ID NO:1 or a fragment thereof. Typically these nucleotide sequences are from at least about 70% identical to at least about 95% identical to that of the reference polynucleotide sequence. The probes or primers will generally comprise at least 15 nucleotides, preferably, at least 30 nucleotides and may have at least 50 nucleotides. Particularly preferred probes will have between 30 and 50 nucleotides.

There are several methods available and well known to those skilled in the art to obtain full-length cDNAs, or extend short cDNAs, for example those based on the method of Rapid Amplification of cDNA ends (RACE) (see, Frohman et al., 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an "adaptor" sequence ligated onto each end. Nucleic acid amplification (PCR) is then carried out to amplify the "missing" 5' end of the cDNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

To provide certain advantages in accordance with the present invention, a preferred nucleic acid sequence employed for hybridization studies or assays includes probe molecules that are complementary to at least a 10 to 70 or so long nucleotide stretch of a polynucleotide that encodes a P2T receptor polypeptide, such as that shown in SEQ ID NO:2. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 25 to 40 nucleotides, 55 to 70 nucleotides, or even longer where desired. Such fragments can be readily prepared by, for example, directly synthesizing the fragment by chemical means, by application of nucleic acid reproduction technology, such as the PCR technology of U.S. Pat. No. 4,683,202 (incorporated by reference herein in its entirety) or by excising selected DNA fragments from recombinant plasmids containing appropriate inserts and suitable restriction enzyme sites.

In another aspect, the present invention contemplates an isolated and purified polynucleotide comprising a base sequence that is identical or complementary to a segment of at least 10 contiguous bases of SEQ ID NO:1, wherein the polynucleotide hybridizes to a polynucleotide that encodes a P2T receptor polypeptide. Preferably, the isolated and purified polynucleotide comprises a base sequence that is identical or complementary to a segment of at least 25 to 70 contiguous bases of SEQ ID NO:1. For example, the polynucleotide of the invention can comprise a segment of bases identical or complementary to 40 or 55 contiguous bases of the disclosed nucleotide sequences.

Accordingly, a polynucleotide probe molecule of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids (see Table 1 below).

Of course, for some applications, for example, where one desires to prepare mutants employing a mutant primer strand hybridized to an underlying template or where one seeks to isolate a P2T receptor polypeptide coding sequence from other cells, functional equivalents, or the like, less stringent hybridization conditions are typically needed to allow formation of the heteroduplex. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

The present invention also includes polynucleotides capable of hybridizing under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic

TABLE 1

Stringency Conditions

| Stringency Condition | Polynucleotide Hybrid | Hybrid Length (bp)[I] | Hybridization Temperature and Buffer[H] | Wash Temperature and BufferH |
|---|---|---|---|---|
| A | DNA:DNA | >50 | 65° C.; 1 × SSC -or- 42° C.; 1 × SSC, 50% formamide | 65° C.; 0.3 × SSC |
| B | DNA:DNA | <50 | $T_B$; 1 × SSC | $T_B$; 1 × SSC |
| C | DNA:RNA | >50 | 67° C.; 1 × SSC -or- 45° C.; 1 × SSC, 50% formamide | 67° C.; 0.3 × SSC |
| D | DNA:RNA | <50 | $T_D$; 1 × SSC | $T_D$; 1 × SSC |
| E | RNA:RNA | >50 | 70° C.; 1 × SSC -or- 50° C.; 1 × SSC, 50% formamide | 70° C.; 0.3 × SSC |
| F | RNA:RNA | <50 | $T_F$; 1 × SSC | $T_F$; 1 × SSC |
| G | DNA:DNA | >50 | 65° C.; 4 × SSC -or- 42° C.; 4 × SSC, 50% formamide | 65° C.; 1 × SSC |
| H | DNA:DNA | <50 | $T_H$; 4 × SSC | $T_H$; 4 × SSC |
| I | DNA:RNA | >50 | 67° C.; 4 × SSC -or- 45° C.; 4 × SSC, 50% formamide | 67° C.; 1 × SSC |
| J | DNA:RNA | <50 | $T_J$; 4 × SSC | $T_J$; 4 × SSC |
| K | RNA:RNA | >50 | 70° C.; 4 × SSC -or- 50° C.; 4 × SSC, 50% formamide | 67° C.; 1 × SSC |
| L | RNA:RNA | <50 | $T_L$; 2 × SSC | $T_L$; 2 × SSC |
| M | DNA:DNA | >50 | 50° C.; 4 × SSC -or- 40° C.; 6 × SSC, 50% formamide | 50° C.; 2 × SSC |
| N | DNA:DNA | <50 | $T_N$; 6 × SSC | $T_N$; 6 × SSC |
| O | DNA:RNA | >50 | 55° C.; 4 × SSC -or- 42° C.; 6 × SSC, 50% formamide | 55° C.; 2 × SSC |
| P | DNA:RNA | <50 | $T_P$; 6 × SSC | $T_P$; 6 × SSC |
| Q | RNA:RNA | >50 | 60° C.; 4 × SSC -or- 45° C.; 6 × SSC, 50% formamide | 60° C.; 2 × SSC |
| R | RNA:RNA | <50 | $T_R$; 4 × SSC | $T_R$; 4 × SSC |

(bp)[I]: The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning thesequences of the polynucleotides and identifying the region or regions of optimal sequence complementarity.
Buffer[H]: SSPE (1 × SSPE is 0.15 M NaCl, 10 mM $NaH_2PO_4$, and 1.25 mM EDTA, pH 7.4) can be substituted for SSC (1 × SSC is 0.15 M NaCl and 15 mM sodium citrate) in the hybridization and wash buffers; washes are performed for 15 minutes after hybridization is complete.
$T_B$ through $T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$[$Na^+$]) + 0.41(% G + C) − (600/N), where N is the number of bases in the hybrid, and [$Na^+$] is the concentration of sodium ions in the hybridization buffer ([$Na^+$] for 1 × SSC = 0.165 M).

Additional examples of stringency conditions for polynucleotide hybridization are provided in Sambrook et al., 1989, Molecular Cloning: A Laboratory Manual, Cold Spring Harbor Laboratory Press, Cold Spring Harbor, N.Y., chapters 9 and 11, and Ausubel et al., 1995, Current Protocols in Molecular Biology, eds., John Wiley & Sons, Inc., sections 2.10 and 6.3–6.4, incorporated herein by reference.

In addition to the nucleic acid molecules encoding P2T receptor polypeptides described above, another aspect of the invention pertains to isolated nucleic acid molecules which acid. The antisense nucleic acid can be complementary to an entire P2T coding strand (e.g., SEQ ID NO:1), or to only a fragment thereof. In one embodiment, an antisense nucleic acid molecule is antisense to a "coding region" of the coding strand of a nucleotide sequence encoding a P2T receptor polypeptide.

The term "coding region" refers to the region of the nucleotide sequence comprising codons which are translated into amino acid residues, e.g., the entire coding region of SEQ ID NO:1, comprises about nucleotides 45,167 to about 46,358. In another embodiment, the antisense nucleic acid molecule is antisense to a "noncoding region" of the coding strand of a nucleotide sequence encoding a P2T receptor polypeptide. The term "noncoding region" refers to 5' and 3' sequences which flank the coding region that are not translated into amino acids (i.e., also referred to as 5' and 3' untranslated regions).

Given the coding strand sequence encoding the P2T polypeptide disclosed herein (e.g., SEQ ID NO:1), antisense nucleic acids of the invention can be designed according to the rules of Watson and Crick base pairing. The antisense nucleic acid molecule can be complementary to the entire coding region of P2T mRNA, but more preferably is an oligonucleotide which is antisense to only a fragment of the coding or noncoding region of P2T mRNA. For example, the antisense oligonucleotide can be complementary to the region surrounding the translation start site of P2T mRNA.

An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, I-methylguanine, I-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a P2T receptor polypeptide to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual γ-units, the strands run parallel to each other (Gaultier et al., 1987). The antisense nucleic acid molecule can also comprise a 2'-o-methylribonucleotide (Inoue et al., 1987) or a chimeric RNA-DNA analogue (Inoue et al., 1987).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988)) can be used to catalytically cleave P2T mRNA transcripts to thereby inhibit translation of P2T mRNA. A ribozyme having specificity for a P2T-encoding nucleic acid can be designed based upon the nucleotide sequence of the P2T genomic DNA disclosed herein (i.e., SEQ ID NO:I). For example, a derivative of a Tetrahymena L-19 IVS RNA can be constructed in which the nucleotide sequence of the active site is complementary to the nucleotide sequence to be cleaved in a P2T-encoding mRNA. See, e.g., Cech et al. U.S. Pat. No. 4,987,071 and Cech et al. U.S. Pat. No. 5,116,742, both of which are incorporated by reference herein in their entirety. Alternatively, P2T mRNA can be used to select a catalytic RNA having a specific ribonuclease activity from a pool of RNA molecules. See, e.g., Bartel and Szostak, 1993).

Alternatively P2T gene expression can be inhibited by targeting nucleotide sequences complementary to the regulatory region of the P2T gene (e.g., the P2T gene promoter and/or enhancers) to form triple helical structures that prevent transcription of the P2T gene in target cells. See generally, Helene, 1991; Helene et al., 1992; and Maher, 1992).

P2T gene expression can also be inhibited using RNA interference (RNAi). This is a technique for post-transcriptional gene silencing (PTGS), in which target gene activity is specifically abolished with cognate double-stranded RNA (dsRNA). RNAi resembles in many aspects PTGS in plants and has been detected in many invertebrates including trypanosome, hydra, planaria, nematode and fruit fly (*Drosophila melangnoster*). It may be involved in the modulation of transposable element mobilization and antiviral state formation. RNAi in mammalian systems is disclosed in International Application No. WO 00/63364 which is incorporated by reference herein in its entirety. Basically, dsRNA of at least about 600 nucleotides, homologous to the target (P2T) is introduced into the cell and a sequence specific reduction in gene activity is observed.

B. P2T Receptor Polypeptides

In particular embodiments, the present invention provides isolated and purified P2T polypeptides. Preferably, a P2T receptor polypeptide of the invention is a recombinant polypeptide. Typically, a P2T receptor is produced by recombinant expression in a non-human cell. In certain embodiments, a P2T receptor polypeptide of the present invention comprises an amino acid sequence that has at least 95% identity to the amino acid sequence of SEQ ID NO:2, a variant thereof or a fragment thereof.

A P2T receptor polypeptide according to the present invention encompasses a polypeptide that comprises: 1) the amino acid sequence shown in SEQ ID NO:2; 2) functional and non-functional naturally occurring allelic variants of murine P2T receptor polypeptides; 3) recombinantly produced variants of murine P2T receptor polypeptides; and 4) P2T receptor polypeptides isolated from organisms other than mice (orthologues of murine P2T receptor polypeptide.)

An allelic variant of murine P2T receptor polypeptides according to the present invention encompasses 1) a polypeptide isolated from murine cells or tissues; 2) a polypeptide encoded by the same genetic locus as that encoding the murine P2T receptor polypeptide; and 3) a polypeptide that contains substantially homology to a murine P2T receptor.

Allelic variants of murine P2T include both functional and non-functional P2T receptor polypeptides. Functional allelic variants are naturally occurring amino acid sequence variants of the murine P2T receptor polypeptide that maintain the ability to bind a P2T receptor ligand and transduce a signal within a cell. Functional allelic variants will typically contain only conservative substitution of one or more amino acids of SEQ ID NO:2, or substitution, deletion or insertion of non-critical residues in non-critical regions of the polypeptide.

Non-functional allelic variants are naturally occurring amino acid sequence variants of murine P2T receptor polypeptide that do not have the ability to either bind ligand and/or transduce a signal within a cell. Non-functional allelic variants will typically contain a non-conservative substitution, a deletion, or insertion or premature truncation of the amino acid sequence of SEQ ID NO:2, or a substitution, insertion or deletion in critical residues or critical regions.

The present invention further provides non-murine orthologues of the murine P2T receptor polypeptide. Orthologues of murine P2T receptor polypeptide are polypeptides that are isolated from non-murine P2T organisms and possess the same ligand binding and signaling capabilities of the murine P2T polypeptide. Orthologues of the murine P2T receptor polypeptide can readily be identified as comprising an amino acid sequence that is substantially homologous to SEQ ID NO:2.

Modifications and changes can be made in the structure of a polypeptide of the present invention and still obtain a molecule having P2T like receptor characteristics. For example, certain amino acids can be substituted for other amino acids in a sequence without appreciable loss of receptor activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte & Doolittle, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within +/−2 is preferred, those which are within +/−1 are particularly preferred, and those within +/−0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated by reference herein in its entirety, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (see Table 2, below). The present invention thus contemplates functional or biological equivalents of a P2T receptor polypeptide as set forth above.

TABLE 2

| Original Residue | Exemplary Residue Substitution |
| --- | --- |
| Ala | Gly; Ser |
| Arg | Lys |
| Asn | Gln; His |
| Asp | Glu |

TABLE 2-continued

| Original Residue | Exemplary Residue Substitution |
|---|---|
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of sit -specific mutagenesis is well known in the art. As will be appreciated, the technique typically employs a phage vector which can exist in both a single stranded and double stranded form. Typically, site-directed mutagenesis in accordance herewith is performed by first obtaining a single-stranded vector which includes within its sequence a DNA sequence which encodes all or a portion of the P2T polypeptide sequence selected. An oligonucleotide primer bearing the desired mutated sequence is prepared (e.g., synthetically). This primer is then annealed to the single-stranded vector, and extended by the use of enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutation. Commercially available kits come with all the reagents necessary, except the oligonucleotide primers.

The P2T receptor polypeptide is a P2T receptor that participates in signaling pathways within cells. As used herein, a signaling pathway refers to the modulation (e.g., stimulated or inhibited) of a cellular function/activity upon the binding of a ligand to the P2T receptor. Examples of such functions include mobilization of intracellular molecules that participate in a signal transduction pathway, e.g., phosphatidylinositol 4,5-bisphosphate ($PIP_2$), inositol 1,4,5-triphosphate, adenylate cyclase, $Ca^{2+}$, ADP and ATP; inhibition or activation of adenylyl cyclase; neurotransmitters; polarization of the plasma membrane; production or secretion of molecules; alteration in the structure of a cellular component; cell proliferation, e.g., synthesis of DNA; cell migration; cell differentiation; and cell survival.

Depending on the type of cell, the response mediated by the P2T receptor polypeptide/ligand binding may be different. For example, in some cells, binding of a ligand to a P2T receptor polypeptide may stimulate an activity such as adhesion, migration, differentiation, etc. through phosphatidylinositol or cyclic AMP metabolism and turnover while in other cells, the binding of the ligand to the P2T receptor polypeptide will produce a different result. Regardless of the cellular activity modulated by P2T receptor, it is universal that the P2T receptor polypeptide is a P2T and interacts with a "G-protein" to produce one or more secondary signals in a variety of intracellular signal transduction pathways, e.g., through phosphatidylinositol or cyclic AMP metabolism and turnover, in a cell. G-proteins represent a family of heterotrimeric polypeptides composed of $\alpha$, $\beta$ and $\gamma$ subunits, which bind guanine nucleotides. These polypeptides are usually linked to cell surface receptors, e.g., receptors containing seven transmembrane domains, such as the ligand receptors. Following ligand binding to the receptor, a conformational change is transmitted to the G-protein, which causes the $\alpha$-subunit to exchange a bound GDP molecule for a GTP molecule and to dissociate from the $\beta$ and $\gamma$-subunits. The GTP-bound form of the $\alpha$-subunit typically functions as an effector-modulating moiety, leading to the production of second messengers, such as cyclic AMP (e.g., by activation of adenylate cyclase), diacylglycerol or inositol phosphates. As well, the free $\beta\gamma$-subunit complex may function as an effector-modulating moiety, leading to the production of second messengers, such as cyclic AMP (e.g., by activation of adenylate cyclase), diacylglycerol or inositol phosphates. Greater than 20 different types of $\alpha$-subunits are known in man, which associate with a smaller pool of $\beta$ and $\gamma$ subunits.

As used herein, "phosphatidylinositol turnover and metabolism" refers to the molecules involved in the turnover and metabolism of phosphatidylinositol 4,5-bisphosphate ($PIP_2$) as well as to the activities of these molecules. $PIP_2$ is a phospholipid found in the cytosolic leaflet of the plasma membrane. Binding of a ligand to the GPCR, (e.g., P2T) activates, in some cells, the plasma-membrane enzyme phospholipase C that in turn can hydrolyze $PIP_2$ to produce 1,2-diacylglycerol (DAG) and inositol 1,4,5-triphosphate ($IP_3$). Once formed $IP_3$ can diffuse to the endoplasmic reticulum surface where it can bind an $IP_3$ receptor, e.g., a calcium channel polypeptide containing an IP3 binding site. $IP_3$ binding can induce opening of the channel, allowing calcium ions to be released into the cytoplasm. $IP_3$ can also be phosphorylated by a specific kinase to form, a molecule which can cause calcium entry into the cytoplasm from the extracellular medium. $IP_3$ and inositol 1,3,4,5-tetraphosphate can subsequently be hydrolyzed very rapidly to the inactive products inositol 1,4-biphosphate and inositol 1,3, 4-triphosphate, respectively. These inactive products can be recycled by the cell to synthesize $PIP_2$. The other second messenger produced by the hydrolysis of $PIP_2$, namely 1,2-diacylglycerol (DAG), remains in the cell membrane where it can serve to activate the enzyme polypeptide kinase C. Polypeptide kinase C is usually found soluble in the cytoplasm of the cell, but upon an increase in the intracellular calcium concentration, this enzyme can move to the plasma membrane where it can be activated by DAG. The activation of polypeptide kinase C in different cells results in various cellular responses such as the phosphorylation of glycogen synthase, or the phosphorylation of various transcription factors, e.g., NF-kB. The language "phosphatidylinositol activity," as used herein, refers to an activity of $PIP_2$ or one of its metabolites.

Another signaling pathway in which the P2T receptor polypeptide may participate is the cAMP turnover pathway. As used herein, "cyclic AMP turnover and metabolism" refers to the molecules involved in the turnover and metabolism of cyclic AMP (cAMP) as well as to the activities of these molecules. Cyclic AMP is a second messenger produced in response to ligand induced stimulation of certain G-protein-coupled receptors. In the ligand signaling pathway, binding of ligand to a ligand receptor can lead to the activation of the enzyme adenylate cyclase, which catalyzes the synthesis of cAMP. The newly synthesized cAMP can in turn activate a cAMP-dependent protein kinase. This activated kinase can, for example, phosphorylate a voltage-gated potassium channel polypeptide, or an associated polypeptide, and lead to the inability of the potassium channel to open during an action potential. The inability of the potassium channel to open results in a decrease in the outward flow of potassium, which normally repolarizes the membrane of a neuron, leading to prolonged membrane depolarization. Of course, the activated cAMP-dependent protein kinase can affect other molecules as well, such as enzymes (e.g., metabolic enzymes), transcription factors, adenylyl cyclase and the like.

A P2T receptor polypeptide of the present invention is understood to be any P2T polypeptide comprising substantial sequence similarity, structural similarity and/or functional similarity to a P2T polypeptide comprising the amino acid sequence of SEQ ID NO:2. In addition, a P2T polypeptide of the invention is not limited to a particular source. Thus, the invention provides for the general detection and isolation of the genus of P2T receptor polypeptides from a variety of sources.

It is contemplated in the present invention, that a P2T polypeptide may advantageously be cleaved into fragments for use in further structural or functional analysis, or in the generation of reagents such as P2T-related polypeptides and P2T-specific antibodies. This can be accomplished by treating purified or unpurified P2T with a peptidase such as endopolypeptidease glu-C (Boehringer, Indianapolis, Ind.). Treatment with CNBr is another method by which P2T fragments may be produced from natural P2T. Recombinant techniques also can be used to produce specific fragments of P2T.

In addition, the invention also contemplates that compounds sterically similar to a P2T may be formulated to mimic the key portions of the peptide structure, called peptidomimetics. Mimetics are peptide-containing molecules which mimic elements of polypeptide secondary structure. See, for example, Johnson et al. (1993). The underlying rationale behind the use of peptide mimetics is that the peptide backbone of polypeptides exists chiefly to orient amino acid side chains in such a way as to facilitate molecular interactions, such as those of receptor and ligand.

Successful applications of the peptide mimetic concept have thus far focused on mimetics of β-turns within polypeptides. Likely β-turn structures within a P2T polypeptide can be predicted by computer-based algorithms as discussed above. Once the component amino acids of the turn are determined, mimetics can be constructed to achieve a similar spatial orientation of the essential elements of the amino acid side chains, as discussed in Johnson et al. (1993).

"Fusion polypeptide" refers to a polypeptide encoded by two, often unrelated, fused genes or fragments thereof. For example, fusion polypeptides comprising various portions of constant region of immunoglobulin molecules together with another human polypeptide or part thereof have been described. In many cases, employing an immunoglobulin Fc region as a part of a fusion polypeptide is advantageous for use in therapy and diagnosis resulting in, for example, improved pharmacokinetic properties (see, e.g., U.S. Pat. No. 5,696,237). On the other hand, for some uses it would be desirable to be able to delete the Fc part after the fusion polypeptide has been expressed, detected and purified.

C. P2T Polynucleotide and Polypeptide Variants

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al 1984), BLASTP, BLASTN, and FASTA (Altschul, S. F., et al., 1990. The BLASTX program is publicly available from NCBI and other sources (BLAST Manual, Altschul, S., et al., NCBI NLM NIH Bethesda, Md. 20894; Altschul, S., et al., 1990). The well known Smith Waterman algorithm may also be used to determine identity.

By way of example, a genomic polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1, by the numerical percent of the respective percent identity(divided by 100) and subtracting that product from said total number of nucleotides in SEQ ID NO:1.

For example, an isolated murine P2T polynucleotide comprising a polynucleotide sequence that has at least 95% identity to the nucleic acid sequence of SEQ ID NO:1; a degenerate variant thereof or a fragment thereof, wherein the polynucleotide sequence may include up to $n_n$ nucleic acid alterations over the entire polynucleotide region of the nucleic acid sequence of SEQ ID NO:1, wherein $n_n$ is the maximum number of alterations and is calculated by the formula:

$$n_n \leq x_n - (x_n \cdot y),$$

in which $x_n$ is the total number of nucleic acids of SEQ ID NO:1 and y has a value of 0.95, wherein any non-integer product of $x_n$ and y is rounded down to the nearest integer prior to subtracting such product from $x_n$. Of course, y may also have a value of 0.80 for 80%, 0.85 for 85%, 0.90 for 90% 0.95 for 95%, etc. Alterations of a polynucleotide sequence encoding a P2T polypeptide of SEQ ID NO:2 may result in a functional P2T receptor polypeptide or a non-functional P2T receptor polypeptide. A functional P2T receptor polypeptide maintains the ability to bind a P2T receptor ligand and transduce a signal within a cell. A non-functional P2T receptor polypeptide lacks the ability to either bind ligand and/or transduce a signal within a cell.

D. Vectors, H st Cells and Recombinant P2T Polyp ptid s

In an alternate embodiment, the present invention provides expression vectors comprising polynucleotides that encode P2T polypeptides. Preferably, the expression vectors of the present invention comprise polynucleotides that encode polypeptides comprising the amino acid residue sequence of SEQ ID NO:2. More preferably, the expression vectors of the present invention comprise polynucleotides comprising the nucleotide base sequence of SEQ ID NO:1. Even more preferably, the expression vectors of the invention comprise polynucleotides operatively linked to an enhancer-promoter. In certain embodiments, the expression vectors of the invention comprise polynucleotides operatively linked to a prokaryotic promoter. Alternatively, the expression vectors of the present invention comprise polynucleotides operatively linked to an enhancer-promoter that is a eukaryotic promoter, and the expression vectors further comprise a polyadenylation signal that is positioned 3' of the carboxy-terminal amino acid and within a transcriptional unit of the encoded polypeptide.

Expression of proteins in prokaryotes is most often carried out in E. coli with vectors containing constitutive or inducible promoters directing the expression of either fusion or non-fusion proteins. Fusion vectors add a number of amino acids to a protein encoded therein, to the amino or carboxy terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith and Johnson,1988), pMAL (New England Biolabs, Beverly; Mass.) and pRIT5 (Pharmacia, Piscataway, N.J.) which fuse glutathione S-transferase (GST), maltose E binding protein, or protein A, respectively, to the target recombinant protein.

In one embodiment, the coding sequence of the P2T gene is cloned into a pGEX expression vector to create a vector encoding a fusion protein comprising, from the N-terminus to the C-t rminus, GST-thrombin cleavage site-P2T polypeptide. The fusion protein can be purified by affinity chromatography using glutathione-agarose resin. Recombinant P2T polypeptide unfused to GST can be recovered by cleavage of the fusion protein with thrombin.

Examples of suitable inducible non-fusion E. coli expression vectors include pTrc (Amann et al., 1988) and pET I I d (Studier et al., 1990). Target gene expression from the pTrc vector relies on host RNA polymerase transcription from a hybrid trp-lac fusion promoter. Target gene expression from the pET I I d vector relies on transcription from a T7 gn1 β-lac fusion promoter mediated by a coexpressed viral RNA polymerase J7 gn1. This viral polymerase is supplied by host strains BL21 (DE3) or HMS I 74(DE3) from a resident prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein. Another strategy is to alter the nucleic acid sequence of the nucleic acid to be inserted into an expression vector so that the individual codons for each amino acid are those preferentially utilized in E. coli. Such alteration of nucleic acid sequences of the invention can be carried out by standard DNA mutagenesis or synthesis techniques.

In another embodiment, the P2T polynucleotide expression vector is a yeast expression vector. Examples of vectors for expression in yeast S. cerivisae include pYepSec I (Baldari, et al., 1987), pMFa (Kurjan and Herskowitz, 1982), pJRY88 (Schultz et al., 1987), and pYES2 (Invitrogen Corporation, San Diego, Calif.), p416GPD and p426GPD (Mumberg et al., 1995).

Alternatively, a P2T polynucleotide can be expressed in insect cells using, for example, baculovirus expression vectors. Baculovirus vectors available for expression of proteins in cultured insect cells (e.g., Sf 9 cells) include the pAc series (Smith et al., 1983) and the pVL series (Lucklow and Summers, 1989).

In yet another embodiment, a polynucleotide of the invention is expressed in mammalian cells using a mammalian expression vector. Examples of mammalian expression vectors include pCDM8 (Seed, 1987) and pMT2PC (Kaufman et al., 1987). When used in mammalian cells, the expression vector's control functions are often provided by viral regulatory elements.

For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., "Molecular Cloning: A Laboratory Manual" 2nd, ed, Cold Spring Harbor Laboratory, Cold Spring Harbor Laboratory Press, Cold Spring Harbor, N.Y., 1989, incorporated herein by reference.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987), lymphoid-specific promoters (Calame and Eaton, 1988), in particular promoters of T cell receptors (Winoto and Baltimore, 1989) and immunoglobulins (Banerji et al., 1983), Queen and Baltimore (1983), neuron-specific promoters (e.g., the neurofilament promoter; Byrne and Ruddle, 1989), pancreas-specific promoters (Edlund et al., 1985), and mammary gland-specific promoters (e.g., milk whey promoter; U.S. Pat. No. 4,873,316 and International Application No. EP 264,166). Developmentally-regulated promoters are also encompassed, for example the murine hox promoters (Kessel and Gruss, 1990) and the α-fetoprotein promoter (Campes and Tilghman, 1989).

The present invention also relates to improved methods for both the in vitro production of P2T polypeptides and for the production and delivery of P2T polypeptides by gene therapy. The present invention includes approaches which activate expression of endogenous cellular genes, and further allows amplification of the activated endogenous cellular genes, which does not require in vitro manipulation and transfection of exogenous DNA encoding P2T polypeptides. These methods are described in PCT International Application WO 94/12650, U.S. Pat. No. 5,968,502, and Harrington et al., 2001, all of which are incorporated in their entirety by reference. These, and variations of them which one skilled in the art will recognize as equivalent, may collectively be referred to as "gene activation".

Thus, in certain embodiments, the invention relates to transfected cells, both transfected primary or secondary cells (i.e., non-immortalized cells) and transfected immortalized cells, useful for producing proteins, methods of making such cells, methods of using the cells for in vitro protein production and methods of gene therapy. Cells of the present invention are of vertebrate origin, particularly of mammalian origin and even more particularly of human origin. Cells produced by the method of the present invention contain exogenous DNA which encodes a therapeutic product, exogenous DNA which is itself a therapeutic product and/or exogenous DNA which causes the transfected cells to express a gene at a higher level or with a pattern of regulation or induction that is different than occurs in the corresponding nontransfected cell.

The present invention also relates to methods by which primary, secondary, and immortalized cells are transfected to include exogenous genetic material, methods of producing clonal cell strains or heterogeneous cell strains, and methods of immunizing animals, or producing antibodies in immunized animals, using the transfected primary, secondary, or immortalized cells.

The present invention relates particularly to a method of gene targeting or homologous recombination in cells of vertebrate, particularly mammalian, origin. That is, it relates to a method of introducing DNA into primary, secondary, or immortalized cells of vertebrate origin through homologous recombination, such that the DNA is introduced into genomic DNA of the primary, secondary, or immortalized cells at a pre-selected site. The targeting sequences used are determined by (selected with reference to) the site into which the exogenous DNA is to be inserted. The genomic P2T sequences provided by the present invention (ie., SEQ ID NO:1) are useful in these methods. The present invention further relates to homologously recombinant primary, secondary, or immortalized cells, referred to as homologously recombinant (HR) primary, secondary or immortalized cells, produced by the present method and to uses of the HR primary, secondary, or immortalized cells.

The present invention also relates to a method of activating (ie., turning on) a P2T gene present in primary, secondary, or immortalized cells of vertebrate origin, which is normally not expressed in the cells or is not expressed at physiologically significant levels in the cells as obtained. According to the present method, homologous recombination is used to replace or disable the regulatory region normally associated with the gene in cells as obtained with a regulatory sequence which causes the gene to be expressed at levels higher than evident in the corresponding nontransfected cell, or to display a pattern of regulation or induction that is different than evident in the corresponding nontransfected cell. The present invention, therefore, relates to a method of making proteins by turning on or activating an endogenous gene which encodes the desired product in transfected primary, secondary, or immortalized cells.

In one embodiment, the activated gene can be further amplified by the inclusion of a selectable marker gene which has the property that cells containing amplified copies of the selectable marker gene can be selected for by culturing the cells in the presence of the appropriate selectable agent. The activated endogenous gene which is near or linked to the amplified selectable marker gene will also be amplified in cells containing the amplified selectable marker gene. Cells containing many copies of the activated endogenous gene are useful for in vitro protein production and gene therapy.

In certain embodiments, the present invention relates also to methods for activating the expression of an endogenous gene in a cell or over-expressing an endogenous gene in a cell by non-homologous or random activation of gene expression (RAGE). The method comprises introducing a vector into the cell, allowing the vector to integrate into the genome of the cell by non-homologous recombination and allowing activation or over-expression of the endogenous gene in the cell. The use of non-homologous or "non-targeted" recombination does not require previous knowledge of the endogenous gene sequence. The methods for expression of endogenous genes via non-homologous recombination and preparing vector constructs for non-homologous recombination are described in International Patent Applications WO 99/15650 and WO 00/49162, both of which are incorporated in their entirety by reference.

Vector constructs useful in non-homologous recombination events should contain at least a transcriptional regulatory sequence operably linked to an unpaired splice donor sequence and one or more amplifiable markers. The transcriptional regulatory sequence is typically, but not limited to, a promoter sequence. The transcriptional regulatory sequence may further comprise an enhancer sequence, in addition to the promoter sequence. The transcriptional regulatory sequence is operatively linked to a translational start codon, a signal secretion sequence and an unpaired splice donor site. The transcriptional regulatory sequence may additionally be operatively linked to a translational start codon, an epitope tag and an unpaired splice donor site; or operatively linked to a translational start codon, a signal secretion sequence, an epitope tag and an unpaired splice donor site; or operatively linked to a translational start codon, a signal secretion sequence, an epitope tag, a sequence specific protease site and an unpaired splice donor site.

Examples of amplifiable markers that may be used in the above described vectors include, but are not limited to, dihydrofolate reductase (DHFR), neomycin resistance (neo), hypoxanthine phosphoribosyl transferase (HPRT), puromycin (pac), adenosine deaminase (ada), aspartate transcarbamylase (ATC), dihydro-orotase, histidine D (his D), multidrug resistance 1 (mdr 1), xanthine-guanine phosphoribosyl transferase (gpt), glutamine synthetase (GS) and carbamyl phosphate synthase (CAD). The vector could additionally comprise a screenable marker, such as a gene encoding a cell surface protein, a fluorescent protein and/or an enzyme. A signal secretion sequence may be included on the "activation" vector construct, such that the activated gene expression product is secreted.

The regulatory sequence of the vector construct can be a constitutive promoter, an inducible promoter or a tissue specific promoter or an enhancer. The use of an inducible promoter will permit low basal levels of activated protein to be produced by the cell during routine culturing and expansion. Subsequently, the cells may then be induced to express large amounts of the desired protein during production or screening. The regulatory sequence may be isolated from cellular or viral genomes. Examples of cellular regulatory sequences include, but are not limited to, the actin gene, metallothionein I gene, collagen gene, serum albumin gene and immunoglobulin genes. Examples of viral regulatory sequences include, but are not limited to, regulatory elements from *Cytomegalovirus* (CMV) immediate early gene, adenovirus late genes, SV40 genes, retroviral LTRs and *Herpesvirus* genes (see Tables 3 and 4 for additional tissue specific and inducible regulatory sequences, respectively).

Splicing of primary transcripts, the process by which introns are removed, is directed by a splice donor site and a splice acceptor site, located at the 5' and 3' ends introns, respectively. The consensus sequence for splice donor sites is (A/C)AGGURAGU (where R represents a purine nucleotide), with nucleotides (A/C)AG in positions 1–3 located in the exon and nucleotides GURAGU located in the intron.

An unpaired splice donor site is defined herein as a splice donor site present on the vector construct without a downstream splice acceptor site. When the vector is integrated by non-homologous recombination into the genome of a host cell, the unpaired splice donor site becomes paired with a splice acceptor site from an endogenous gene. The splice donor site from the vector construct, in conjunction with the splice acceptor site from the endogenous gene, will then direct the excision of all of the sequences between the vector splice donor site and the endogenous splice acceptor site. Excision of these intervening sequences removes sequences that interfere with translation of the endogenous protein.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Transcription-terminating regions are well known in the art. A preferred transcription-terminating region used in an adenovirus vector construct of the present invention comprises a polyadenylation signal of SV40 or the protamine gene.

TABLE 3

Tissue Specific Promoters

| PROMOTER | Target |
|---|---|
| Tyrosinase | Melanocytes |
| Tyrosinase Related Protein, TRP-1 | Melanocytes |
| Prostate Specific Antigen, PSA | Prostate Cancer |
| Albumin | Liver |
| Apolipoprotein | Liver |
| Plasminogen Activator Inhibitor Type-1, PAI-1 | Liver |
| Fatty Acid Binding | Colon Epithelial Cells |
| Insulin | Pancreatic Cells |
| Muscle Creatine Kinase, MCK | Muscle Cell |
| Myelin Basic Protein, MBP | Oligodendrocytes and Glial Cells |
| Glial Fibrillary Acidic Protein, GFAP | Glial Cells |
| Neural Specific Enolase | Nerve Cells |
| Immunoglobulin Heavy Chain | B-cells |
| Immunoglobulin Light Chain | B-cells, Activated T-cells |

TABLE 3-continued

Tissue Specific Promoters

| PROMOTER | Target |
| --- | --- |
| T-Cell Receptor | Lymphocytes |
| HLA DQα and DQβ | Lymphocytes |
| β-Interferon | Leukocytes; Lymphocytes Fibroblasts |
| Interlukin-2 | Activated T-cells |
| Platelet Derived Growth Factor | Erythrocytes |
| E2F-1 | Proliferating Cells |
| Cyclin A | Proliferating Cells |
| α-, β-Actin | Muscle Cells |
| Haemoglobin | Erythroid Cells |
| Elastase I | Pancreatic Cells |
| Neural Cell Adhesion Molecule, NCAM | Neural Cells |

TABLE 4

Inducible Promoters

| Promoter Element | Inducer |
| --- | --- |
| Early Growth Response-1 Gene, egr-1 | Radiation |
| Tissue Plasmingen Activator, t-PA | Radiation |
| fos and jun | Radiation |
| Multiple Drug Resistance Gene 1, mdr-1 | Chemotherapy |
| Heat Shock Proteins; hsp16, hs60, hps68, hsp70, | Heat |
| human Plasminogen Activator Inhibitor type-1, hPAI-1 | Tumor Necrosis Factor, TNF |
| Cytochrome P-450 CYP1A1 | Toxins |
| Metal-Responsive Element, MRE | Heavy Metals |
| Mouse Mammary Tumor Virus | Glucocorticoids |
| Collagenase | Phorbol Ester |
| Stromolysin | Phorbol Ester |
| SV40 | Phorbol Ester |
| Proliferin | Phorbol Ester |
| α-2-Macroglobulin | IL-6 |
| Murine MX Gene | Interferon, Newcastle Disease Virus |
| Vimectin | Serum |
| Thyroid Stimulating Hormone α Gene | Thyroid Hormone |
| HSP70 | Ela, SV40 Large T Antigen |
| Tumor Necrosis Factor | FMA |
| Interferon | Viral Infection, dsRNA |
| Somatostatin | Cylic AMP |
| Fibronectin | Cyclic AMP |

The cell expressing or over-expressing the gene of interest can be cultured in vitro under conditions favoring the production of the desired amounts of the expression product of the endogenous gene that has been activated or whose expression has been increased. A cell containing a vector construct which has been integrated into its genome may also be introduced into a eukaryote (e.g., a vertebrate, preferably a mammal, more preferably a human) under conditions favoring the activation or over-expression of the gene by the cell in vivo in the eukaryote. In particular embodiments, a genome-wide transcription library and protein expression library are generated (Harrington et al., 2001). Libraries are generated by random activation of gene expression (RAGE) using the above described vector constructs for non-homologous recombination.

Host cells can be derived from any eukaryotic species and can be primary, secondary, or immortalized. Furthermore, the cells can be derived from any tissue in the organism. Examples of useful tissues which cells can be isolated and activated include, but are not limited to, liver, spleen, kidney, bone marrow, thymus, heart, muscle, lung, brain, testes, ovary, islet, intestinal, skin, gall bladder, prostate, bladder and the immune hemapoietic systems.

The vector construct can be integrated into primary, secondary, or immortalized cells. Primary cells are cells that have been isolated from a vertebrate and have not been passaged. Secondary cells are primary cells that have been passaged, but are not immortalized. Immortalized cells are cell lines that can be passaged, apparently indefinitely. Examples of immortalized cell lines include, but are not limited to, HT1080, HeLa, Jurkat, 293 cells, KB carcinoma, T84 colonic epithelial cell line, Raji, Hep G2 or Hep 3B, hepatoma cell lines, A2058 melanoma, U937 lymphoma and WI38 fibroblast cell line, somatic cell hybrids and hybridomas.

Thus, to activate an endogenous gene of the present by non-homologous recombination, one would generate an "activation" vector construct comprising a regulatory sequence, one or more amplifiable markers, an epitope tag or a secretion signal sequence and an unpaired splice donor sequence. The activation construct is then introduced into a preferred eukaryotic host cell by any transfection method known in the art. Following introduction of the vector into the cell, the DNA is allowed to integrate into the host cell genome via non-homologous recombination. Integration can occur at spontaneous chromosome breaks or at artificially induced chromosomal beaks (e.g., γ irradiation, restriction enzymes). Following integration of the vector into the genome of the host cell, the genetic locus may be amplified in copy number by simultaneous or sequential selection for the one or more amplifiable markers located on the integrated vector construct. This approach facilitates the isolation of clones of cells that have amplified the locus containing the integrated vector. The cells containing the activated genes are isolated, sorted and the activated endogenous genes are isolated by PCR-based cloning (for a detailed experimental protocol, see International Application WO 99/15650, which is incorporated in its entirety by reference). One of ordinary skill in the art will appreciate, however, that any art-known method of cloning genes may be equivalently used to isolate activated genes from the sorted cells.

The invention further provides a recombinant expression vector comprising a DNA molecule encoding a P2T polypeptide cloned into the expression vector in an antisense orientation. That is, the DNA molecule is operatively linked to a regulatory sequence in a manner which allows for expression (by transcription of the DNA molecule) of an RNA molecule which is antisense to P2T mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, P2T polypeptide can be expressed in bacterial cells such as E coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation, infection or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. ("Molecular Cloning: A Laboratory Manual" 2nd ed, Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. A nucleic acid encoding a selectable marker can be introduced into a host cell on the same vector as that encoding the P2T polypeptide or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) P2T polypeptides. Accordingly, the invention further provides methods for producing P2T polypeptides using the host cells of the invention. In one embodiment, the method comprises culturing the host cell of invention (into which a recombinant expression vector encoding a P2T polypeptide has been introduced) in a suitable medium until the P2T polypeptide is produced. In another embodiment, the method further comprises isolating the P2T polypeptide from the medium or the host cell.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Transcription-terminating regions are well known in the art. A preferred transcription-terminating region used in an adenovirus vector construct of the present invention comprises a polyadenylation signal of SV40 or the protamine gene.

An expression vector comprises a polynucleotide that encodes a P2T polypeptide. Such a polypeptide is meant to include a sequence of nucleotide bases encoding a P2T polypeptide sufficient in length to distinguish said segment from a polynucleotide segment encoding a non-P2T polypeptide. A polypeptide of the invention can also encode biologically functional polypeptides or peptides which have variant amino acid sequences, such as with changes selected based on considerations such as the relative hydropathic score of the amino acids being exchanged. These variant sequences are those isolated from natural sources or induced in the sequences disclosed herein using a mutagenic procedure such as site-directed mutagenesis.

Preferably, the expression vectors of the present invention comprise polynucleotides that encode polypeptides comprising the amino acid residue sequence of SEQ ID NO:2. An expression vector can include a P2T polypeptide coding region itself of any of the P2T polypeptides noted above or it can contain coding regions bearing selected alterations or modifications in the basic coding region of such a P2T polypeptide. Alternatively, such vectors or fragments can code larger polypeptides or polypeptides which nevertheless include the basic coding region. In any event, it should be appreciated that due to codon redundancy as well as biological functional equivalence, this aspect of the invention is not limited to the particular DNA molecules corresponding to the polypeptide sequences noted above.

Exemplary vectors include the mammalian expression vectors of the pCMV family including pCMV6b and pCMV6c (Chiron Corp., Emeryville Calif.). In certain cases, and specifically in the case of these individual mammalian expression vectors, the resulting constructs can require co-transfection with a vector containing a selectable marker such as pSV2neo. Via co-transfection into a dihydrofolate reductase-deficient Chinese hamster ovary cell line, such as DG44, clones expressing P2T polypeptides by virtue of DNA incorporated into such expression vectors can be detected.

A DNA molecule, gene or polynucleotide of the present invention can be incorporated into a vector by a number of techniques which are well known in the art. For instance, the vector pUC18 has been demonstrated to be of particular value Likewise, the related vectors M13mp18 and M13mp19 can be used in certain embodiments of the invention, in particular, in performing dideoxy sequencing.

An expression vector of the present invention is useful both as a means for preparing quantities of the P2T polypeptide-encoding DNA itself, and as a means for preparing the encoded polypeptide and peptides. It is contemplated that where P2T polypeptides of the invention are made by recombinant means, one can employ either prokaryotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukaryotic P2T polypeptides are anticipated using the teaching of the disclosed invention, one likely expresses such sequences in eukaryotic hosts. However, even where the DNA segment encodes a eukaryotic P2T polypeptide, it is contemplated that prokaryotic expression can have some additional applicability. Therefore, the invention can be used in combination with vectors which can shuttle between the eukaryotic and prokaryotic cells. Such a system is described herein which allows the use of bacterial host cells as well as eukaryotic host cells.

Where expression of recombinant P2T polypeptides is desired and a eukaryotic host is contemplated, it is most desirable to employ a vector such as a plasmid, that incorporates a eukaryotic origin of replication. Additionally, for the purposes of expression in eukaryotic systems, one desires to position the P2T encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the P2T polypeptide, an appropriate polyadenylation site.

The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region of each plasmid. The pCMV4 vector differs from these four plasmids in containing a translation enhancer in the sequence prior to the polylinker. While they are not directly derived from the pCMV1–5 series of vectors, the functionally similar pCMV6b and c vectors are available from the Chiron Corp. (Emeryville, Calif.) and are identical except for the orientation of the polylinker region which is reversed in one relative to the other.

The universal components of the pCMV plasmids are as follows. The vector backbone is pTZ18R (Pharmacia), and contains a bacteriophage f1 origin of replication for production of single stranded DNA and an ampicillin-resistance gene. The CMV region consists of nucleotides −760 to +3 of the powerful promoter-regulatory region of the human cytomegalovirus (Towne stain) major immediate early gene (Thomsen et al., 1984; Boshart et al., 1985). The human growth hormone fragment (hGH) contains transcription termination and poly-adenylation signals representing sequences 1533 to 2157 of this gene (Seeburg, 1982). There is an Alu middle repetitive DNA sequence in this fragment. Finally, the SV40 origin of replication and early region promoter-enhancer derived from the pcD-X plasmid (HindII to PstI fragment) described in (Okayama et al., 1983). The promoter in this fragment is oriented such that transcription proceeds away from the CMV/hGH expression cassette.

The pCMV plasmids are distinguishable from each other by differences in the polylinker region and by the presence or absence of the translation enhancer. The starting pCMV1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from th CMV promoter was added C. The sequence acts as a translational enhancer by decreasing the requirements for initiation factors in polypeptide synthesis (Jobling et al., 1987; Browning et al., 1988). To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, GS alpha polypeptide, polypeptide phosphatase, synaptophysin, synapsin, insulin receptor, influenza hemagglutinin, androgen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites in pCMU that can cause spurious translation initiation. This codon should be avoided if possible in expression plasmids. A paper describing the construction and use of the parenteral pCMV1 and pCMV4 vectors has been published (Anderson et al., 1989b).

In yet another embodiment, the present invention provides recombinant host cells transformed, infected or transfected with polynucleotides that encode P2T polypeptides, as well as transgenic cells derived from those transformed or transfected cells. Preferably, the recombinant host cells of the present invention are transfected with a polynucleotide of SEQ ID NO:1. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook, Fritsch and Maniatis, 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the advantage of not exposing DNA to cellular compartments such as low-pH endosomes. Microinjection is therefore used primarily as a method to establish lines of cells that carry integrated copies of the DNA of interest.

The use of adenovirus as a vector for cell transfection is well known in the art. Adenovirus vector-mediated cell transfection has been reported for various cells (Stratford-Perricaudet, et al. 1992).

A transfected cell can be prokaryotic or eukaryotic. Preferably, the host cells of the invention are eukaryotic host cells. The recombinant host cells of the invention may be COS-1 cells. Where it is of interest to produce a human P2T polypeptide, cultured mammalian or human cells are of particular interest.

In another aspect, the recombinant host cells of the present invention are prokaryotic host cells. Preferably, the recombinant host cells of the invention are bacterial cells of the DH5 α strain of *Escherichia coli*. In general, prokaryotes are preferred for the initial cloning of DNA sequences and constructing the vectors useful in the invention. For example, *E. coli* K12 strains can be particularly useful. Other microbial strains which can be used include *E. coli* B, and *E. coli$_x$*1976 (ATCC No. 31537). These examples are, of course, intended to be illustrative rather than limiting.

Prokaryotes can also be used for expression. The aforementioned strains, as well as *E. coli* W3110 (ATCC No. 273325), *bacilli* such as *Bacillus subtilis*, or other enterobacteriaceae such as *Salmonella typhimurium* or *Serratia marcesans*, and various *Pseudomonas* species can be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species (Bolivar, et al. 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang, et al. 1978; Itakura., et al. 1977, Goeddel, et al. 1979; Goeddel, et al. 1980) and a tryptophan (TRP) promoter system (International Application No. EP 0036776; Siebwenlist et al. 1980). While these are the most commonly used, other microbial promoters have been discovered and utilized, and details concerning their nucleotide sequences have been published, enabling a skilled worker to introduce functional promoters into plasmid vectors (Siebwenlist, et al. 1980).

In addition to prokaryotes, eukaryotic microbes such as yeast can also be used. *Saccharomyces cerevisiase* or common bakers yeast is the most commonly used among eukaryotic microorganisms, although a number of other strains are commonly available. For expression in *Saccharomyces*, the plasmid YRp7, for example, is commonly used (Stinchcomb, et al. 1979; Kingsman, et al. 1979; Tschemper, et al. 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoter sequences in yeast vectors include the promoters for 3-phosphoglycerate kinase (Hitzeman., et al. 1980) or other glycolytic enzymes (Hess, et al. 1968; Holland, et al. 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years. Examples of such useful host cell lines are AtT-20, VERO and HeLa cells, Chinese hamster ovary (CHO) cell lines, and W138, BHK, COSM6, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication (Fiers, et al. 1978). Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication can be provided with by construction of the vector to include an exogenous origin, such as can be derived from SV40 or other viral (e.g., Polyoma, Adeno, VSV, BPV, CMV) source, or can be provided by the host cell chromosomal replication mechanism. If the vector is integrated into the host cell chromosome, the latter is often sufficient.

In yet another embodiment, the present invention contemplates a process or method of preparing P2T polypeptides comprising transfecting cells with a polynucleotide that encodes P2T polypeptides to produce transformed host cells, and maintaining the transformed host cells under biological conditions sufficient for expression of the polypeptide. Preferably, the transformed host cells are eukaryotic cells. Alternatively, the host cells are prokaryotic cells. More preferably, the prokaryotic cells are bacterial cells of the DH5-α strain of *Escherichia coli*. Even more preferably, the polynucleotide transfected into the transformed cells comprise the nucleic acid sequence of SEQ ID NO:1. Additionally, transfection is accomplished using an expression vector disclosed above.

A host cell used in the process is capable of expressing a functional, recombinant P2T polypeptide. A preferred host cell is a Chinese hamster ovary cell. However, a variety of cells are amenable to a process of the invention, for instance, yeast cells, human cell lines, and other eukaryotic cell lines known well to those of skill in the art.

Following transfection, the cell is maintained under culture conditions for a period of time sufficient for expression of a P2T receptor polypeptide. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C., more preferably from about 30° C. to about 40° C. and, even more preferably about 37° C.

pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded polypeptide are well known in the art.

Transfected cells are maintained for a period of time sufficient for expression of a P2T polypeptide. A suitable time depends inter alia upon the cell type used and is readily determinable by a skilled artisan. Typically, maintenance time is from about 2 to about 14 days.

Recombinant P2T polypeptide is recovered or collected either from the transfected cells or the medium in which those cells are cultured. Recovery comprises isolating and purifying the P2T polypeptide. Isolation and purification techniques for polypeptides are well known in the art and include such procedures as precipitation, filtration, chromatography, electrophoresis and the like.

E. P2T Antibodies

In another embodiment, the present invention provides antibodies immunoreactive with P2T polypeptides. Preferably, the antibodies of the invention are monoclonal antibodies. Additionally, the P2T polypeptides comprise the amino acid residue sequence of SEQ ID NO:2. Means for preparing and characterizing antibodies are well known in the art (see, e.g., Antibodies "A Laboratory Manual, E. Howell and D. Lane, Cold Spring Harbor Laboratory, 1988). In yet other embodiments, the present invention provides antibodies immunoreactive with P2T polynucleotides.

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier polypeptide are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used for the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal). The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with a P2T polypeptide comprising the steps of (a) transfecting recombinant host cells with a polynucleotide that encodes a P2T polypeptide; (b) culturing the host cells under conditions sufficient for expression of the polypeptide; (c) recovering the polypeptides; and (d) preparing the antibodies to the polypeptides. Preferably, the host cell is transfected with the polynucleotide of SEQ ID NO:1. Even more preferably, the present invention provides antibodies prepared according to the process described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, e.g., by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptide. The selected clones can then be propagated indefinitely to provide the monoclonal antibody.

By way of specific example, to produce an antibody of the present invention, mice are injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotid s from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

Additionally, examples of methods and reagents particularly amenable for use in generating and screening an antibody display library can be found in, for example, U.S. Pat. No. 5,223,409; International Application No. WO 92/18619; International Application No. WO 91/17271; International Application No. WO 92/20791; International Application No. WO 92/15679; International Application No. WO 93/01288; International Application No. WO 92/01047; International Application No. WO 92/09690; International Application No. WO 90/02809.

Additionally, recombinant anti-P2T antibodies, such as chimeric and humanized monoclonal antibodies, comprising both human and non-human fragments, which can be made using standard recombinant DNA techniques, are within the scope of the invention. Such chimeric and humanized monoclonal antibodies can be produced by recombinant DNA techniques known in the art, for example using methods described in U.S. Pat. No. 6,054,297; European Application Nos. EP 184,187; EP 171,496; EP 173,494; International Application No. WO 86/01533; U.S. Pat. No. 4,816,567; and European Application No. EP 125,023.

An anti-P2T antibody (e.g., monoclonal antibody) can be used to isolate P2T polypeptides by standard techniques, such as affinity chromatography or immunoprecipitation. An anti-P2T antibody can facilitate the purification of a natural P2T polypeptides from cells and recombinantly produced P2T polypeptide expressed in host cells. Moreover, an anti-P2T antibody can be used to detect P2T polypeptide (e.g., in a cellular lysate or cell supernatant) in order to evaluate the abundance and pattern of expression of the P2T polypeptide. The detection of circulating fragments of a P2T polypeptide can be used to identify P2T polypeptide turnover in a subject. Anti-P2T antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylarnine fluorescein, dansyl chloride or phycoerythrin; an example of a luminescent material includes luminol; examples of bioluminescent materials include luciferase, luciferin, and acquorin, and examples of suitable radioactive material include $^{125}$I, $^{131}$I, $^{15}$S or $^{3}$H.

F. Transgenic Animals

In certain preferred embodiments, the invention pertains to nonhuman animals with somatic and germ cells having a functional disruption of at least one, and more preferably both, alleles of an endogenous P2T gene of the present invention. Accordingly, the invention provides viable animals having a mutated P2T gene, and thus lacking P2T activity. These animals will produce substantially reduced amounts of a P2T in response to stimuli that produce normal amounts of a P2T in wild type control animals. The animals of the invention are useful, for example, as standard controls by which to evaluate P2T inhibitors, as recipients of a normal human P2T gene to thereby create a model system for screening human P2T inhibitors in vivo, and to identify disease states for treatment with P2T inhibitors. The animals are also useful as controls for studying the effect of ligands on P2T receptors.

In the transgenic nonhuman animal of the invention, the P2T gene preferably is disrupted by homologous recombination between the endogenous allele and a mutant P2T polynucleotide, or portion thereof, that has been introduced into an embryonic stem cell precursor of the animal. The embryonic stem cell precursor is then allowed to develop, resulting in an animal having a functionally disrupted P2T gene. As used herein, a "transgenic animal" is a non-human animal, preferably a mammal, more preferably a rodent such as a rat or mouse, in which one or more of the cells of the animal include a transgene. Other examples of transgenic animals include non-human primates, sheep, dogs, cows, goats, chickens, amphibians, and the like. The animal may have one P2T gene allele functionally disrupted (i.e., the animal may be heterozygous for the mutation), or more preferably, the animal has both P2T gene alleles functionally disrupted (ie., the animal can be homozygous for the mutation).

In one embodiment of the invention, functional disruption of both P2T gene alleles produces animals in which expression of the P2T gene product in cells of the animal is substantially absent relative to non-mutant animals. In another embodiment, the P2T gene alleles can be disrupted such that an altered (i.e., mutant) P2T gene product is produced in cells of the animal. A preferred nonhuman animal of the invention having a functionally disrupted P2T gene is a mouse. Given the essentially complete inactivation of P2T function in the homozygous animals of the invention and the about 50% inhibition of P2T function in the heterozygous animals of the invention, these animals are useful as positive controls against which to evaluate the effectiveness of P2T inhibitors. For example, a stimulus that normally induces production or activity of P2T can be administered to a wild type animal (i.e., an animal having a non-mutant P2T gene) in the presence of a P2T inhibitor to be tested and production or activity of P2T by the animal can be measured. The P2T response in the wild type animal can then be compared to the P2T response in the heterozygous and homozygous animals of the invention, similarly administered the P2T stimulus, to determine the percent of maximal P2T inhibition of the test inhibitor.

Additionally, the animals of the invention are useful for determining whether a particular disease condition involves the action of P2T and thus can be treated by a P2T inhibitor. For example, an attempt can be made to induce a disease condition in an animal of the invention having a functionally disrupted P2T gene. Subsequently, the susceptibility or resistance of the animal to the disease condition can be determined. A disease condition that is treatable with a P2T inhibitor can be identified based upon resistance of an animal of the invention to the disease condition. Another aspect of the invention pertains to a transgenic nonhuman animal having a functionally disrupted endogenous P2T gene but which also carries in its genome, and expresses, a transgene encoding a heterologous P2T (i.e., a P2T from another species). Preferably, the animal is a mouse and the heterologous P2T is a human P2T. An animal of the invention which has been reconstituted with human P2T can be used to identify agents that inhibit human P2T in vivo. For example, a stimulus that induces production and/or activity of P2T can be administered to the animal in the presence and absence of an agent to be tested and the P2T response in the animal can be measured. An agent that inhibits human P2T in vivo can be identified based upon a decreased P2T response in the presence of the agent compared to the P2T response in the absence of the agent. As used herein, a "transgene" is exogenous DNA which is integrated into the genome of a cell from which a transgenic animal develops and which remains in the genome of the mature animal, thereby directing the expression of an encoded gene product in one or more cell types or tissues of the transgenic animal.

Yet another aspect of the invention pertains to a polynucleotide construct for functionally disrupting a P2T gene in a host cell. The nucleic acid construct comprises: a) a nonhomologous replacement portion; b) a first homology region located upstream of the nonhomologous replacement portion, the first homology region having a nucleotide sequence with substantial identity to a first P2T gene sequence; and c) a second homology region located downstream of the nonhomologous replacement portion, the second homology region having a nucleotide sequence with substantial identity to a second P2T gene sequence, the second P2T gene sequence having a location downstream of the first P2T gene sequence in a naturally occurring endogenous P2T gene. Additionally, the first and second homology regions are of sufficient length for homologous recombination between the nucleic acid construct and an endogenous P2T gene in a host cell when the nucleic acid molecule is introduced into the host cell. As used herein, a "homologous recombinant animal" is a non-human animal, preferably a mammal, more preferably a mouse, in which an endogenous P2T gene has been altered by homologous recombination between the endogenous gene and an exogenous DNA molecule introduced into a cell of the animal, e.g., an embryonic cell of the animal, prior to development of the animal.

In a preferred embodiment, the nonhomologous replacement portion comprises a positive selection expression cassette, preferably including a neomycin phosphotransferase gene operatively linked to a regulatory element(s). In another preferred embodiment, the nucleic acid construct also includes a negative selection expression cassette distal to either the upstream or downstream homology regions. A preferred negative selection cassette includes a herpes simplex virus thymidine kinase gene operatively linked to a regulatory element(s). Another aspect of the invention pertains to recombinant vectors into which the nucleic acid construct of the invention has been incorporated.

Yet another aspect of the invention pertains to host cells into which the nucleic acid construct of the invention has been introduced to thereby allow homologous recombination between the nucleic acid construct and an endogenous P2T gene of the host cell, resulting in functional disruption of the endogenous P2T gene. The host cell can be a mammalian cell that normally expresses P2T, such as a human neuron, or a pluripotent cell, such as a mouse embryonic stem cell. Further development of an embryonic stem cell into which the nucleic acid construct has been introduced and homologously recombined with the endogenous P2T gene produces a transgenic nonhuman animal having cells that are descendant from the embryonic stem cell and thus carry the P2T gene disruption in their genome. Animals that carry the P2T gene disruption in their germline can then be selected and bred to produce animals having the P2T gene disruption in all somatic and germ cells. Such mice can then be bred to homozygosity for the P2T gene disruption.

It is contemplated that in some instances the genome of a transgenic animal of the present invention will have been altered through the stable introduction of one or more of the P2T polynucleotide compositions described herein, either native, synthetically modified or mutated. As described herein, "transgenic animal" refers to any animal, preferably a non-human mammal (e.g. mouse, rat, rabbit, squirrel, hamster, rabbits, guinea pigs, pigs, micro-pigs, prairie dogs, baboons, squirrel monkeys and chimpanzees, etc.), a bird or an amphibian, in which one or more cells contain heterologous nucleic acid introduced by way of human intervention, such as by transgenic techniques well known in the art. The nucleic acid is introduced into the cell, directly or indirectly, by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA.

The host cells of the invention can also be used to produce non-human transgenic animals. The non-human transgenic animals can be used in screening assays designed to identify agents or compounds, e.g., drugs, pharmaceuticals, etc., which are capable of ameliorating detrimental symptoms of selected disorders such as nervous system disorders, e.g., psychiatric disorders or disorders affecting circadian rhythms and the sleep-wake cycle. For example, in one embodiment, a host cell of the invention is a fertilized oocyte or an embryonic stem cell into which P2T polypeptide-coding sequences have been introduced. Such host cells can then be used to create non-human transgenic animals in which exogenous P2T gene sequences have been introduced into their genome or homologous recombinant animals in which endogenous P2T gene sequences have been altered. Such animals are useful for studying the function and/or activity of a P2T polypeptide and for identifying and/or evaluating modulators of P2T polypeptide activity.

A transgenic animal of the invention can be created by introducing P2T polypeptide encoding nucleic acid into the male pronuclei of a fertilized oocyte, e.g., by microinjection, retroviral infection, and allowing the oocyte to develop in a pseudopregnant female foster animal. The murine P2T cDNA sequence of SEQ ID NO:1 can be introduced as a transgene into the genome of a non-human animal.

Moreover, a non-human homologue of the murine P2T gene, such as a rabbit P2T gene, can be isolated based on hybridization to the murine P2T cDNA (described above) and used as a transgene. Intronic sequences and polyadenylation signals can also be included in the transgene to increase the efficiency of expression of the transgene. A tissue-specific regulatory sequence(s) can be operably linked to the P2T transgene to direct expression of a P2T polypeptide to particular cells. Methods for generating transgenic animals via embryo manipulation and microinjection, particularly animals such as mice, have become conventional in the art and are described, for example, in U.S. Pat. Nos. 4,736,866, 4,870,009, and U.S. Pat. No. 4,873,191, and in Hogan, 1986. Similar methods are used for production of other transgenic animals. A transgenic founder animal can be identified based upon the presence of the P2T transgene in its genome and/or expression of P2T mRNA in tissues or cells of the animals. A transgenic founder animal can then be used to breed additional animals carrying the transgene. Moreover, transgenic animals carrying a transgene encoding a P2T polypeptide can further be bred to other transgenic animals carrying other transgenes.

To create a homologous recombinant animal, a vector is prepared which contains at least a fragment of a P2T gene into which a deletion, addition or substitution has been introduced to thereby alter, e.g., functionally disrupt, the P2T gene. The P2T gene is preferably a mouse gene (e.g., SEQ ID NO:1). The mouse P2T gene then can be used to construct a homologous recombination vector suitable for altering an endogenous P2T gene in the mouse genome. In a preferred embodiment, the vector is designed such that, upon homologous recombination, the endogenous P2T gene is functionally disrupted (i.e., no longer encodes a functional protein; also referred to as a "knock out" vector).

Alternatively, the vector can be designed such that, upon homologous recombination, the endogenous P2T gene is mutated or otherwise altered but still encodes functional protein (e.g., the upstream regulatory region can be altered to thereby alter the expression of the endogenous P2T polypeptide). In the homologous recombination vector, the altered fragment of the P2T gene is flanked at its 5' and 3' ends by additional nucleic acid of the P2T gene to allow for homologous recombination to occur between the exogenous P2T gene carried by the vector and an endogenous P2T gene in an embryonic stem cell. The additional flanking P2T nucleic acid is of sufficient length for successful homologous recombination with the endogenous gene.

Typically, several kilobases of flanking DNA (both at the 5' and 3' ends) are included in the vector (see e.g., Thomas and Capecchi, 1987, for a description of homologous recombination vectors). The vector is introduced into an embryonic stem cell line (e.g., by electroporation) and cells in which the introduced P2T gene has homologously recombined with the endogenous P2T gene are selected (see e.g., Li et al., 1992). The selected cells are then injected into a blastocyst of an animal (e.g., a mouse) to form aggregation chimeras (see e.g., Bradley, 1987, pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, 1991; and in PCT International Publication Nos. WO 90/11354; WO 91/01140; WO 92/0968; and WO 93/04169.

In another embodiment, transgenic non-human animals can be produced which contain selected systems which allow for regulated expression of the transgene. One example of such a system is the cre/loxP recombinase system of bacteriophage PL. For a description of the cre/loxP recombinase system, see, e.g., Lakso et al., 1992. Another example of a recombinase system is the FLP recombinase system of *Saccharomyces cerevisiae* (O'Gonnan et al., 1991). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al., 1997, and PCT International Application Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

G. Uses and Methods of the Invention

The nucleic acid molecules, polypeptides, polypeptide homologues, modulators, and antibodies described herein can be used in one or more of the following methods: a) drug screening assays; b) diagnostic assays particularly in disease identification, allelic screening and pharmacogenetic testing; c) methods of treatment; d) pharmacogenomics; and e) monitoring of effects during clinical trials. A P2T polypeptide of the invention can be used as a drug target for developing agents to modulate the activity of the P2T polypeptide. The isolated nucleic acid molecules of the invention can be used to express P2T polypeptide (e.g., via a recombinant expression vector in a host cell or in gene therapy applications), to detect P2T mRNA (e.g., in a biological sample) or a naturally occurring or recombinantly generated genetic mutation in a P2T gene, and to modulate P2T polypeptide activity, as described further below. In addition, the P2T polypeptides can be used to screen drugs or compounds which modulate P2T polypeptide activity. Moreover, the anti-P2T antibodies of the invention can be used to detect and isolate a P2T polypeptide, particularly fragments of a P2T polypeptides present in a biological sample, and to modulate P2T polypeptide activity.

Drug Screening Assays

The invention provides methods for identifying compounds or agents that can be used to treat disorders characterized by (or associated with) aberrant or abnormal P2T nucleic acid expression and/or P2T polypeptide activity. These methods are also referred to herein as drug screening assays and typically include the step of screening a candidate/test compound or agent to identify compounds that are an agonist or antagonist of a P2T polypeptide, and specifically for the ability to interact with (e.g., bind to) a P2T polypeptide, to modulate the interaction of a P2T polypeptide and a target molecule, and/or to modulate P2T nucleic acid expression and/or P2T polypeptide activity. Candidate/test compounds or agents which have one or more of these abilities can be used as drugs to treat disorders characterized by aberrant or abnormal P2T nucleic acid expression and/or P2T polypeptide activity. Candidate/test compounds include, for example, 1) peptides such as soluble peptides, including Ig-tailed fusion peptides and members of random peptide libraries and combinatorial chemistry-derived molecular libraries made of D- and/or L-configuration amino acids; 2) phosphopeptides (e.g., members of random and partially degenerate, directed phosphopeptide libraries, see, e.g., Songyang et al., 1993; 3) antibodies (e.g., polyclonal, monoclonal, humanized, anti-idiotypic, chimeric, and single chain antibodies as well as Fab, F(ab')2, Fab expression library fragments, and epitope-binding fragments of antibodies); and 4) small organic and inorganic molecules (e.g., molecules obtained from combinatorial and natural product libraries). In one embodiment, the invention provides assays for screening candidate/test compounds which interact with (e.g., bind to) a P2T polypeptide. Typically, the assays are recombinant cell based or cell-free assays which include the steps of combining a cell expressing a P2T polypeptide or a bioactive fragment thereof, or an isolated P2T polypeptide, and a candidate/test compound, e.g., under conditions which allow for interaction of (e.g., binding of) the candidate/test compound to the P2T polypeptide or fragment thereof to form a complex, and detecting the formation of a complex, in which the ability of the candidate compound to interact with (e.g., bind to) the P2T polypeptide or fragment thereof is indicated by the presence of the candidate compound in the complex. Formation of complexes between the P2T polypeptide and the candidate compound can be detected using competition binding assays, and can be quantitated, for example, using standard immunoassays.

In another embodiment, the invention provides screening assays to identify candidate/test compounds which modulate (e.g., stimulate or inhibit) the interaction (and most likely P2T polypeptide activity as well) between a P2T polypeptide and a molecule (target molecule) with which the P2T polypeptide normally interacts. Examples of such target molecules include proteins in the same signaling path as the P2T polypeptide, e.g., proteins which may function upstream (including both stimulators and inhibitors of activity) or downstream of the P2T polypeptide in, for example, a cognitive function signaling pathway or in a pathway involving P2T polypeptide activity, e.g., a G protein or other interactor involved in cAMP or phosphatidylinositol turnover, and/or adenylate cyclase or phospholipase C activation. Typically, the assays are recombinant cell based assays which include the steps of combining a cell expressing a P2T polypeptide, or a bioactive fragment thereof, a P2T polypeptide target molecule (e.g., a P2T ligand) and a candidate/test compound, e.g., under conditions wherein but for the presence of the candidate compound, the P2T polypeptide or biologically active fragment thereof interacts with (e.g., binds to) the target molecule, and detecting the formation of a complex which includes the P2T polypeptide and the target molecule or detecting the interaction/reaction of the P2T polypeptide and the target molecule.

Detection of complex formation can include direct quantitation of the complex by, for example, measuring inductive effects of the P2T polypeptide. A statistically significant change, such as a decrease, in the interaction of the P2T polypeptide and target molecule (e.g., in the formation of a complex between the P2T polypeptide and the target molecule) in the presence of a candidate compound (relative to what is detected in the absence of the candidate compound) is indicative of a modulation (e.g., stimulation or inhibition) of the interaction between the P2T polypeptide and the target molecule. Modulation of the formation of complexes between the P2T polypeptide and the target molecule can be quantitated using, for example, an immunoassay.

To perform cell free drug screening assays, it is desirable to immobilize either the P2T polypeptide or its target molecule to facilitate separation of complexes from uncomplexed forms of one or both of the proteins, as well as to accommodate automation of the assay. Interaction (e.g., binding of) of the P2T polypeptide to a target molecule, in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows the protein to be bound to a matrix. For example, glutathione-S-transferase/P2T fusion proteins can be adsorbed onto glutathione sepharose beads (Sigma Chemical, St. Louis, Mo.) or glutathione derivatized microtitre plates, which are then combined with the cell lysates (e.g., $^{35}$S labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of P2T-binding protein found in the bead fraction quantitated from the gel using standard electrophoretic techniques.

Other techniques for immobilizing proteins on matrices can also be used in the drug screening assays of the invention. For example, either the P2T polypeptide or its target molecule can be immobilized utilizing conjugation of biotin and streptavidin. Biotinylated P2T polypeptide molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with a P2T polypeptide but which do not interfere with binding of the protein to its target molecule can be derivatized to the wells of the plate, and P2T polypeptide trapped in the wells by antibody conjugation. As described above, preparations of a P2T-binding protein and a candidate compound are incubated in the P2T polypeptide-presenting wells of the plate, and the amount of complex trapped in the well can be quantitated. Methods for detecting such complexes, in addition to those described above for the GST-immobilized complexes, include immunodetection of complexes using antibodies reactive with the P2T polypeptide target molecule, or which are reactive with P2T polypeptide and compete with the target molecule; as well as enzyme-linked assays which rely on detecting an enzymatic activity associated with the target molecule.

In yet another embodiment, the invention provides a method for identifying a compound (e.g., a screening assay) capable of use in the treatment of a disorder characterized by (or associated with) aberrant or abnormal P2T nucleic acid expression or P2T polypeptide activity. This method typically includes the step of assaying the ability of the compound or agent to modulate the expression of the P2T nucleic acid or the activity of the P2T polypeptide thereby identifying a compound for treating a disorder characterized by aberrant or abnormal P2T nucleic acid expression or P2T polypeptide activity. Methods for assaying the ability of the compound or agent to modulate the expression of the P2T nucleic acid or activity of the P2T polypeptide are typically cell-based assays. For example, cells which are sensitive to ligands which transduce signals via a pathway involving a P2T polypeptide can be induced to overexpress a P2T polypeptide in the presence and absence of a candidate compound.

Candidate compounds which produce a statistically significant change in P2T polypeptide-dependent responses (either stimulation or inhibition) can be identified. In one embodiment, expression of the P2T nucleic acid or activity of a P2T polypeptide is modulated in cells and the effects of candidate compounds on the readout of interest (such as cAMP or phosphatidylinositol turnover) are measured. For example, the expression of genes which are up- or down-regulated in response to a P2T polypeptide-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of a P2T polypeptide or P2T polypeptide target molecules can also be measured, for example, by immunoblotting.

Alternatively, modulators of P2T gene expression (e.g., compounds which can be used to treat a disorder characterized by aberrant or abnormal P2T nucleic acid expression or P2T polypeptide activity) can be identified in a method wherein a cell is contacted with a candidate compound and the expression of P2T mRNA or protein in the cell is determined. The level of expression of P2T mRNA or protein in the presence of the candidate compound is compared to the level of expression of P2T mRNA or protein in the absence of the candidate compound. The candidate compound can then be identified as a modulator of P2T nucleic acid expression based on this comparison and be used to treat a disorder characterized by aberrant P2T nucleic acid expression. For example, when expression of P2T mRNA or protein is greater (statistically significantly greater) in the presence of the candidate compound than in its absence, the candidate compound is identified as a stimulator of P2T nucleic acid expression. Alternatively, when P2T nucleic acid expression is less (statistically significantly less) in the presence of the candidate compound than in its absence, the candidate compound is identified as an inhibitor of P2T nucleic acid expression. The level of P2T nucleic acid expression in the cells can be determined by methods described herein for detecting P2T mRNA or protein.

In certain aspects of the invention, P2T polypeptides or portions thereof can be used as "bait proteins" in a two-hybrid assay or three-hybrid assay (see, e.g., U.S. Pat. No. 5,283,317; U.S. Statutory Invention Registration No. H1,892; Zervos et al., 1993; Madura et al., 1993; Bartel et al., 1993(a); Iwabuchi et al., 1993; International Application No. WO94/10300), to identify other proteins, which bind to or interact with P2T ("P2T-binding proteins" or "P2T-bp") and are involved in P2T activity. Such P2T-binding proteins are also likely to be involved in the propagation of signals by the P2T polypeptides or P2T targets as, for example, downstream elements of a P2T-mediated signaling pathway. Alternatively, such P2T-binding proteins may be P2T inhibitors.

Thus, in certain embodiments, the invention contemplates determining protein:protein interactions, e.g., P2T and a P2T binding protein. The yeast two-hybrid system is extremely useful for studying protein:protein interactions. Variations of the system are available for screening yeast phagemid (Harper et al., 1993; Elledge et al., 1991) or plasmid (Bartel et al., 1993(a),(b); Finley and Brent, 1994) cDNA libraries to clone interacting proteins, as well as for studying known protein pairs. Recently, a two-hybrid method for high volume screening for specific inhibitors of protein:protein interactions and a two-hybrid screen that identifies many different interactions between protein pairs at once have been described (see, U.S. Statutory Invention Registration No. H1,892).

The success of the two-hybrid system relies upon the fact that the DNA binding and polymerase activation domains of many transcription factors, such as GAL4, can be separated and then rejoined to restore functionality (Morin et al., 1993). Briefly, the assay utilizes two different DNA constructs. In one construct, the gene that codes for a P2T polypeptide is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a P2T-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the P2T polypeptide.

Modulators of P2T polypeptide activity and/or P2T nucleic acid expression identified according to these drug screening assays can be used to treat, for example, nervous system disorders. These methods of treatment include the steps of administering the modulators of P2T polypeptide activity and/or nucleic acid expression, e.g., in a pharmaceutical composition as described herein, to a subject in need of such treatment, e.g., a subject with a disorder described herein.

Diagnostic Assays

The invention further provides a method for detecting the presence of a P2T polypeptide or P2T nucleic acid molecule, or fragment thereof, in a biological sample. The method involves contacting the biological sample with a compound or an agent capable of detecting P2T polypeptide or mRNA such that the presence of P2T polypeptide/encoding nucleic acid molecule is detected in the biological sample. A preferred agent for detecting P2T mRNA is a labeled or labelable nucleic acid probe capable of hybridizing to P2T mRNA. The nucleic acid probe can be, for example, the full-length P2T cDNA of SEQ ID NO: 1, or a fragment thereof, such as an oligonucleotide of at least 15, 30, 50, 100, 250 or 500 nucleotides in length and sufficient to specifically hybridize under stringent conditions to P2T mRNA. A preferred agent for detecting P2T polypeptide is a labeled or labelable antibody capable of binding to P2T polypeptide. Antibodies can be polycolonal, or more preferably, monoclonal. An intact antibody, or a fragment thereof (e.g., Fab or F(ab')2) can be used. The term "labeled or labelable," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect P2T mRNA or protein in a biological sample in vitro as well as in vivo. For example, in vitro techniques for detection of P2T mRNA include Northern hybridizations and in situ hybridizations. In vitro techniques for detection of P2T polypeptide include enzyme linked immunosorbent assays (ELISAs), Western blots, immunoprecipitations and immunofluorescence. Alternatively, P2T polypeptide can be detected in vivo in a subject by introducing into the subject a labeled anti-P2T antibody. For example, the antibody can be labeled with a radioactive marker whose presence and location in a subject can be detected by standard imaging techniques. Particularly useful are methods which detect the allelic variant of a P2T polypeptide expressed in a subject and methods which detect fragments of a P2T polypeptide in a sample.

The invention also encompasses kits for detecting the presence of a P2T polypeptide in a biological sample. For example, the kit can comprise reagents such as a labeled or labelable compound or agent capable of detecting P2T polypeptide or mRNA in a biological sample; means for determining the amount of P2T polypeptide in the sample; and means for comparing the amount of P2T polypeptide in the sample with a standard. The compound or agent can be packaged in a suitable container. The kit can further comprise instructions for using the kit to detect P2T mRNA or protein.

The methods of the invention can also be used to detect naturally occurring genetic mutations in a P2T gene, thereby determining if a subject with the mutated gene is at risk for a disorder characterized by aberrant or abnormal P2T nucleic acid expression or P2T polypeptide activity as described herein. In preferred embodiments, the methods include detecting, in a sample of cells from the subject, the presence or absence of a genetic mutation characterized by at least one of an alteration affecting the integrity of a gene encoding a P2T polypeptide, or the misexpression of the P2T gene. For example, such genetic mutations can be detected by ascertaining the existence of at least one of 1) a deletion of one or more nucleotides from a P2T gene; 2) an addition of one or more nucleotides to a P2T gene; 3) a substitution of one or more nucleotides of a P2T gene, 4) a chromosomal rearrangement of a P2T gene; 5) an alteration in the level of a messenger RNA transcript of a P2T gene, 6) aberrant modification of a P2T gene, such as of the methylation pattern of the genomic DNA, 7) the presence of a non-wild type splicing pattern of a messenger RNA transcript of a P2T gene, 8) a non-wild type level of a P2T-protein, 9) allelic loss of a P2T gene, and 10) inappropriate post-translational modification of a P2T-protein. As described herein, there are a large number of assay techniques known in the art that can be used for detecting mutations in a P2T gene.

In certain embodiments, detection of the mutation involves the use of a probe/primer in a polymerase chain reaction (PCR) (see, e.g. U.S. Pat. No. 4,683,195 and U.S. Pat. No. 4,683,202), such as anchor PCR or RACE PCR, or, alternatively, in a ligation chain reaction (LCR), the latter of which can be particularly useful for detecting point mutations in the P2T-gene (see Abravaya et al, 1995). This method can include the steps of collecting a sample of cells from a patient, isolating nucleic acid (e.g., genomic, mRNA or both) from the cells of the sample, contacting the nucleic acid sample with one or more primers which specifically hybridize to a P2T gene under conditions such that hybridization and amplification of the P2T-gene (if present) occurs, and detecting the presence or absence of an amplification product, or detecting the size of the amplification product and comparing the length to a control sample.

In an alternative embodiment, mutations in a P2T gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see U.S. Pat. No. 5,498,531 hereby incorporated by reference in its entirety) can be used to score for the presence of specific mutations by development or loss of a ribozyme cleavage site.

In yet another embodiment, any of a variety of sequencing reactions known in the art can be used to directly sequence the P2T gene and detect mutations by comparing the sequence of the sample P2T gene with the corresponding wild-type (control) sequence. Examples of sequencing reactions include those based on techniques developed by Maxim and Gilbert (1977) or Sanger (1977). A variety of automated sequencing procedures can be utilized when performing the diagnostic assays, including sequencing by mass spectrometry (see, e.g., International Application No. WO 94/16101; Cohen et al., 1996; and Griffin et al. 1993).

Other methods for detecting mutations in the P2T gene include methods in which protection from cleavage agents is used to detect mismatched bases in RNA/RNA or RNA/DNA duplexes (Myers et al., 1985; Cotton et al., 1988; Saleeba et al., 1992), electrophoretic mobility of mutant and wild type nucleic acid is compared (Orita et al., 1989; Cotton, 1993; and Hayashi, 1992), and movement of mutant or wild-type fragments in polyacrylamide gels containing a gradient of denaturant is assayed using denaturing gradient gel electrophoresis (Myers et al., 1985). Examples of other techniques for detecting point mutations include selective oligonucleotide hybridization, selective amplification, and selective primer extension.

Methods of Treatment

Another aspect of the invention pertains to methods for treating a subject, e.g., a human, having a disease or disorder characterized by (or associated with) aberrant or abnormal P2T nucleic acid expression and/or P2T polypeptide activity. These methods include the step of administering a P2T polypeptide/gene modulator (agonist or antagonist) to the subject such that treatment occurs. The language "aberrant or abnormal P2T polypeptide expression" refers to expression of a non-wild-type P2T polypeptide or a non-wild-type level of expression of a P2T polypeptide. Aberrant or abnormal P2T polypeptide activity refers to a non-wild-type P2T polypeptide activity or a non-wild-type level of P2T polypeptide activity. As the P2T polypeptide is involved in a pathway involving signaling within cells, aberrant or abnormal P2T polypeptide activity or expression interferes with the normal regulation of functions mediated by P2T polypeptide signaling. The terms "treating" or "treatment," as used herein, refer to reduction or alleviation of at least one adverse effect or symptom of a disorder or disease, e.g., a disorder or disease characterized by or associated with abnormal or aberrant P2T polypeptide activity or P2T nucleic acid expression.

As used herein, a P2T polypeptide/gene modulator is a molecule which can modulate P2T nucleic acid expression and/or P2T polypeptide activity. For example, a P2T gene or protein modulator can modulate, e.g., upregulate (activate/agonize) or downregulate (suppress/antagonize), P2T nucleic acid expression. In another example, a P2T polypeptide/gene modulator can modulate (e.g., stimulate/agonize or inhibit/antagonize) P2T polypeptide activity. If it is desirable to treat a disorder or disease characterized by (or associated with) aberrant or abnormal (non-wild-type) P2T nucleic acid expression and/or P2T polypeptide activity by inhibiting P2T nucleic acid expression, a P2T modulator can be an antisense molecule, e.g., a ribozyme, as described herein. Examples of antisense molecules which can be used to inhibit P2T nucleic acid expression include antisense molecules which are complementary to a fragment of the 5' untranslated region of SEQ ID NO: 1, which also includes the start codon and antisense molecules which are complementary to a fragment of a 3' untranslated region of SEQ ID NO: 1.

A P2T modulator that inhibits P2T nucleic acid expression can also be a small molecule or other drug, e.g., a small molecule or drug identified using the screening assays described herein, which inhibits P2T nucleic acid expression. If it is desirable to treat a disease or disorder characterized by (or associated with) aberrant or abnormal (non-wild-type) P2T nucleic acid expression and/or P2T polypeptide activity by stimulating P2T nucleic acid expression, a P2T modulator can be, for example, a nucleic acid molecule encoding a P2T polypeptide (e.g., a nucleic acid molecule comprising a nucleotide sequence homologous to the nucleotide sequence of SEQ ID NO: 1 or a small molecule or other drug, e.g., a small molecule (peptide) or drug identified using the screening assays described herein, which stimulates P2T nucleic acid expression.

Alternatively, if it is desirable to treat a disease or disorder characterized by (or associated with) aberrant or abnormal (non-wild-type) P2T nucleic acid expression and/or P2T polypeptide activity by inhibiting P2T polypeptide activity, a P2T modulator can be an anti-P2T antibody or a small molecule or other drug, e.g., a small molecule or drug identified using the screening assays described herein, which inhibits P2T polypeptide activity. If it is desirable to treat a disease or disorder characterized by (or associated with) aberrant or abnormal (non-wild-type) P2T nucleic acid expression and/or P2T polypeptide activity by stimulating P2T polypeptide activity, a P2T modulator can be an active P2T polypeptide or fragment thereof (e.g., a P2T polypeptide or fragment thereof having an amino acid sequence which is homologous to the amino acid sequence of SEQ ID NO:2 or a fragment thereof) or a small molecule or other drug, e.g., a small molecule or drug identified using the screening assays described herein, which stimulates P2T polypeptide activity.

Other aspects of the invention pertain to methods for modulating a P2T polypeptide mediated cell activity. These methods include contacting the cell with an agent (or a composition which includes an effective amount of an agent) which modulates P2T polypeptide activity or P2T nucleic acid expression such that a P2T polypeptide mediated cell activity is altered relative to normal levels (for example, cAMP or phosphatidylinositol metabolism). As used herein, "a P2T polypeptide mediated cell activity" refers to a normal or abnormal activity or function of a cell. Examples of P2T polypeptide mediated cell activities include phosphatidylinositol turnover, production or secretion of molecules, such as proteins, contraction, proliferation, migration, differentiation, and cell survival. The term "altered" as used herein refers to a change, e.g., an increase or decrease, of a cell associated activity particularly cAMP or phosphatidylinositol turnover, and adenylate cyclase or phospholipase C activation.

In one embodiment, the agent stimulates P2T polypeptide activity or P2T nucleic acid expression. In another embodiment, the agent inhibits P2T polypeptide activity or P2T nucleic acid expression. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject, e.g., a mammal, e.g., a human, and the subject has a disorder or disease characterized by or associated with abnormal or aberrant P2T polypeptide activity or P2T nucleic acid expression.

A nucleic acid molecule, a protein, a P2T modulator, a compound etc. used in the methods of treatment can be incorporated into an appropriate pharmaceutical composition described below and administered to the subject through a route which allows the molecule, protein, modulator, or compound etc. to perform its intended function.

A modulator of P2T polynucleotide expression and/or P2T polypeptide activity may be used in the treatment of various diseases or disorders including, but not limited to, the cardiopulmonary system such as acute heart failure, hypotension, hypertension, angina pectoris, myocardial infarction and the like; the gastrointestinal system; the central nervous system; kidney diseases; liver diseases; hyperproliferative diseases, such as cancers and psoriasis; apoptotic diseases; pain; endometriosis; anorexia; bulimia; asthma; osteoporosis; neuropsychiatric disorders such as schizophrenia, delirium, bipolar, depression, anxiety, panic disorders; urinary retention; ulcers; allergies; benign prostatic hypertrophy; and dyskinesias, such as Huntington's disease or Gilles dela Tourett's syndrome Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicella-zoster virus (Herpes zoster), cytomegalovirus, poliomyelitis, rabies, and human immunodeficiency virus 1, including FHV-I meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degenration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Elizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin Bl) deficiency and vitamin B12 deficiency, neurologic sequelae of metabolic disturbances, including hypoglycemia, hyperglycemia, and hepatic encephalopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), neurocutaneous syndromes (phakomatoses), including neurofibromotosis, including Type I neurofibromatosis (NFI) and TYPE 2 neurotibromatosis (NF2), tuberous sclerosis, and Von Hippel-Lindau disease, and neuropsychiatric disorders, such as schizophrenia, bipolar, depression, anxiety and panic disorders.

Pharmacogenomics

Test/candidate compounds, or modulators which have a stimulatory or inhibitory effect on P2T polypeptide activity (e.g., P2T gene expression) as identified by a screening assay described herein can be administered to individuals to treat (prophylactically or therapeutically) disorders (e.g., neurological disorders) associated with aberrant P2T polypeptide activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permit the selection of effective compounds (e.g., drugs) for prophylactic or therapeutic treatments based on a consideration of the individual's genotype. Such pharmacogenomics can further be used to determine appropriate dosages and therapeutic regimens. Accordingly, the activity of P2T polypeptide, expression of P2T nucleic acid, or mutation content of P2T genes in an individual can be determined to thereby select appropriate compound(s) for therapeutic or prophylactic treatment of the individual.

Pharmacogenomics deal with clinically significant hereditary variations in the response to drugs due to altered drug disposition and abnormal action in affected persons. See, e.g., Eichelbaum, 1996 and Linder, 1997. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (GOD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2136 and CYP2C 19) has provided an explanation as to why some patients do not obtain the expected drug effects or show exaggerated drug response and serious toxicity after taking the standard and safe dose of a drug.

These polymorphisms are expressed in two phenotypes in the population, the extensive metabolizer (EM) and poor metabolizer (PM). The prevalence of PM is different among different populations. For example, the gene coding for CYP2136 is highly polymorphic and several mutations have been identified in PM, which all lead to the absence of functional CYP2D6. Poor metabolizers of CYP2136 and CYP2C 19 quite frequently experience exaggerated drug response and side effects when they receive standard doses.

If a metabolite is the active therapeutic moiety, PM shows no therapeutic response, as demonstrated for the analgesic effect of codeine mediated by its CYP2136-formed metabolite morphine. The other extreme is the so called ultra-rapid metabolizers who do not respond to standard doses. Recently, the molecular basis of ultra-rapid metabolism has been identified to be due to CYP2D6 gene amplification.

Thus, the activity of P2T polypeptide, expression of P2T nucleic acid, or mutation content of P2T genes in an individual can be determined to thereby select appropriate agent(s) for therapeutic or prophylactic treatment of a subject. In addition, pharmacogenetic studies can be used to apply genotyping of polymorphic alleles encoding drug-metabolizing enzymes to the identification of a subject's drug responsiveness phenotype. This knowledge, when applied to dosing or drug selection, can avoid adverse reactions or therapeutic failure and thus enhance therapeutic or prophylactic efficiency when treating a subject with a P2T modulator, such as a modulator identified by one of the exemplary screening assays described herein.

Monitoring of Effects During Clinical Trials

Monitoring the influence of compounds (e.g., drugs) on the expression or activity of P2T polypeptide/gene can be applied not only in basic drug screening, but also in clinical trials. For example, the effectiveness of an agent determined by a screening assay, as described herein, to increase P2T gene expression, protein levels, or up-regulate P2T activity, can be monitored in clinical trials of subjects exhibiting decreased P2T gene expression, protein levels, or down-regulated P2T polypeptide activity. Alternatively, the effectiveness of an agent, determined by a screening assay, to decrease P2T gene expression, protein levels, or down-regulate P2T polypeptide activity, can be monitored in clinical trials of subjects exhibiting increased P2T gene expression, protein levels, or up-regulated P2T polypeptide activity. In such clinical trials, the expression or activity of a P2T polypeptide and, preferably, other genes which have been implicated in, for example, a nervous system related disorder can be used as a "read out" or markers of the ligand responsiveness of a particular cell.

For example, and not by way of limitation, genes, including a P2T gene, which are modulated in cells by treatment with a compound (e.g., drug or small molecule) which modulates P2T polypeptide/gene activity (e.g., identified in a screening assay as described herein) can be identified. Thus, to study the effect of compounds on CNS disorders, for example, in a clinical trial, cells can be isolated and RNA prepared and analyzed for the levels of expression of a P2T gene and other genes implicated in the disorder. The levels of gene expression (i e., a gene expression pattern) can be quantified by Northern blot analysis or RT-PCR, as described herein, or alternatively by measuring the amount of protein produced, by one of the methods described herein, or by measuring the levels of activity of a P2T polypeptide or other genes. In this way, the gene expression pattern can serve as an marker, indicative of the physiological response of the cells to the compound. Accordingly, this response state may be determined before, and at various points during, treatment of the individual with the compound.

In a preferred embodiment, the present invention provides a method for monitoring the effectiveness of treatment of a subject with a compound (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the compound; (ii) detecting the level of expression of a P2T polypeptide, mRNA, or genomic DNA in the preadministration sample; (iii) obtaining one or more post-administration samples from the subject; (iv) detecting the level of expression or activity of the P2T polypeptide, mRNA, or genomic DNA in the post-administration samples; (v) comparing the level of expression or activity of the P2T polypeptide, mRNA, or genomic DNA in the pre-administration sample with the P2T polypeptide, mRNA, or genomic DNA in the post administration sample or samples; and (vi) altering the administration of the compound to the subject accordingly. For example, increased administration of the compound may be desirable to increase the expression or activity of a P2T polypeptide/gene to higher levels than detected, i.e., to increase the effectiveness of the agent.

Alternatively, decreased administration of the agent may be desirable to decrease expression or activity of P2T to lower levels than detected, i.e. to decrease the effectiveness of the compound.

Pharmaceutical Compositions

The P2T nucleic acid molecules, P2T polypeptides (particularly fragments of P2T), modulators of a P2T polypeptide, and anti-P2T antibodies (also referred to herein as "active compounds") of the invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a P2T polypeptide or anti-P2T antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressured container or dispenser which contains a suitable propellant, e.g., a gas such as carbon dioxide, or a nebulizer. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811 which is incorporated by reference herein in its entirety.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system. The pharmaceutical compositions can be included in a container, pack, or dispenser together with instructions for administration.

H. Uses of Partial P2T Sequences

Fragments or fragments of the cDNA sequences identified herein (and the corresponding complete gene sequences) can be used in numerous ways as polynucleotide reagents. For example, these sequences can be used to: (a) map their respective genes on a chromosome; and, thus, locate gene regions associated with genetic disease; (b) identify an individual from a minute biological sample (tissue typing); and (c) aid in forensic identification of a biological sample. These applications are described in the subsections below.

Chromosome Mapping

Once the sequence (or a fragment of the sequence) of a gene has been isolated, this sequence can be used to map the location of the gene on a chromosome. This process is called chromosome mapping. Accordingly, fragments of a P2T nucleic acid sequences can be used to map the location of the P2T gene, respectively, on a chromosome. The mapping of the P2T sequence to chromosomes is an important first step in correlating these sequence with genes associated with disease.

Briefly, the P2T gene can be mapped to a chromosome by preparing PCR primers (preferably 15–25 bp in length) from the P2T gene sequence. Computer analysis of the P2T gene sequence can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the P2T gene sequence will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al., 1983). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the P2T gene sequence to design oligonucleotide primers, sublocalization can be achieved with panels of fragments from specific chromosomes. Other mapping strategies which can similarly be used to map a P2T gene sequence to its chromosome include in situ hybridization (described in Fan et al., 1990), prescreening with labeled flow-sorted chromosomes, and preselection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, above). McKusick, Mendelian Inheritance in Man, available on-line through Johns Hopkins University Welch Medical Library. The relationship between genes and disease, mapped to the same chromosomal region, can then be identified through linkage analysis (co-inheritance of physically adjacent genes).

Moreover, differences in the DNA sequences between individuals affected and unaffected with a disease associated with the P2T gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The P2T gene sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected fragments of an individual's genome. Thus, the P2T sequences described herein can be used to prepare two PCR primers from the 5' and 3' ends of the sequences. These primers can then be used to amplify an individual's DNA and subsequently sequence it.

Panels of corresponding DNA sequences from individuals prepared in this manner can provide unique individual identifications, as each individual will have a unique set of such DNA sequences due to allelic differences. The sequences of the present invention can be used to obtain such identification sequences from individuals and from tissue. The P2T gene sequences of the invention uniquely represent fragments of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequence of SEQ ID NO: 1 can comfortably provide positive individual identification with a panel of perhaps 10 to 1,000 primers which each yield a noncoding amplified sequence of 100 bases. If a predicted coding sequence, such as that in SEQ ID NO: 1 is used, a more appropriate number of primers for positive individual identification would be 500–2,000.

If a panel of reagents from the P2T gene sequences described herein is used to generate a unique identification database for an individual, those same reagents can later be used to identify tissue from that individual. Using the unique identification database, positive identification of the individual, living or dead, can be made from extremely small tissue samples.

EXAMPLES

The following examples are carried out using standard techniques, which are well known and routine to those of skill in the art, except where otherwise described in detail. The following examples are presented for illustrative purpose, and should not be construed in any way limiting the scope of this invention.

Example 1

Materials and Methods

Materials

Purinergic ligands and 3-aminotriazole were purchased from Sigma RBI. CPRG was purchased from Boehringer Mannheim. Mouse genomic DNA and multiple tissue northern blots were purchased from Clontech. The chemiluminescent β-galactosidase assay kit GAL-SCREEN™ was purchased from TROPIX.

Identification of Genomic Sequences Encoding the Mouse P2T Receptor

A BLAST search (Altschul et al., 1990) of the Genbank cDNA sequence database with the human EBI-2 receptor sequence (U.S. Pat. No. 6,060,272) identified a full length cDNA sequence encoding the mouse P2T receptor (Accession No. AK013804) (Adachi et al., 2001). A similar search of the Celera mouse genome sequence database with the mouse cDNA sequence identified a 46,358 base pair segment encoding the mouse P2T promoter and transcript. The mouse P2T mRNA is encoded in four exons (SEQ ID NO:1), three of which comprise the 5' untranslated region. The mouse P2T open reading frame is encoded in a single uninterrupted exon from nucleotide 45,167 to nucleotide 46,358 of SEQ ID NO:1.

Cloning of the Mouse P2T Receptor

The mouse P2T receptor protein coding sequences were amplified from mouse genomic DNA using oligos MPO720 (5' AA GGATCC AAA ATG GAT GTG CCT GGT GTC; SEQ ID NO:7) and MPO721 (5' AA CTCGAG CTA CAT TGG GGT CTC TTC GC; SEQ ID NO:8) that add BamHI to the 5' end and a XhoI site to the 3' end. The fragment was cloned into corresponding sites in the multicopy yeast expression vector, p426GPD (Mumberg et al., 1995) producing pMP344.

Yeast Expression

The EC323 yeast expression plasmids were introduced into variants of MPY578 cells (MATa ura3 his3 trp1 leu2 lys2 ade2 far1::LYS2 fus1::FUS1-HIS3 sst2::SST2-G418$^R$ ste2::LEU2) (Pausch et al., 1998) using LiOAc and selected for ura prototrophy. In order to facilitate coupling of the P2T receptor to G protein, MPY578 variant cells express chimeric G alpha proteins coupled to the mating signal transduction pathway. The chimeric constructs are expressed from the GPA1 locus and are composed of Gpa1 sequences in which the 5 C-terminal amino acids have been replaced with those of all the mammalian Gα proteins. A multicopy FUS1-LacZ reporter gene plasmid, pMP283, was introduced into P2T receptor-containing cells and selected on media lacking trp and ura. The resulting yeast strains were used for further analysis.

Yeast Cell-Based Assay of Mouse P2T Receptor Agonist Activation

MPY578 cells that express Gpa1-Gαt chimeric G alpha protein and containing pMP344 and pMP283 were diluted in assay medium (SCD-ura-trp, pH 6.8, 25 mM PIPES, 1 mM 3-aminotriazole) dispensed (5×10$^6$/ml, 200 µl/well) to the wells of 96-well microtiter dishes containing purinergic ligands. The plates were incubated with shaking (600 rpm) at 30° C. for 3 hours. Samples (25 µl) were transferred to Wallac B & W isoplates for β-galactosidase assay. An equal volume of GAL-SCREEN lysis and chemiluminescent β-galactosidase assay mixture was added. The plates were incubated for 30 min at 30° C. and light emission measured using a Wallac Victor II. Assays were conducted in quadruplicate and results were plotted using GraphPad Prizm.

Northern Blotting Analysis of mRNA Expression

A 400 bp fragment corresponding to position +70 to +470 with respect to ATG was PCR amplified from the murine P2T receptor clone using oligos F2 (CAG AGA CTA CAA GAT CAC CCA GGT; SEQ ID NO:9) and R3 (GAA GGC CCA GAT GAC AAC AGA AAG A; SEQ ID NO:10). The DNA fragment was labeled with $^{32}$P-dCTP by random priming (Life Technologies, Rockville, Md.) and used as probe to screen a mouse multiple tissue northern blot (Clontech, Palo Alto, Calif.). The blot was washed at final stringency of 0.5×SSC, 0.5% SDS, at 60° C. and exposed to film. The resulting image was captured electronically for documentation (Scion Corp. Bethesda, Md.).

In situ Hybridization

Distribution of murine P2T receptor mRNA within the mouse brain was assessed in situ as described previously (Kwak et al., 1993). Briefly, frozen mouse brains from C57/BL6 strain were sectioned on a cryostat (Bright-hacker, Fairfield, N.J.). Coronal as well as para-sagittal 15 µm sections were thaw-mounted on polylysine-coated slides and stored at −70° C. On the day of experimentation, the slides were postfixed in 4% paraformaldehyde for 1 hour. Riboprobe complementary to region +70 to +470 bp of murine P2T was sythesized by an in vitro transcription reaction which incorporated [$^{33}$P] UTP. Approximately 2 million cpm were applied per slide for hybridization. The sections were incubated at 55° C. overnight, treated with RNase A and then washed in 0.5×SSC at 65° C. for 1 hour. The sections were initially exposed on film and subsequently dipped in emulsion for further analysis.

Example 2

Cloning of the Murine P2T Receptor

Queries of the Celera mouse genome DNA sequence database using the DNA sequence of the human orphan P2T, EBI-2, revealed fragments that once assembled into a single contiguous sequence, appeared to encode a presumptive murine ortholog. Comparison of the genomic sequence with a recently reported cDNA sequence identified in a search of the Genbank indicates that the murine genomic sequence encodes the apparent protein coding sequence in a single uninterrupted exon (data not shown). The genomic sequence appears to encode an intron in the untranslated region of the mRNA immediately upstream of the initiator codon. A complete description of the mouse EBI-2 locus awaits complete assembly of the mouse genome. The predicted protein was 347 amino acids in length and was 86% identical to the human version and 95% identical to the rat (FIG. 1). The similarity between the three proteins is even greater in the transmembrane domains were only four conservative substitutions were found. The greatest divergences were found in the amino terminal extracellular domain and carboxy terminal intracellular domains. The P2T receptors exhibit the greatest degree of similarity to a subset of the P2Y receptors including the UDP-glucose receptor (Chambers et al., 2000) and H963 (Jacobs et al., 1997). Oligonucleotides corresponding to the 5' and 3' ends of the predicted protein coding region were used to amplify a fragment from mouse genomic DNA.

Example 3

Pharmacological Analysis

The murine P2T was expressed in yeast cells modified to permit agonist-induced expression of a β-galactosidase reporter gene (Pausch et al, 1998; Pausch, 1997). Agonist activation of the P2T with various purinergic ligands induces a dose-dependent activation of the murine receptor that responds with pharmacological properties comparable to the cloned human P2T receptor (Zhang et al., 2001; Hollopeter et al., 2001) (FIG. 2). The EC50 for ADP stimulation of the mouse P2T assayed in yeast was 256 nM. In *Xenopus oocytes* injected with P2T receptor cRNA and coupled to stimulation of coinjected Kir3.1/Kir3.2 inwardly rectifying K$^+$ currents, the EC50 was 300 nM (Hollopeter et al., 2001). In NIH3T3 cells, the P2T receptor transiently transfected along with a chimeric Gq5 construct produced and EC50 of 74 nM measured by FLIPR (Boyer et al., 1993). Assays of ADP dependent inhibition of cAMP accumulation gave an EC50 of 61 nM (Zhang et al., 2001). The rank order of potency of agonist stimulation of the mouse P2T receptor (2MeSADP>2MeSATP>ADP=ADPβS>ATPγS>2ClATP) agrees well with reported values for the human P2T receptor measured in FLIPR (2MeSADP=2MeSATP>ADP= ADPβS>2ClATP>ATPγS) and in adenylyl cyclase inhibition assays (2MeSATP>2MeSADP>ADP>ATPγS>ADPβS> 2ClATP) (Zhang et al, 2001).

Mammalian cell expression and measurement of intracellular calcium. NIH3T3 cells were stably transfected with pCDNA-Gαq/i3 by electroporation and cultured in the presence of 800 µg/ml neomycin. The NIH3T3 Gαq/i3 line was subsequently stably transfected with pCDNA3.1-mP2Y12 by electroporation and cultured in the presence of 800 µg/ml neomycin and 400 µg/ml hygromycin. Cells were plated without selection and grown overnight at 37° C. The cells were washed with Hank's balanced salt solution without phenol red plus 20 mM HEPES, 2.5 mM probenecid, pH 7.4 and loaded with wash solution plus 5 µM Fluo-4, 0.04% pluronic acid and 1% fetal bovine serum for 1 hour at 37° C. After removing the dye solution and washed with wash buffer, agonists were added and analyzed using the FLIPR (PE Biosystems) to measure accumulation of intracellular calcium in response to compound treatments.

Figure 4:
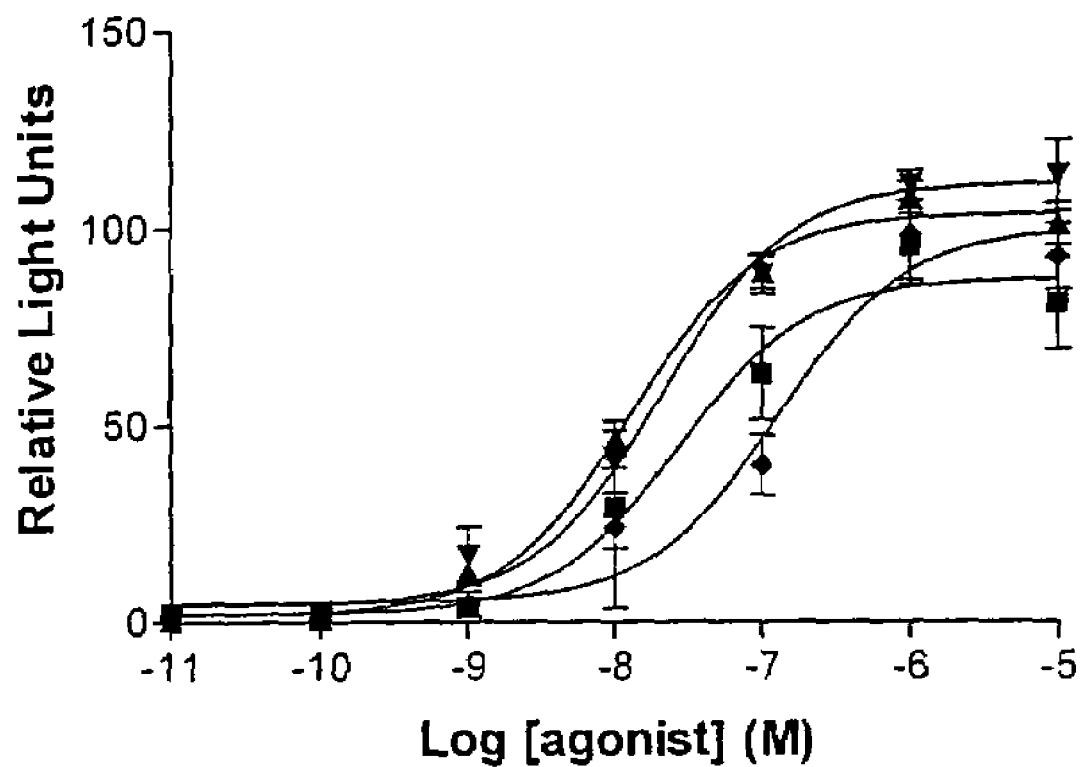
FIG. 4 shows the murine P2Y12 agonist-induced release of intracellular calcium. NIH3T3 cells expressing the mouse P2Y12 and a chimeric Gαq/i3 were assayed for agonist-induced release of intracellular calcium as described in the Methods and Materials section. Symbols: square, ADP; triangle, 2MeSADP; inverted triangle, ADPβS; diamond, ATPγS.

Agonist activation of the P2Y12 with various purinergic ligands induces a dose-dependent activation of the murine receptor that responds with pharmacological properties comparable to the cloned human P2Y12 receptor. The EC50 for ADP stimulation of the mouse P2Y12 dependent release of intracellular calcium is detected in FLIPR with an EC50 of 27 nM (FIG. 4). In published reports, Xenopus oocytes injected with the human P2Y12 receptor cRNA and coupled to stimulation of coinjected Kir3.1/Kir3.2 inwardly rectifying K+ currents, the EC50 was 300 nM (Hollopeter, 2001). In NIH3T3 cells, the human P2Y12 receptor expressed along with a chimeric Gq/i3 construct produced an EC50 of 74 nM measured by FLIPR (Zhang, 2001). Assays of ADP dependent inhibition of cAMP accumulation gave an EC50 of 61 nM (Zhang, 2001). The rank orders of potency of agonist stimulation of the mouse P2Y12 receptor in FLIPR (2MeSADP>ADP=ADPβS>ATPγS) agree well with reported values for the human P2Y12 receptor measured in FLIPR (2MeSADP=2MeSATP>ADP=ADPβS>2ClATP>ATPγS) and in adenylyl cyclase inhibition assays (2MeSATP>2MeSADP>ADP>ATPγS>ADPβS>2ClATP) (Zhang, 2001).

Example 4

Expression Analysis of the P2T Receptor

Figure 3:
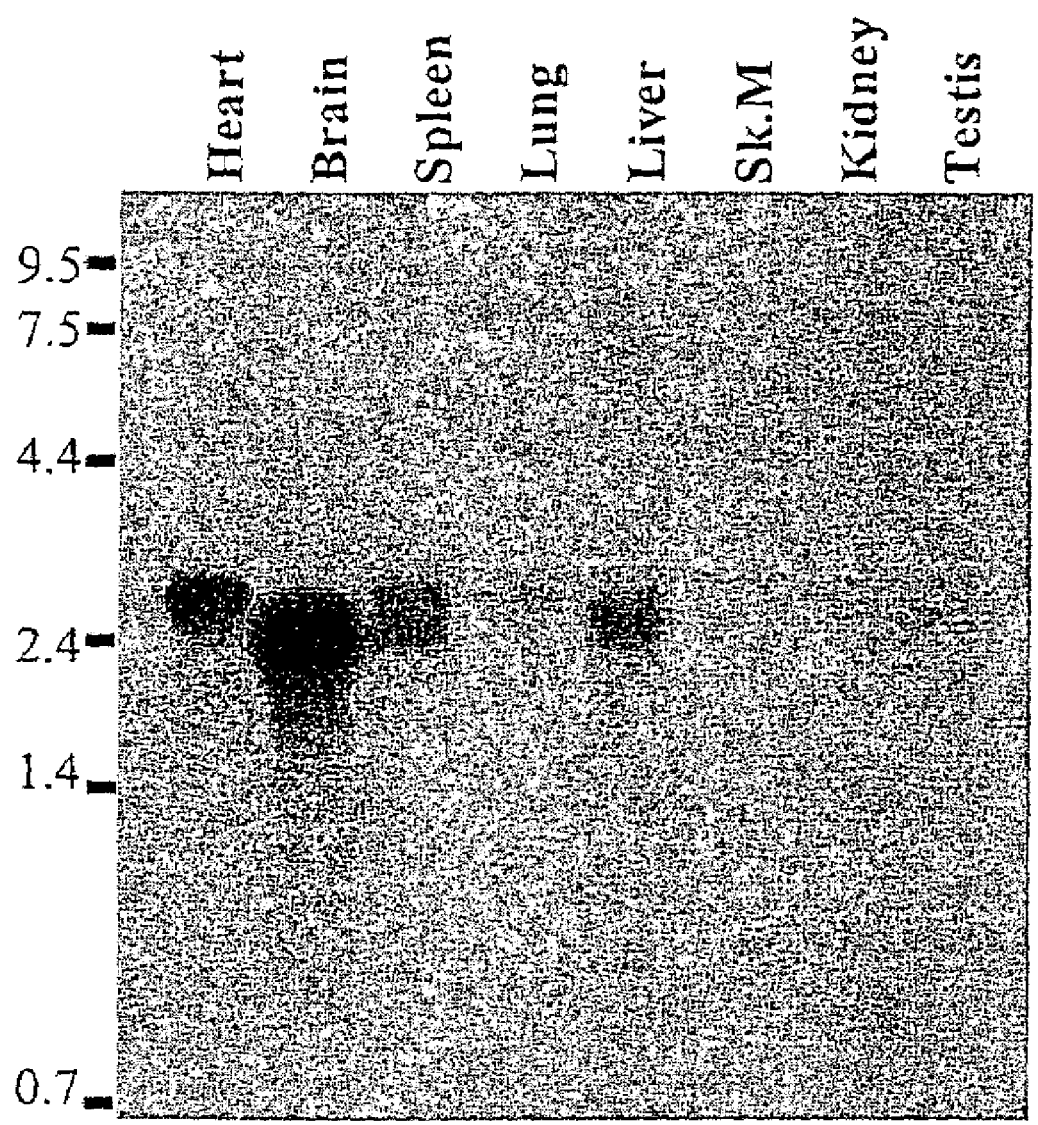
FIG. 3 shows a northern blot analysis of mouse P2T receptor mRNA expression. Hybridization of a mouse P2T probe to mouse multiple tissue northern blot (Clontech).

Northern blotting analysis was performed on mRNA extracted from various murine tissues (FIG. 3). A single prominent 2.4 kb band was detected in brain. Lesser amounts were present in liver, spleen and testis. A 2.6 kb band was detected as well in heart, lung and kidney. Notably, spleen RNA contain both the 2.4 kb and 2.6 kb species.

In situ hybridization using a murine P2T probe (data not shown) reveals broadly diffuse and uniform signal throughout the brain. Unlike the neuron-specific Wave-1 mRNA, which is expressed in discrete layers of pyramidal and granule neurons within the hippocampus, the P2T receptor signal is in all major fiber tracts including the corpus callosum and brain stem pyramidal tracts suggesting that the mRNA is in glia. Examination at high magnification of emulsion-dipped slides counter stained with cresyl violet confirms that murine P2T receptor mRNAs are expressed exclusively in astroglial or microglial cells of the brain and not in neurons.

Example 5

Identification of Ligands for Mouse P2T in Mammalian Cells

Cell Line Generation

The open reading frame of mouse P2T is ligated into the mammalian expression vector pCDNA3.1+ zeo (Invitrogen, 1600 Faraday Avenue, Carlsbad, Calif. 92008). HEK293 or NIH3T3 cells are transfected with the plasmid and selected with 500 µg/ml zeocin. Zeocin resistant clones are tested for expression of mouse P2T by RT-PCR and then tested for their ability to stimulate or inhibit cAMP production.

Adenylylcyclase Assay $4 \times 10^5$ cells are plated into 96 well Biocoat cell culture plates (Becton Dickinson, 1 Becton Drive, Franklin Lakes, N.J. 07417-1886) 24 hours prior to assay. The cells are then incubated in Krebs-bicarbonate buffer at 37° C. for 15 minutes. A 5 minute pretreatment with 500 µM isobutylmethyl xanthine (IBMX) precedes addition of test compounds. To test for stimulation of adenylylcyclase, the test chemical compounds (10 µM) are added and incubated with the cells for 12 minutes at 37° C. and cAMP levels are determined using the SPA assay (Amersham Pharmacia Biotech, 800 Centennial Avenue, Pistcataway, N.J. 08855). An increase in cAMP reflects stimulation of adenylylcyclase. To test for inhibition, adenylylcyclase is stimulated with 1 µM forskolin for 12 minutes at 37° C. prior to addition of the test chemical compounds. Test compounds (10 µM) are added and incubated with the cells for 12 minutes at 37° C. and cAMP levels are determined using the SPA assay (Amersham Pharmacia Biotech, 800 Centennial Avenue, Pistcataway, N.J. 08855). A decrease in forskolin stimulated cAMP levels reflects inhibition of adenylylcyclase.

Example 6

Inhibition of P2T Production

Design of RNA molecules as Compositions of the Invention

All RNA molecules in this experiment are approximately 600 nucleotides in length, and all RNA molecules are designed to be incapable of producing functional P2T protein. The molecules have no cap and no poly-A sequence; the native initiation codon is not present, and the RNA does not encode the full-length product. The following RNA molecules are designed:

(1) a single-stranded (ss) sense RNA polynucleotide sequence homologous to a portion of P2T murine messenger RNA (mRNA);

(2) a ss anti-sense RNA polynucleotide sequence complementary to a portion of P2T murine mRNA, (3) a double-stranded (ds) RNA molecule comprised of both sense and anti-sense a portion of P2T murine mRNA polynucleotide sequences, (4) a ss sense RNA polynucleotide sequence homologous to a portion of P2T murine heterogeneous RNA (hnRNA), (5) a ss anti-sense RNA polynucleotide sequence complementary to a portion of P2T murine hnRNA, (6) a ds RNA molecule comprised of the sense and anti-sense P2T murine hnRNA polynucleotide sequences, (7) a ss murine RNA polynucleotide sequence homologous to the top strand of the a portion of P2T promoter, (8) a ss murine RNA polynucleotide sequence homologous to the bottom strand of the a portion of P2T promoter, and (9) a ds RNA molecule comprised of murine RNA polynucleotide sequences homologous to the top and bottom strands of the P2T promoter.

The various RNA molecules of (1)–(9) above may be generated through T7 RNA polymerase transcription of PCR products bearing a T7 promoter at one end. In the instance where a sense RNA is desired, a T7 promoter is located at the 5' end of the forward PCR primer. In the instance where an antisense RNA is desired, the T7 promoter is located at the 5' end of the reverse PCR primer. When dsRNA is desired both types of PCR products may be included in the T7 transcription reaction. Alternatively, s nse and anti-sense RNA may be mixed together after transcription, under annealing conditions, to form ds RNA.

Construction of Expression Plasmid Encoding a Fold-Back Type of RNA

An expression plasmid encoding an inverted repeat of a portion of the P2T gene may be constructed using the information disclosed in this application. A DNA fragment encoding a P2T foldback transcript may be prepared by PCR amplification and introduced into suitable restriction sites of a vector which includes the elements required for transcription of the P2T foldback transcript. The DNA fragment would encode a transcript that contains a fragment of the P2T gene of approximately at least 600 nucleotides in length, followed by spacer sequence of at least 10 bp but not more than 200 bp, followed by the reverse complement of the P2T sequence chosen. CHO cells transfected with the construct will produce only fold-back RNA in which complementary target gene sequences form a double helix.

Assay

Balb/c mice (5 mice/group) may be injected intercranially with the murine P2T chain specific RNAs described above or with controls at doses ranging between 10 µg and 500 µ/g. Brains are harvested from a sample of the mice every four days for a period of three weeks and assayed for P2T levels using the antibodies as disclosed herein or by northern blot analysis for reduced RNA levels.

According to the present invention, mice receiving ds RNA molecules derived from both the P2T mRNA, P2T hnRNA and ds RNA derived from the P2T promoter demonstrate a reduction or inhibition in P2T production. A modest, if any, inhibitory effect is observed in sera of mice receiving the single stranded P2T derived RNA molecules, unless the RNA molecules have the capability of forming some level of double-strandedness.

Example 7

Production of Transfected Cell Strains by Gene Targeting

Gene targeting occurs when transfecting DNA either integrates into or partially replaces chromosomal DNA sequences through a homologous recombinant event. While such events can occur in the course of any given transfection experiment, they are usually masked by a vast excess of events in which plasmid DNA integrates by nonhomologous, or illegitimate, recombination.

Generation of a Construct Useful for Selection of Gene Targeting Events in Human Cells One approach to selecting the targeted events is by genetic selection for the loss of a gene function due to the integration of transfecting DNA. The human HPRT locus encodes the enzyme hypoxanthine-phosphoribosyl transferase. HPRT- cells can be selected for by growth in medium containing the nucleoside analog 6-thioguanine (6-TG): cells with the wild-type (HPRT+) allele are killed by 6-TG, while cells with mutant (hprt-) alleles can survive. Cells harboring targeted events which disrupt HPRT gene function are therefore selectable in 6-TG medium.

To construct a plasmid for targeting to the HPRT locus, the 6.9 kb HindIII fragment extending from positions 11,960–18,869 in the HPRT sequence (Genebank name HUMHPRTB; Edwards, A. et al., Genomics 6:593–608 (1990)) and including exons 2 and 3 of the HPRT gene, may be subcloned into the HindIII site of pUC12. The resulting clone is cleaved at the unique XhoI site in exon 3 of the HPRT gene fragment and the 1.1 kb SalI-XhoI fragment containing the neo gene from pMC1Neo (Stratagene) is inserted, disrupting the coding sequence of exon 3. One orientation, with the direction of neo transcription opposite that of HPRT transcription was chosen and designated pE3Neo. The replacement of the normal HPRT exon 3 with the neo-disrupted version will result in an HPRT-, 6-TG resistant phenotype. Such cells will also be G418 resistant.

Generation of a Construct for Targeted Insertion of a Gene of Therapeutic Interest into the Human Genome and its Use in Gene Targeting A variant of pE3Neo, in which a P2T gene is inserted within the HPRT coding region, adjacent to or near the neo gene, can be used to target the P2T gene to a specific position in a recipient primary or secondary cell genome. Such a variant of pE3Neo can be constructed for targeting the P2T gene to the HPRT locus.

A DNA fragment containing the P2T gene and linked mouse metallothionein (mMT) promoter is constructed. Separately, pE3Neo is digested with an enzyme which cuts at the junction of the neo fragment and HPRT exon 3 (the 3' junction of the insertion into exon 3). Linearized pE3Neo fragment may be ligated to the P2T-mMT fragment.

Bacterial colonies derived by transfection with the ligation mixture are screened by restriction enzyme analysis for a single copy insertion of the P2T-mMT fragment. An insertional mutant in which the P2T DNA is transcribed in the same direction as the neo gene is chosen and designated pE3Neo/P2T. pE3Neo/P2T is digested to release a fragment containing HPRT, neo and mMT-P2T sequences. Digested DNA is treated and transfected into primary or secondary human fibroblasts. G418$^r$ TG$^r$ colonies are selected and analyzed for targeted insertion of the mP2T and neo sequences into the HPRT gene. Individual colonies may be assayed for P2T expression using antibodies as described elsewhere herein.

Secondary human fibroblasts may be transfected with pE3Neo/P2T and thioguanine-resistant colonies analyzed for stable P2T expression and by restriction enzyme and Southern hybridization analysis.

The use of homologous recombination to target a P2T gene to a specific position in a cell's genomic DNA can be expanded upon and made more useful for producing products for therapeutic purposes (e.g., pharmaceuticals, gene therapy) by the insertion of a gene through which cells containing amplified copies of the gene can be selected for by exposure of the cells to an appropriate drug selection regimen. For example, pE3neo/P2T can be modified by inserting the dhfr, ada, or CAD gene at a position immediately adjacent to the P2T or neo genes in pE3neo/P2T. Primary, secondary, or immortalized cells are transfected with such a plasmid and correctly targeted events are identified. These cells are further treated with increasing concentrations of drugs appropriate for the selection of cells containing amplified genes (for dhfr, the selective agent is methotrexate, for CAD the selective agent is N-(phosphonacetyl)-L-aspartate (PALA), and for ada the selective agent is an adenine nucleoside (e.g., alanosine). In this manner the integration of the gene of therapeutic interest will be coamplified along with the gene for which amplified copies are selected. Thus, the genetic engineering of cells to produce genes for therapeutic uses can be readily controlled by preselecting the site at which the targeting construct integrates and at which the amplified copies reside in the amplified cells.

Construction of Targeting Plasmids for Placing the P2T Gene Under the Control of the Mouse Metallothionein Promoter in Primary, Secondary and Immortalized Human Fibroblasts The following serves to illustrate one embodiment of the present invention, in which the normal positive and negative regulatory sequences upstream of the P2T gene are altered to allow expression of P2T in primary, secondary or immortalized human fibroblasts or other cells which do not express P2T in significant quantities.

Unique sequences of SEQ ID NO:1 are selected which are located upstream from the P2T coding region and ligated to the mouse metallothionein promoter as targeting sequences. Typically, the 1.8 kb EcoRI-BglII from the mMT-I gene (containing no mMT coding sequences; Hamer, D. H. and Walling M., J. Mol. Appl. Gen. 1:273 288 (1982); this fragment can also be isolated by known methods from mouse genomic DNA using PCR primers designed from analysis of mXT sequences available from Genbank; i.e., MUSMTI, MUSMTIP, MUSMTIPRM) is made blunt-ended by known methods and ligated with the 5' P2T sequences. The orientations of resulting clones are analyzed and suitable DNAs are used for targeting primary and secondary human fibroblasts or other cells which do not express P2T in significant quantities.

Additional upstream sequences are useful in cases where it is desirable to modify, delete and/or replace negative regulatory elements or enhancers that lie upstream of the initial target sequence.

The cloning strategies described above allow sequences upstream of P2T to be modified in vitro for subsequent targeted transfection of primary, secondary or immortalized human fibroblasts or other cells which do not express P2T in significant quantities. The strategies describe simple insertions of the mMT promoter, and allow for deletion of the negative regulatory region, and deletion of the negative regulatory region and replacement with an enhancer with broad host-cell activity.

Targeting to Sequences Flanking the P2T Gene and Isolation of Targeted Primary, Secondary and Immortalized Human Fibroblasts by Screening Targeting fragment containing the mMT promoter and P2T upstream sequences may be purified by phenol extraction and ethanol precipitation and transfected into primary or secondary human fibroblasts. Transfected cells are plated onto 150 mm dishes in human fibroblast nutrient medium. 48 hours later the cells are plated into 24 well dishes at a density of 10,000 cells/cm$^2$ (approximately 20,000 cells per well) so that, if targeting occurs at a rate of 1 event per $10^6$ clonable cells then about 50 wells would need to be assayed to isolate a single expressing colony. Cells in which the transfecting DNA has targeted to the homologous region upstream of P2T will express P2T under the control of the mMT promoter. After 10 days, whole well supernatants are assayed for P2T expression. Clones from wells displaying P2T synthesis are isolated using known methods, typically by assaying fractions of the heterogenous populations of cells separated into individual wells or plates, assaying fractions of these positive wells, and repeating as needed, ultimately isolating the targeted colony by screening 96-well microtiter plates seeded at one cell per well. DNA from entire plate lysates can also be analyzed by PCR for amplification of a fragment using primers specific for the targeting sequences. Positive plates are trypsinized and replated at successively lower dilutions, and the DNA preparation and PCR steps repeated as needed to isolate targeted cells.

Targeting to Sequences Flanking the Human P2T Gene and Isolation of Targeted Primary, Secondary and Immortalized Human Fibroblasts by a Positive or a Combined Positive/Negative Selection System Construction of 5' P2T-mMT targeting sequences and derivatives of such with additional upstream sequences can include the additional step of inserting the neo gene adjacent to the mMT promoter. In addition, a negative selection marker, for example, gpt (from PMSG (Pharmacia) or another suitable source), can be inserted. In the former case, G418$^r$ colonies are isolated and screened by PCR amplification or restriction enzyme and Southern hybridization analysis of DNA prepared from pools of colonies to identify targeted colonies. In the latter case, G418$^r$ colonies are placed in medium containing 6-thioxanthine to select against the integration of the gpt gene (Besnard, C. et al., Mol. Cell. Biol. 7:4139–4141 (1987)). In addition, the HSV-TK gene can be placed on the opposite side of the insert to gpt, allowing selection for neo and against both gpt and TK by growing cells in human fibroblast nutrient medium containing 400 μg/ml G418, 100 μM 6-thioxanthine, and 25 μg/ml gancyclovir. The double negative selection should provide a nearly absolute selection for true targeted events and Southern blot analysis provides an ultimate confirmation.

The targeting schemes herein described can also be used to activate P2T expression in immortalized human cells (for example, HT1080 fibroblasts, HeLa cells, MCF-7 breast cancer cells, K-562 leukemia cells, KB carcinoma cells or 2780AD ovarian carcinoma cells) for the purposes of producing P2T for conventional pharmaceutical delivery.

The targeting constructs described and used in this example can be modified to include an amplifiable selectable marker (e.g., ada, dhfr, or CAD) which is useful for selecting cells in which the activated endogenous gene, and the amplifiable selectable marker, are amplified. Such cells, expressing or capable of expressing the endogenous gene encoding a P2T product can be used to produce proteins for conventional pharmaceutical delivery or for gene therapy.

Equivalents: Those skilled in the art will recognize, or be able to ascertain using no more than routine experimentation, many equivalents to the specific embodiments of the invention described herein. Such equivalents are intended to be encompassed by the following claims.

REFERENCES

European Application No. EP 036776
European Application No. EP 859055
European Application No. EP 125,023
European Application No. EP 171,496
European Application No. EP 184,187
European Application No. EP 264166
U.S. Pat. No. 4,196,265
U.S. Pat. No. 4,522,811
U.S. Pat. No. 4,554,101
U.S. Pat. No. 4,683,195
U.S. Pat. No. 4,683,202
U.S. Pat. No. 4,736,866
U.S. Pat. No. 4,816,567
U.S. Pat. No. 4,870,009
U.S. Pat. No. 4,873,191
U.S. Pat. No. 4,873,316
U.S. Pat. No. 4,987,071
U.S. Pat. No. 5,116,742
U.S. Pat. No. 5,223,409

U.S. Pat. No. 5,272,057
U.S. Pat. No. 5,283,317
U.S. Pat. No. 5,328,470
U.S. Pat. No. 5,498,531
U.S. Pat. No. 5,696,237
U.S. Pat. No. 5,766,844
U.S. Pat. No. 5,789,654
U.S. Pat. No. 5,798,209
U.S. Pat. No. 5,968,502
U.S. Pat. No. 6,054,297
U.S. SIR No. H1,892
International Application No. WO 86/01533
International Application No. WO 90/02809
International Application No. WO 90/11354
International Application No. WO 91/01140
International Application No. WO 91/17271
International Application No. WO 92/01047
International Application No. WO 92/09680
International Application No. WO 92/09690
International Application No. WO 92/15679
International Application No. WO 92/18619
International Application No. WO 92/20791
International Application No. WO 93/01288
International Application No. WO 93/04169
International Application No. WO 94/10300
International Application No. WO 94/12650
International Application No. WO 94/16101
International Application No. WO 97/07668
International Application No. WO 97/07669
Abravaya et al., *Nucleic Acids Res.*, 23:675–682, 1995.
Adachi, J., et al., "Functional annotation of a full-length mouse cDNA collection," *Nature* 409, 865–690, 2001
Adams et al., *Nature* 355:632–634, 1992.
Adams et al., *Nature* 377 Supp:3–174, 1995.
Adams et al., *Science* 252:1651–1656, 1991.
Altschul et al., "Basic local alignment search tool." *J. Mol. Biol.* 215:403–410, 1990.
Altschul et al., "Gapped BLAST and PSI-BLAST: a new generation of protein database search programs" *Nucleic Acids Res.* 25:3389–3402, 1997.
Amann et al., *Gene* 69:301–315, 1988.
Baldari et al., *Embo J.* 6:229–234, 1987.
Banerji et al., *Cell*, 33:729–740; 1983.
Bartel and Szostak, *Science* 261:1411–1418, 1993.
Bartel et al. *Biotechniques* 14:920–924, 1993(b).
Bartel, "Cellular Interactions and Development: A Practical Approach", pp. 153–179, 1993(a).
Boeynaems et al., "P2Y receptors: in the middle of the road," *TIPS* 21, 1–3, 2000.
Boyer et al., "Identification of a P2Y-purinergic receptor that inhibits adenylyl cyclase," *J Pharmacol Exp Ther.* 267, 1140–1146, 1993.
Bradley, *Current Opinion in Biotechnology* 2:823–829, 1991.
Bradley, in "Teratocarcinomas and Embryonic Stem Cells: A Practical Approach," E. J. Robertson, ed., IRL, Oxford, pp. 113–152, 1987.
Bunzow et al., *Nature*, 336:783–787, 1988.
Burge and Karlin, "Prediction of complete gene structures in human genomic DNA." *J. Mol. Biol.* 268:78–94, 1997.
Byrne and Ruddle, *PNAS* 86:5473–5477, 1989.
Calame and Eaton, *Adv. Immunol.* 43:235–275, 1988.
Campes and Tilghman, *Genes Dev.* 3:537–546, 1989.
Cattaneo et al., "Identification of a new congenital defect of platelet function characterized by severe impairment of platelet responses to adenosine diphosphate," *Blood* 80, 2787–2796, 1992.
Chambers et al., "A G protein-coupled receptor for UDP-glucose," *J. Biol. Chem.* 275, 10767–71, 2000.
Chen and Chen, "ATP-induced arachadonic acid release in cultured astrocytes is mediated by Gi protein coupled P2Y1 and P2Y2 receptors," *Glia* 22, 360–370, 1998.
Chen et al., *PNAS* 91:3054–3057, 1994.
Cohen et al., *Adv. Chromatogr.* 36:127–162, 1996.
Cotton et al., PNAS 85:4397, 1988.
Cotton, *Mutat. Res.* 285:125–144, 1993.
D'Eustachio et al., *Science* 220:919–924, 1983.
Devereux et al., *Nucleic Acids Research* 12(1):387, 1984.
Doestschman et al., *J. Embryol. Exp. Morphol.* 87:27–45, 1985.
Edlund et al., *Science* 230:912–916, 1985.
Eichelbaum, *Clin. Exp. PharmacoL Physiol*, 23(10–11): 983–985, 1996.
Elledge et al., *Proc. Natl. Acad. Sci. USA*, 88:1731–1735, 1991.
Fan et al., *PNAS*, 87:6223–27, 1990.
Finely et al., *Proc. Natl. Acad. Sci. USA*, 91:12980–12984, 1994.
Frohman et al., *Proc. Natl. Acad. Sci. USA* 85, 8998–9002, 1988.
Gaultier et al., *Nucleic Acids Res.* 15:6625–6641, 1987.
Gentz et al., *Proc. Natl. Acad. Sci. USA*, 86:821–824, 1989.
Griffin et al., *Appl. Biochem. Biotechnol.* 38:147–159, 1993.
Gunnar von Heijne, "Membrane Protein Structure Prediction, Hydrophobicity Analysis and the Positive-inside Rule" *J. Mol. Biol.*, 225:487–494, 1992.
Harder et al, "P2-purinergic receptors," *Annu. Rev. Pharmacol. Toxicol.* 35, 541–579, 1995.
Harlow and Lane, "Antibodies: A Laboratory Manual," Cold Spring Harbor Laboratory Press, Cold Spring Harbor, N.Y., 1988
Harper et al, *Cell*, 75:805–816, 1993.
Haselhoff and Gerlach, *Nature* 334:585–591, 1988.
Hayashi, *Genet. Anal. Tech. Appl.* 9:73–79, 1992.
Helene et al., *Ann. N. Y Acad Sci.* 660:27–36, 1992.
Helene, *Anticancer Drug Des.* 6(6):569–84, 1991.
Hoffmann et al., (1999) "The role of amino acids in extracellular loops of the human P2Y1 receptor in surface expression and activation processes," *J Biol Chem.* 274, 14639–47, 1999.
Hogan, "Manipulating the Mouse Embryo," Cold Spring Harbor Laboratory Press, Cold Spring Harbor, N.Y., 1986.
Hollopeter et al., "Identification of the platelet ADP receptor targeted by antithrombotic drugs," *Nature* 409, 202–207, 2001.
Inoue et al., *FEBS Lett.* 215:327–330, 1987(a).
Inoue et al., *Nucleic Acids Res.* 15:6131–6148, 1987(b).
Iwabuchi et al., *Oncogene* 8:1693–1696, 1993
Jacobs et al., "A genetic selection for isolating cDNAs encoding secreted proteins," *Gene* 198, 289–296, 1997.
Jantzen et al., "Evidence for two distinct G-protein-coupled ADP receptors mediating platelet activation," *Thromb Haemost* 81, 111–117, 1999.
Jiang et al., "A mutational analysis of residues essential for ligand recognition at the human P2Y1 receptor," *Mol Pharmacol.* 52, 499–507, 1997.
Johnson et al., *Endoc. Rev.*, 10:317–331, 1989.
Kaufman et al., *EMBO J* 6:187–195, 1987.
Kessel and Gruss, *Science* 249:3 74–3 79, 1990.
Klein et al., *Curr. Genet.*, 16:145–152, 1989(b).
Klein et al., *Curr. Genet.* 13:29–35, 1989(a).
Kobilka et al., *Proc. Natl. Acad. Sci.*, USA, 84:46–50, 1987(a).
Kobilka et al., *Science*, 238:650–656, 1987(b).

Kunapuli, "Multiple P2 receptor subtypes on platelets: a new interpretation of their function," *TIPS* 19, 391–394, 1998.

Kurjan and Herskowitz, *Cell* 933–943, 1982.

Kyte and Doolittle, *J. Mol. Biol.*, 157:105–132, 1982.

Lakso et al., *PJVAS* 89:6232–6236, 1992.

Lefkowitz, *Nature*, 351:353–354, 1991.

Li et al., *Cell* 69:915, 1992.

Linder, *Clin. Chem.* 43(2):254–266, 1997.

Lucklow and Summers, *Virology* 170:31–39, 1989.

Madura et al., *J. Biol. Chem.* 268:12046–1205, 1993

Maher, *Bioassays* 14(12):807–15, 1992.

Mansour et al., *Nature* 336:348, 1988

Maxim and Gilbert, *PNAS* 74:560, 1977.

Morin et al., *Nucleic Acids Res.*, 21:2157–2163, 1993.

Mumberg et al., "Yeast vectors for the controlled expression of heterologous proteins in different genetic backgrounds," *Gene* 156, 119–122, 1995.

Myers et al., *Nature* 313:495, 1985(a).

Myers et al., *Science* 230:1242, 1985(b).

Nurden et al., "An inherited bleeding disorder linked to a defective interaction between ADP and its receptor on platelets," *J. Clin. Invest.* 95, 1612–1622, 1995.

O'Gonnan et al., *Science* 251:1351–1355, 1991.

Orita et al., *PNAS* 86:2766, 1989.

Pausch et al., Heterologous G Protein-Coupled Receptors Expressed in *Saccharomyces cerevisiae*: Methods for Genetic Analysis and Ligand Identification. In "Identification and Expression of G Protein-Coupled Receptors." (Ed. K. R. Lynch) "Receptor Biochemistry and Methodology" (Series Eds. Sibley, D. and Strader, C.), pp. 196–212, Wiley, Inc., 1998.

Pausch, "GPCRs in *Saccharomyces cerevisiae*: HTS assays for drug discovery," *TIB* 15, 48–494, 1997.

Pinkert et al. *Genes Dev.* 1:268–277, 1987.

Queen and Baltimore, *Cell* 33:741–748, 1983.

Ralevic and Burnstock, "Receptors for Purines and Pyrimidines," *Pharmacol. Rev.* 50, 413–492, 1998.

Robinson and Dowd, "Heterogeneity and functional properties of subtypes of sodium-dependent glutamate transporters in the mammalian central nervous system," *Adv. Pharmacology* 37, 69–115, 1997.

Rose et al., "Methods in Yeast Genetics: A Laboratory Course Manual." Cold Spring Harbor Press, Cold Spring Harbor, N.Y. (1990).

Saleeba et al., *Meth. Enzymol.* 217:286–295, 1992.

Sambrook et al., "Molecular Cloning: A Laboratory Manual" 2nd ed, Cold Spring Harbor Laboratory, Cold Spring Harbor Laboratory Press, Cold Spring Harbor, N.Y., 1989

Sanger, *PNAS* 74:5463, 1977.

Savi et al., "Identification and biological activity of the active metabolite of clopidogrel," *Thromb Haemost* 84, 891–896, 2000.

Schultz et al., *Gene* 54:113–123, 1987.

Seed, *Nature* 329:840, 1987.

Simon, et al., *Science*, 252:802–8, 1991.

Smith and Johnson, *Gene* 67:31–40, 1988.

Smith et al., *Mol. Cell Biol.* 3:2156–2165, 1983.

Songyang, et al., *Cell* 72:767–778, 1993.

Stadel et al., "Orphan G protein-coupled receptors: a neglected opportunity for pioneer drug discovery" *TIPS* 18:430–437, 1997.

Studier et al. "Gene Expression Technology" *Methods in Enzymology* 185, 60–89, 1990.

Thomas and Capecchi, *Cell* 51:503, 1987.

Webb et al., "The P2Y purinoceptor in rat brain microvascular endothelial cells couple to inhibition of adenylate cyclase," *Br. J. Pharmacol.* 119, 1385–1392, 1996.

Wilmut et al., *Nature* 385:810–813, 1997.

Wilson et al., *Cell* 37:767, 1984.

Winoto and Baltimore. *EMBO J* 8:729–733, 1989.

Zervos et al., *Cell* 72:223–232, 1993.

Zhang et al., "ADP is the cognate ligand for the orphan G protein-coupled receptor SP1999," *J. Biol. Chem.*, 276: 8608–8615, 2001.

---

What is claimed is:

1. An isolated murine genomic polynucleotide comprising the nucleic acid sequence of SEQ ID NO:1.

2. The polynucleotide of claim 1, further comprising heterologous polynucleotides.

3. A recombinant expression vector comprising a polynucleotide encoding a murine P2T receptor polypeptide, wherein the polynucleotide comprises the nucleic acid sequence of SEQ ID NO:1.

4. The vector of claim 3, wherein the vector DNA is selected from the group consisting of plasmid, episomal, YAC and viral.

5. The vector of claim 4, wherein the vector is a yeast expression plasmid.

6. The vector of claim 3, wherein the polynucleotide is operatively linked to one or more regulatory elements selected from the group consisting of a promoter, an enhancer, a splicing signal, a termination signal, a ribosomal binding signal and a polyadenylation signal.

7. A genetically engineered host cell, transfected, transformed or infected with the vector of claim 3.

8. The host cell of claim 7, wherein the host cell is eukaryotic.

9. The host cell of claim 8, wherein the eukaryotic cell is selected from the group consisting of yeast, mammal, insect and plant.

10. The host cell of claim 7, wherein the host cell is prokaryotic.

11. The host cell of claim 7, wherein the polynucleotide is expressed to produce the encoded polypeptide.

* * * * *

SEQUENCE LISTING

```
<160> NUMBER OF SEQ ID NOS: 10

<210> SEQ ID NO 1
<211> LENGTH: 46358
<212> TYPE: DNA
<213> ORGANISM: Mus musculus
<220> FEATURE:
<221> NAME/KEY: misc_feature
<222> LOCATION: (7632)..(7651)
<223> OTHER INFORMATION: unsure
<220> FEATURE:
<221> NAME/KEY: misc_feature
<222> LOCATION: (11838)..(11885)
<223> OTHER INFORMATION: unsure

<400> SEQUENCE: 1
aaaagtgcat ctacttcccc ctaagggcag ggattccctc caccatctcc attgctgcag      60
tgccaatggc tactcaggct ggcctttctg ttattttaaa gaaccttcca aagcgttgta     120
tagaaagcaa atgcccatct aatactgctt cttagagact aggtagtgtt gtaacacaag    180
ttttactaaa tactgcttac tcagcaaatg aaaattctta tcagcacaca ttttcttata    240
taaacatagc ttgtttccta tcctgatgta aaataataat tttattttac ttttatttct    300
```

-continued

```
tatgctaagc tgttacttaa gttttttggta gattctagaa atgccctgaa gtccagataa      360
gcattttaat tgggagatct ttgaagataa tggcttttt  cttttcttt  ttgcaatgcc       420 aatagctatt gtgctttgat gacaaaaatt ataccactga aaattaagaa aagtcacttg       480
gcttctataa ctagatatat ttatatatgt gggaaaaaac atttactctt gcctgttttt       540
tatcaataga gtcaaatcca gcaattttgt ttcccttgt  atcgatcaaa gaacccatgg       600
gttcacacgt gatgacatcg caggtctgct ttggcaaagg cagcaactgt cgaactttgt       660
caatgctttc tgacctcttg tctcctagtt cttctagaa  gaaagagggg ggaaaaatgt        720
aaaagcaaga gagaagtgag gcaaaaattc tgactttaca atgaagcaaa agctaacaag       780
aaggaagttc cccagtgaca catttccttt tttttagggc tagtatgtct ttagtcctta       840
gcgcagtcta tggaacagct gcaaattgga ctggtgaaat gtttcatttc ttctattcaa       900
gtagaaaatc agggtgcaca caaaggcagt cttgttctcc atgacaaatc agagtgctga       960
aatgacaaaa cgccagtgtc atttgctgtc acacagcagg agctgccgca cggacacttt      1020
cccgtatcca gggtcacagt gcaaggtaac catcagcttt tttactgtaa cgtcttcaga      1080
ttatgtattt gcaatgtcta tttgccgttc atgtccagga ctgttagtgg atttacaaat      1140
tcaatgcaga gctcattttt ttttttccca cttgcatgtg taaatccaag catgggttca      1200
aaggaaatct gacactggag ttttggttag atatctgata atgcattttt aaaatcctta      1260
aaaattaaaa cacatttat  ttgagcacac cttttcagag aaaaaaatcg ttcaaatatc      1320
atgcttgtaa ttttgaagga ctgacagagt aggtaagata caaataacc  acaatctgct       1380 gaatcagcta cacatgtaga ttaatgagga ggaaattaag acaataatcc ataaacaaca      1440
tgatttcaga gtagaggctg atcacaagct tactttcagt ttctttacta agttcatgta      1500
tgcacgtttg ttctcttctg atcccccggg ggaagcactt gataggtcag aagccagggt      1560
tccattgatt aaaacaccca gcatgtcaag aaccgttgtg aataattcac tgagaagaaa      1620
gaaaacccca ttttattctc acaaacaaaa cccggacaca cagaattgcc taagcatttc      1680
tactgaaagt gctaagtttt taatgacagc taaatcagta agtggcagaa tttcctgtca      1740
gtagacaaaa gcttgtacca tgcatgcatg caggggaaaa aaaaaggtat aaaatgataa      1800
aaaacaaaat aaaacaaaac aaaaacccaa catacttgtt agtgtgcatg tcaacagttc      1860
ccgaagtaat tatctggagg agtaggaggg cccagtcggt ggtcccctgc gtgctccgct      1920
gtaccgtgtc aaacattcct cctacctagc atacaaaata tgataaagat tttgtattgc      1980 taccccctatt accatatgtg cccaaatgtt gatttgttaa accagaagtg atgttaagaa      2040
ctggttcttg ctagccacac tatggattat cctacaactg tctcttctag ctatgtggtt      2100
atcactgttt atggttcttt ccacagaggc taggcattca aaacttaaca gaaagtgtaa      2160
cacttgaatg tgggcagtca caaaattacc tttctcttct catcagtctc tcatggtact      2220
tagttttaga cataactgca gttaaacctg aatagcatca aaactctgtc tcatcacctg      2280
caattgtgtg atattcgatt attattgcat ctgagcctgc cactataata tccctggaga      2340 tgcccttaa  cgtggaagga atgaggagga gaagtattg  ccacaggtct gccagctcct       2400
gggaggaggt cagagtgctg aaggtgaggt gaacaactgc ccagggaggt cagattgcca      2460
aaagccagaa aagcaattgc ccagggcacg ttcaggattt gtcaagagga aatttaaggg      2520
aatacaaaac atgctgaaac tttcagattt ctgtaaaata ttcttgtgag atttgtcttt      2580 ttttttctg  atcaatttaa cagaatgtct ctgagaaaaa ttgagagttg acagatttct      2640
gtggttgtaa aatagaacac agtgaaagcc aacactccta ttaaaggttt gtcggacctc      2700
```

```
cccttagcac tgcacaggag gaggaggaga gatctgccag acggagcctc tactccctgg    2760
tggaaaacac aaataggtgc ttacaactct actgtctaga attcaaccca gacaggaagg    2820
acggcagcta aggaaacaga aggtttaaga gaaaaggaag taggtataga gtgagaaaga    2880
ggaaggcttc cctctgtcat gcagattctg tccacagatg ttgaaagctg gtattacttt    2940
cacacagaga gaggtgtgac agaaatgggt ctgccacatc cttaccagat tcaggcggag    3000
ctgtagggcc tcatgcatca tctggcgggc tttcgtatca tcttggtatc tttcttccct    3060
ccagttactt aaaatctaag attgggaaca aacaaagaat aacaacagaa atcccttttgt   3120 tctttgctat gacgactttt acaggtttaa aatgaagctc tacagtaaca gctaacactt    3180
cttagcttaa acattaacaa agttattttt ttttttttact cttcctcttc ttccagacag   3240
acaaaatccc agttatttta aatttcctg ggtagctggg agaagaaagt cttacacaca     3300
cacacacaca cacacacaca cacacacaca cggaaaaagg ccacacagaa atgcctatgg    3360
caaggacaaa gggaggcaag gtgaactgag actcgcagaa aggcagagca ggtctgctta    3420
acatctgaca tggatccttc caggcaacaa aagaaggaag tgctcaggca cctaaaccag    3480
gacactggcc cagcccagag cggcttgaag gaaaggataa acccactgga agagacagca    3540
aatgcccaat caggagtggc tctatcagtt cagccctggc atttgtagtc taggtatgaa    3600
gagaaccctg agtgctttgt atttaaatgg ctccctctgg aagctagaca gagaaaagac    3660
ctgtccaaag tgtgggtgtg gtgacaaagg aaaccgagta agcctggtgc cattgtgcat    3720
gttatcagct ctcatttaat gccaccgggc agggttcacc tggctttgtg tcaggataat    3780
ccaactcaca aaaccaatct gacatctttc cttgattcct tgcttctcgg taggcgcaac    3840
agagatcggt aagctagctg ctaagcagtg tgcaacaact tacttttata gtctttacat    3900
atctctcaat gcataattag catcagcttt gctggccttc tggtgaccat gatgctaggc    3960
agaatgggac atggactgtg tttcttagca tctcagcgac agaacattaa tctaatgtca    4020
cattaggaca ctatcatgaa atcacaaaag ggaataatg aataccatca gaaagatact     4080
ggccgagttt agtactccac gctttacctg attgacttga ttctgcagag atgttagaag    4140
gccttcccgt tgctcatctt gccccttaag gcaggtaagg accaatgaga ggaaaggctg    4200
ctggctcaaa agagacatac tgcaaaggaa gtattaacag agctagtcag aaaaaatggc    4260
ttgcccctgc tgcaacagct gctctttcta gtagactcac tcactgctct tgtttattta    4320
cgactacatg aaggacaggg tgggaaacca ccagagaaca tttgggaagg tgacaccttc    4380
ctgtactggc aagattaaaa accactggta aagcttttaa atgacaattc tctattgctc    4440
tggaaggaaa tcccaaagca acagaaacgt gcagggtatg tgatgagctt gctttctgtt    4500 actagggga agtttttaaa tatacaggac aaagaatata aatgtatgca gagaaaaaca     4560
aaacaaagaa caaacaaaaa ataccggaga gattgctcag agaaaactct tccttaggaa    4620
gcggctctct gtggaccttg actatttccg aggcctgtgt ttcttggttg tatatttctc    4680
aaaggccaac agcagagtgt tggtaaagtt agggggagc acaacaaggt ctgaggcctc     4740
caaaaagcaa gatacttgct aggaacaccg tgtgccaggc ccgacactg cccatggcct     4800 ccgctagaaa gggggcaaaa ttctatttac aatgttcacg ttaacaagat atctcccatt    4860
agagaacatt ggtcaaactg attgatatag tgaaagaaa attttcctaa agaacaggtc     4920
tatgccagaa tgtctgaatc aggagccctg taggtagcca ataaagaaca ctcagttgtg    4980
gtagtattat tagctctatc tttaagttta tagaatgaag aaattatgac ctttctcttt    5040
```

```
aaaacttctt gggtttcaaa tgtatagtat gaatattcat cctcaatacg agatgatctg    5100
tttttcaaaa acaatgatgt gaaaccattt cttgggcatg aaataatgaa atagttttgg    5160
cagttgttat ggctagtttt aatcaaaaat ctacaacaag gttcctaaat taagaaaatg    5220
aaaatcagta attatttcaa ggtctagcag gtcagaatta acaacaagcc tgtgtacgtc    5280
aatagctttg cagtgatttg gacacacagg cagggatggg acctggtgcc ctatacagat    5340
ccttgctaaa cagagagttg gccgttctac aagcccacc ccgtggagct ggctgcgatg    5400
tgactttgat ggaggcttct aggcttcctc cgggtccttc ggatgccagc cttgacgcga    5460
ggcacctgcc agcgtacctt ttctgcttct gcctatctct ttccttcttt gaagaggaac    5520
ccaggtgctg cccttctcc agctcttccc cagcggcttt caacactctt ccctgcacag    5580
atgttggcag cctggcgatg agggggggcca ccagccacac accctgcgt tcagaggaac    5640 taaaatcaga acaggcgtt acacccgaga acgcagctgc ctctgctctc acagacgatg    5700
cagatgccac agtcaaacac cggtgcacaa ggcacagact agagttctca tttcatgtct    5760
gcactttctc cttttgctaa agaccaggca tttgcttacg ctttataccc acatctgctg    5820
aggagtaaaa ggtgctcttc tgggaaggca ttttttgcat tgtaaactgt tttcagtgac    5880
tcatggatcc tgcctttctg accatgaaac accatatgtt ctctctatga acactatacg    5940
tttcagtcat ggtgatgata tgcaatggga ttgtgttcaa gctaaggaat aagcgatctt    6000
taaattctaa aaccccctat ttaccttta ccaaaatgat gacatgaaaa ccaatctgtc    6060
tttcatgatg aaatacaaat tactgtattt gtacaaaact atcattaaag acacatagat    6120
agtatgttat gtttagtgaa tgacccaaag acagagatac cacacatcaa acttaagtcc    6180
atctgtgtca ctgaggtacc tggacctaca acaaaaaatg taacgtgcca agacatcact    6240 cacccccactt ttccctccta cctggctgag taacagaaac tgtcacttgt aagttattat    6300 ttccccttaca tttcctgaag cttaataaaa aatgaattat gctaatcaag gctattgtga    6360
catatgaaat atcaacggta gcccaacaaa actataaata ccttaagaat gtctttattc    6420
cattctgtct tgtgctactt ggatcaacac ttccaatagt gtttggttg aagaggctca    6480 tgccagaatt ggaggcatta ttatttaggt ctgcagattg ctggaacact tctatcgttg    6540
cctttgcgat attgtccagc aaattattca tttcggccac agaaccagag ctctagtatc    6600
aggaaaaaga aagctaactt gtctacacac ttcttgattt tcaagcacca atgacattct    6660
gcttttctat tcagttcaca cgtgtgctgt caatatatac tcacagggtc cttcaagcac    6720
tgtttgatca tgagctggag ctccagccag gactgtctca acgtccactg ctcaagattc    6780
tggagaaaat tcgaagaatt gtcacatttt gaatactgaa tgtatgctaa cacagcctta    6840
cagtaattaa tactcatacc cagcaaggaa actcacaagc cttaaagact tccaatccca    6900
tgcctgataa aaatgaacat gcacaacaaa gtagattcaa gcatcaaaat acgttcacca    6960
acaagccagg aagtagaaat cagacaagta tggcttctct cagaatccat ttaccaatta    7020
gccaacctca ctccaaaatg atgaatctct taaataacac atttaaaatt gagctatcat    7080
aaatactatg tatcaagtaa atataccact gacttaaaat acaatatatg cccttttgcta    7140 ttgactgtat ctactgagta gccagcagtg gcaatgtcac tgtaaagaaa attacagaat    7200
aaaacaaaag tcagaattaa aatcaaggtc aggagaaagt gggcagcctt gtctagtccc    7260
tgattttagt gggattgctt ccagcttctc tccatttact ttgatgttgg ctactggttt    7320
gctgtaaatt gcttttatca tgtttaggta tgggccttga attcctgatc tttccaacaa    7380
tggatggatc acagggctcc caatggagga gctagagaaa gtagccaagg agctaaaggg    7440
```

```
atctgcaacc ctataggcgg aacaacatta tgaactaacc agtaccccgg agctcttgac    7500
tctagctgca tatgtatcaa agatggcct  agtcggccat cactggaaag agaggcccat    7560
tggacatgca aactttatat gccccagtac aggggaacac cagggccaaa aaggggagt     7620 gggtgggtag gnnnnnnnnn nnnnnnnnnn nacggggtcc agtatcagtt ctttgtctgt    7680
acacagtcgt tctggttctt ttaagcagtg ttctcccacc cattcctaaa aacaagccgg    7740
cagttagact ggcacacaat gattctacct ggctgttgat tttattctca tttctcaggg    7800
taaaatgata aaaggctagt aaagacaatc taatgaaatg aaattaatga aaaaatggg     7860 tggagaaaag ctggcatgta gatatatgct ggttcttttg ttattgttct attttctttt    7920
gagacaaggt ctcaggtatt gcaggacggc ctctaagtca ctatgtggtc aagaataacc    7980
ttgaactact gatccttctg ctctgtccag tcctgggata acaggcctaa atttaatgcc    8040
atgtcttcct gcctaccaga gctccctgca tgttcagcaa gcactcttta tcaaataagc    8100
cacattgcca gctaatggaa aaatttcaaa acaaaattat aacacctgac atctttaaaa    8160
aaaaatccaa ggaggggagg gcttgagtta aaccagaaac cacttaaatc tgtgggacag    8220
agttaaaatt tgggattttt aaaaaataag gacttactct aaggtactat tttgtaacca    8280 ggttttttgtt tatttgtttg ctttgactta atatttaggg acaagaattt catgctttat   8340
ataactttca taattcttat gtgatatatt ctgctaaaca ggtaaagtgt ataaatactt    8400
agaaggttac ttcttttgac actaacatct ttctttagca tttttttcttt tattaagtgg   8460 cattaagaaa ctatcagtat cagagctcaa tctgaaccca aatctgtttc agatgaagta    8520 agtctcccctt tacactgtgt cagctgctca gctccgggta tttactgaag ttacataatc   8580
ccatgttcta tattagctgc attaaatcaa cctcagacca aggcacccag atgcagtgtg    8640
ttgcttttct aggtatcaca ttattattta ctggcaaact gattaatgtt ttttgtttttt   8700 gttttgtttg gggttttttt ttgtttttttt ggttttgttt ttgttttttgt ttattggata  8760 ctggcactgt agggcaggcc agaggcttcc ataggggctt gcagcagagc ctcttgggac    8820
actaaacctg gccagctcca tctggttcca ggcatctaga gaaccataca cagtccagtg    8880
gcaccactgt gtgctgacag ttggggactg atccacaatg gccatcaata gctgtaatgt    8940
cagttaaaca ccacagtgaa aacaaatgta aggaaccgtg cacttaatgc acgctacaaa    9000
aatacgtaat atacagcatt tttaaaataa agatttctg aaagtatgga aagataatca     9060
gaagatactg aagctagtct tcggagcaga gccagatagg gagaaggcaa caggtgagga    9120
caggttattg tgtgcacttt tatgagagct tttgaaggta tgctatgata caaacattag    9180
atgagaccca aaacagacaa aacaaacaaa caaaatataaa caaagtaaat aaaagtgatt   9240
ctaattttaa agaaagaata tgttcaccat aagtgagaca actgtaaaaa acatttttct    9300 ttattttttcc cttcctgttt ctccaaataa tgtttgaatg cattatcgta aacccttcag   9360
ataaatgaac cctcagtgct ctcagagccc cttttcctaa tggtgcatgt ataacaactc    9420
tgaaaccatg ctagctgctg tatggggggac aaggcaagaa tgtaattact aatatgaagc   9480
gagagtatgt aaaaatacag ctttaaaata ttagattaga actagaagta tcaatatgaa    9540
tttataatca cacacatgca cgcatatgta cacatatgct cacacacgca catgtatgca    9600
aaggctcaca catgtgcacg cacagctctg tctgctggga gagttcaaaa acagtgatac    9660
tcgatagcag tggggattta aacccagac cttgcttttcc tcttttagtg tgatgcggcc    9720
tgtcatgtta cacattgcat gcgtgcctgt atgcatgtgt gcatacatac tgaacatgat    9780
```

-continued

```
ggataatgcc catgtgtgaa tgtgtgtaga ggacagacat tgatgtcagg tatcttctta    9840
gatccttgtc caccttatac accaagaaag catctcttag atgaactcag agcttaccta    9900
tttagtcatt ctctctagcc tgcttaccct aggatcctgt atctccattt ctgagttctg    9960
ggattacagg tgggctgcca cagcctccca gtgcatacat gaatataggg atctcgattc   10020
taggctttat gctagcacag caagcatgtc accattgatc tgtccctcag ccctcagact   10080
ctgctttctg agtaccagtc tcttcacagg cagaaatggc actcctcaga atggctgatt   10140
ataactatga ggcaaggaat atgggggggac gggtaaagta aggcaatagt tccctaaagg   10200
atagaaatat tccaattaca acaaaaggta ggatgacaga ttgctaatat gtcagcttga   10260
acgagctgga cattaaagaa gctataggca atgtgttata tatccacata gataactaaa   10320
taaataaata caaatgaaca acaacataag aagagtattt gtagagcata aactgatcat   10380
gtggaggaac aagaggaact cagaagaaaa acacaacatt ttgcagccgt catagtaaag   10440
actgagttag acaagaatca caagggattc ttatgaggaa tggggtgtgt aacaaggatc   10500
agaatatttg catcatctca gagcatcttt ctgaaggtta ctagttaact gagagcaaag   10560
catactaaca ctctagtgga tcctgaatct ttagatgcct tcatcaaagc taacattacc   10620
tactggtgaa gagggcaaat gtgtgcaatc agtagtggtc acctaaataa tatagtttca   10680
gctctaaact ctccccgact ccaatgacct gaagttaatc tctagaccct tatgcaactc   10740
taacaacact agaataaatc agaaaatccc ctagagatgg ggaaaagatt attgcaccaa   10800
agtttagatt atgattttta ttaactaaac tttggttgta acaagaaatg agaatgtaag   10860
tattcagaag taaagcagag aaccaaaaag agatgggaca gatactacca tctacttgtc   10920
aactgttgag aaaatacaa aatgtccaga attagtgaat ctgtataaag gatacactaa    10980
aagtctccat tatcacagct ctttaacaaa tttgaaatta ttggggaaaa aagggggggga   11040 atacttaaat acaataataa aaaaaatagt ggatagttgc ctccccaaaa tcaggtacat   11100
attcaaagta gaagccattt gaaattggat aagtacctgc tggcagatag tcctcagtac   11160
gtatctagca tattctctga gattggcagt ttctatggaa atacttttcc catacgattt   11220
tgagttctgc gaggtggccc aggcatcttc agcattccca tcacgtcgta aaccccctcat   11280 gccgaagtct tcattcttca tcgtgttgac attgttactg ccaattttgg catcgcctaa   11340
atagcagaat cacaaaatca aagtcacaga cattcaaaat attgtcccaa atatgtaata   11400
agcaaattag gctaggtttc agggactcga gaggtgtgaa aattgtcact tctacatagc   11460
cagttgtcca atgcgtagat caagaaatac ataaaaggaa acaaaaccat tggatatgga   11520
gaaaagtcaa agtcaaggtt cactccttct tttggtttac atgatttaat gctcttttgc   11580
tagctttgaa agagccatta cggatgacac ttaataaccc aaacacattg cgttcaccaa   11640
aacttcaggc atgcgtgtac tcaagtttat ctgagttata gacaagaaaa tctacagcat   11700
ccagcgtaga cctgacccga ccaaactcta atacactgag taagatgaag ctaagggagg   11760
tatttgtctc cccaaaacac tatgcaaagc aggagcatac ttggatgaaa taaaaatctc   11820
aaaaaaaaaa aaaagtnnnn nnnnnnnnnn nnnnnnnnnn nnnnnnnnnn nnnnnnnnnn   11880
nnnnnacaag caaacaacac ccaaccaaaa caaacaaaca aacaaacaaa caaacacaac   11940
ttaaaactca aggccaatcc ccaaaaggtt ttgactctgt tgaaaaaaaa aaaacaaaaa   12000
acaaaaaaca aaaccccaaa aactcttttc ttgggaggaa gagtaatcaa aatgtcctaa   12060
taaatgtcta ctctcaaaaa tcttagaagc agaggggcta aggctgtcac tcagtggcag   12120
agtacttgtc taccatgcct gagaccttag gttctctcct cagcaccatc agtaccacca   12180
```

-continued

```
cacattaact aagcagaaaa accatagggg taaaaataag caagacatct caacttacca    12240
atgtgttttc atacactcat catgtacctt aaaatataaa acctagtagc tgtacccatg    12300
agagtttatt tatttcaaca gcacttttca aaattagcag acacgtgtat tctctacact    12360
tagatgatgt aaatatctat ctctatttca agttaaaata ctatgcaaat taggagcaaa    12420
gttcacgata atagtcctat tttcctgtct taatatatat ttggtagcta agagttggga    12480
aaaaattggt taaaagcact agagtggata aggcaagagc aaaaattagc tcatttctta    12540
gaccccttgt agacctccat ttactttgga tatggggtac tgaagtctgt gtaactatgt    12600
tagaacctcc gcaattgtgc agaaaaaaaa ccagaatatt ctatgtgaat ctatgtgaat    12660
ctgtctaagg cttcactggc atataactgt gctgattata attttcaga ccaagaacct     12720
cccacattat ttgaatatct gaaaagtctg gcaactttac ttgggattag tccagttctg    12780
caaacaaagg gctcactgtc tagatgagac tcatcttgtg ggtgccactg aaacatgtgg    12840
tgggcattca tacttccaac ataagtttat tgaaaatata tttcttactt tctttgatga    12900
gacttaaaaa tatctaaaga taaatctaat tcctgtcttc atgaccccaa tgattactaa    12960
tcagtaaagt ggaccagctc tccttgccct ggctgaaatc agcagtgagt attggctgta    13020
taatatttat ggccctaagc ccattcttcc cccttcctag atctctctcc tatttttccta   13080
accagccatt tccatgatcc ttctcaaaaa aaaaaaaaa aatccaaaac caaggaaaga     13140
aaatctaaac aacataatca ataaaataac acaaacaaac aaacaaaagc agaatacact    13200
ttgtgttggc taaccattct gggcatggg gcttgctctg gagtgtggct gatataaata     13260
acattgtatt ggagaaaact gaaaagattt gtatattcat tttcatgtat attcttttac    13320
atttattttt aaaaggctgc tttataaaca ctgctattat tctttgccat gcacaaatac    13380
catttgtcaa gcaaggcaag gctatatttt tatctgtgtt atctaaggct cacctaaatg    13440
gaaacctgtc tatcctgtaa ttctgtttaa atcatgaact actttataac atgatgtggc    13500
aactattgtt tggttatggc caaaatgagg tacccaaagt taaaagtagg caatattgga    13560
gttctcctaa ttcaaatgct ttatggttta tataaaaata tcctgaggtg tcaccctgcc    13620
gatgaacaga aggcagcact attactcttg ttaaatgtgt accagtaaga atgtctaggg    13680
aatcttgggc actgtgaatt agaggaaaaa cctgtgcccc tcctgctgaa catcagcaat    13740
acaagcacca ttgcagctcc atttgcttaa taaaaacaat atggcagaga atacaaactt    13800
gttcagagtc acagcagatg gagaaacacg aaattaaaat ccagcttttc tttgtttttg    13860
cacctggaat ataatctggc tgaaacataa agcttttatt aaagatatga agtacaattt    13920
ccgtcagtaa ataaaggcaa acgatcctgt gggaatgagg acctgattta catcacaatg    13980
aagaagcaca caattataac caacacgcag tacttctatt acctttctcc cagggtcacc    14040
gtagttaaga gacagaatcc ttgaagtgcc cattacttgg gcttagggaa agccaaccaa    14100
ttttttttccc ccaggacaaa caagcaaaca aaagatatgt ttccattaac attgcttaga   14160
atttacagtg caattgcata tgccagcaag attttgctga agggaccctg tgatagctgt    14220
ctcctgtgag gctatgccag ttcctggcaa atacagaagt ggatgctcac agtcatctat    14280
aggatggaac acagggcccc caatggagaa gctagagaaa gcacccaagg agcttaggga    14340
tctgcaaccc tataggtgga acaacaatat gaactaacca gtaccccag agctcgtatc     14400
tctagctgca tatgtagcag aagatggcct agtcagccat cactgggaag agaggcccct    14460
gggtcttgca aacgttatat gccccagtac aggggaaagc cagggccaag aagcaggagt    14520
```

```
aggtgggtag ggaagcagga caggggagct tttaggatag catttgaaat gtatataatg    14580
aaaacatcta aaaaaaaatc tcatagctta aaaaaattac agtgcatata aattattttt    14640
gcctccactt ccggtgatta gccaagaagc taaaggccag gatagtctta ccaagcatca    14700
taattgcctt taagacagca aaaactgctc ccacttctat gctgttgtga gctgcagcta    14760
agaggtgtct atcacaagat gatcttattc cggggaaagg tttgcctata aaacaacaa     14820 caaaccttca gtggcctctt cattgccatt aaccaccttc tgcaatcatt cacagtcagt    14880
aagacttttc attggttgtt tgtgggcact taattgacat gtttgcatta cctgatgccc    14940
cacagaaaca ctgccagtat tcttacttaa cctttcctct ttaattatta ttaaaacaac    15000
gttcctattc ctcaaagaga tgtggtccaa agattagcag gattcccaca cagatgcatc    15060
catctctata tggaaatgat ttagcaccag acttcactaa taccctccat tgcctcagga    15120
aagataaata aatgagttgt catccgctta agctgagatg gcatggctca gaatcaacac    15180
agggtataca agagactgag acttcccacc agcacactat ttcctaacag cccaggcatt    15240
tttattgttt attaattcct cattttatt tcccaatata tccgcatatt acatcatgga     15300
aggtgccgac agcccttcaa tggcatgatc tcactcctcc gtcatgcgca gctcaagccc    15360
atgaaaatca gggaggaaat gacaaactgg acagctcact tggtcacagt agaaccaaaa    15420
gtgcccaata accccaaag cagagctttc tcttgaggcc agctcacctg ttccctgagg     15480
gaaaaagcag gcctgggggg ctctgaagag gtgaagcagg aggcggcacg tcatccttgc    15540
cccgggctct gcatccgcgt ctccacaagc tggaaagagg aggaggcttt aaaacaagct    15600
tcctcacaaa ctccacaaca agcttttcgg gtttgctact actaacgttt ctgtaataca    15660
ttaaataacc cttctgttta gtaaggccat tagttatatc gttctgaaga accttcatgc    15720
tgccttacac cccgaataaa gcaatggcag tttcctgtcc cagagttcag tgtcactctg    15780
cataaaacag ctactacagc tctaccatct cttgcaggta caatgccatc ccacaatgca    15840
cacatcctta aaaatggccc tttccctgtt cttaagaggt aacaggtgac taccaaccag    15900
gaaacaatag cagacgcagc tcaggaccag cttacctgct gctaggagag agggaagtgc    15960
gacgtgttgc acgacatctt ccagggagaa acactgtcgt gctatcagga tagcaatgaa    16020
agtagctaat gaatcatgga atgaaaggtc actcacctttt aagaaaaaca ttgacaggtt    16080
ttaatacccg gcatccttta gtgcaatatc aaagacctaa gagaatacca gcgataccac    16140
taagatctca aacctccata tgaaccatca gagggaaaag acttgcgatt atcttcttag    16200
gcctattgct actatgataa gacaaagcac gtttactcat attctagtgt tctaggtaga    16260
tgttggcctt taacctgtca gttgcatgtg catgcaactg agagaagaca acacaagagc    16320
aaaattgaga tgctaataaa aggtgtatca taactgatgc ttgccaatgg aatacatacg    16380
ccatttatgg gaaaggcagg aaggagaagg tgaagcctct agcaggaaaa caggacccac    16440
taacacctga accttctttc ctgtcacaac taatgcattt tttttttaat gagagaggat    16500
tcatttaaaa gaactctgaa agttttcaat tggctgctat atttaaaaat gaaaatgag    16560 agaaaggaag gggagaaaaa ttagttcagc tacagggaaa tctctacatt ccagatctca    16620
caaaatatta gaagaaaata ctaagagaac acaattacca caatagcaat cttcctagtg    16680
actggtacta ggtgcagcaa gtcacaaata tgtatttcag aaaaaaaata acttaggtct    16740
ttgttggtgt ggaaaagcag cctattatta atgtattttg cacaaataat atcttaatcc    16800
acggaatgtg gataaggagg caggcctgtc cattcagcac tgaagcagca gaaagaggaa    16860
ataagctttc agcattacaa ttgtcaagtt tcttaataa catatagagc tctgacaaag    16920
```

```
atcaccccaa gcaatgataa aggcataaat ggatagagaa tctacagaaa tgtttaagga    16980
acgaatatat atctctatct ctatctctat ctctatctct atctctatct ctatctctat    17040
ctctatctct atctctatct ctatctctat ctctatctct atcatgggtg caacatggaa    17100
gacgaggaag tcaaggaaca tgatttgggc aattattcca tcactctaca ggcatagcct    17160
gagaatactg aatatcctga ggctgcacgt ggattttctt atgcaaaaca acaaaatctg    17220
tacacttaga cttaagtgta tggtggttct cctcatgcat gaaacgtttt atgtactgtg    17280
gtgagggatc cacgctgcaa aaaaacgaag cagctgagat agtttaaaac cttagcttct    17340
agaaatcagg caacagggaa cacactggaa ttccttctgt tacgtctatt ttgttttgtt    17400
ttaatttatt gaatttgtgg tattgaacat cacttttgga aatagagaaa tatgttgctg    17460
tgttagagtt tagttaatta agcagtaaaa gatgggtaat agtaaattag taattgataa    17520
gttaagaaaa cttacatcca ccgtgcagag gacatcatta aatccccaca catgatttga    17580
agaacaacaa agagccttca gaaccccag ccactccgaa ctcagaactg tacagcaggc    17640
agttagctca gaggagaaat tggctatgtc atttatccta ggggggaaaa aaaaagaaga    17700
tagcagaaag tgaactggaa caaataagaa ctgattacac ctaaccccca agaaactgga    17760
ggccccaggg agtttagagg tctattggga tggaggtgtg gggtgtggag gaggtatagg    17820
gtgtgaaaca gtcggagggt ggaccaggag gggaagaaaa tctgaagttt ttttttaaaa    17880
aaagatttaa taaaaagaag gaatatatga aaaaaacaaa atgattacac atggtttgtt    17940
cactgaatac atacttcatt atcattaagc atcacttaga tttcaggata taataccctc    18000
ttgtatttat acaaggtata attatacaca gcaacatata attataagaa atgaattagc    18060 atattttga ttctctgaat aaaccttgtc tacaatttta cattttatag ggatcaaaag    18120
ttaaggacac aagcttgggg atattctatg agaaagatcc tggaatcagt cggtaataac    18180
accaggataa atagttaaag acattatgtg atgtaactag gcccaagttt atatcaaaag    18240
atagtgctgt ctttaaaatt agatatgctt ttcaaaatgg accaccaata aaaaatgtct    18300
acagccaaac caagaacccc aaagccatga tttctcaggc taagtgttta gttaggagag    18360
agtggggtag aatcagaaat tactaaagaa actccaaagc agctcgccct tgatagctgc    18420
tgcactcagg gaaagcagc tcaccggccg gcatcctggt gtcccatgca cacattcatg    18480
agggtgttgc acacaaagct gtaccggttg gcagcattgt cattgaggat cttgcccagc    18540
attgaataat tgatgcttct tgccgagggg ttctcaataa aatccatcat aaagtctgga    18600
tcccagcgta agttggaatt tgcaggcatc acattattgt atatggtctg ctttactttt    18660
gaacaggcac tactaaggtt agaaaacgac agttaaaaaa ggaaaaaaaa aaaaaagaa    18720 caaagcaacc aagaaaatca cttcacttac agacatgcta agtggcaact actctaagac    18780
tttcctagac catctatatc ctactattac taatagcaaa atctttgtaa accagcattg    18840
gtacaatatc tgagatagag taattgctta atgaagagat ttttaattta tagatggaaa    18900
caaaaatcaa tgtatttact gagccttcta acaactttt ctttcttaag agtagttgta    18960
aaatgttata acctaaaaat aaaaatgggt ccaattacac acaaggaaaa gttcagtgtt    19020
ttaactccga ctgtaagccc taaaccctat ttctttgggt gtagtatgcc cagtaatagc    19080
cactgtgcca aagctactgt gagctctaag ctacagctgg gacaaatgga ggtaaaactc    19140
cggcatctgt gtagctcatg ctctcctagg ggaatacaga tgatacattc tatagtgtga    19200
agaaacttac aacatgccaa atggagaggg ctaagttccc acctagctgg gcatgtgccc    19260
```

```
tgaacaagga agcaaacatg ttttaggaaa tgagtgtttt cagtgggcaa catctgaaca   19320
gatacggaat actggaaata agagaaatta gaatgtattc tccaatgttt ctctgcagac   19380
aagacgagca atggtgtgat cccaagcttt tgattccata tgagctccgt tctttgtgtg   19440
ctctagctgt gtacagtaaa tccacaagca gaaatccatt tcctgctcaa gagctttact   19500
atgtagtaca attttttgga ccaaaatcct ggcaggtgaa ggttctgtca ttggggtgac   19560
acataaatct cctctattaa actgcagaag cgtttcttct tttccttaag ttttgagatc   19620
tactccactc tgctgtcaaa ttcagacttc tctggagaac ctctctggcg ggcatccgag   19680
cttctctaac ctctgagtct ctgcaccttt cctttctaga ctctttctct tctttacccct  19740 acttcccaag aggagcctct ctgttttgat aagatgctgg ctgccactga gaatgtgttc   19800
tcattcttcc cactctctgc tgcccacgcg tggggaattg agccaaaaat tcaggcatgc   19860
tccttctgta actgtgtgtc tcaggaaaac ctgatagagt aatgaaagca acgcatgcct   19920
tgaggtcaga aaaacttgtt ttaaatctga gcttcatcag tatgtcaaaa ataatcagga   19980
acaatcattt gtagctaaag aaactcactc ttcttcccag gataacgaca attcaaaact   20040
ttaatggaaa aactatcaca gttttgtggc acgcagaagc tcaagcagca ggagatgtga   20100
ttagtgtgac ctgtccctca aatttcctcc ctacacaaag ttacagggtt ttagttaaaa   20160
ctgttacaat gtttaattgc tattgtacta accaaaacct cactgaacat gtagcttctc   20220
tgtctatgtt tttcctaacc tccaaactgg cctctgactg tacactatgc ccagagagct   20280
gcactccttt tccgtttcct gttgaggact gtgcattcat tatctgtgat gcctctgctc   20340
ctggtgttag gagcacctta gtccactggt aatcacttaa aaataaatcc tgtgctctta   20400
atgaactcac ttagaccacc tggtacttac aattgtaaga ataataggg ctgcccacca    20460 ctaaaaccag ggctgttgca aaaagcccta tctttgagaa gcgtaaactg aaaactcaaa   20520
atgaagcaat agaaggaaat gaagtatttt tattgttact tcattcaaat attttacaaa   20580
gggctatttt aaatcaaatg gtaacatttt gtcagtttta tttattaatg ccactcatat   20640
tttaccaaca gcagtgcaac agtgttaaca gtagtgtaga taaattgctt ttgtgtaaaa   20700
tacaatatta ttgggataaa agagaaaaat ataagctctt aggagatttg catcccatag   20760
aggagccaaa ctaatatata tatgtgtgtg tatgtatgta tatatatata tatatattat   20820
ggagagagag agagagagag agagagagag agagagagag agagagagag agagagagaa   20880
ggctagccaa tactgaggtt tgcagaatga ctgactgaga atgggttgtc actgaacaca   20940
aggctgccag caagcaaggc cacagacact gtgtaacaag gcataaggac tacacaaagg   21000
aagagagcca gagcagcagc aagtagtcag tgctccgggt gtgaggacca gaagtgggtt   21060
tctggagaca gaagagaata cactaaagga aggaacaca ggagagatgg aagccaacac     21120
atctcaatgt ccatcagagc tgtgagtttg atgctgccta gatgacaacc atgggtgcct   21180
cacaatcatc cctggttgaa agagtcacct cagcagatgt gctgagaata tgctatagtg   21240
agtctgagta aaggcaatga agccaatgag aaggactctg caagttggtc caagcaagag   21300
atgcctatga tggccgtgac tggggtattg aagagaggtc aaatgtgatc tatacatgga   21360
agtcagagct catggtattt ctaagcaaac tgaacacaga gcaaggagga gcaaagaaaa   21420
ccattactga catatcttgt ggatttcaat accctatgcc acattattc ctcctgtaac    21480 ttcccaacag gcacttaata tctggcacac acaatgctaa gcaacagatg aaaggaactg   21540
gagactctac aagactttac agacaaaaaa gtagagacac aaatgaaaca agcttgcaaa   21600
aatctctgaa agaatattca aagtgaggtg aaagcaaagg caaaatacag aatgtttgta   21660
```

```
ctcaagaaac tgtaaccata gttacacaaa gagcgatgtg cactaacacg aggctctaac   21720
ttctgcaaaa attaatttgg tataagctct gagtaagagt tctgagaaga taaaagtaca   21780
aagcttctaa cactaaaaac gtttggactt gttttaaaaa tgttccccaa gtaacacaat   21840
taatgtacag gagtaaaatt cttggcagga gaatggctgt catctaaagg cttactaaca   21900
agccggtcag ttgtccataa tcaacacacg tactcttgca tcatgccgca aacataggga   21960
tttatcacag tgtaactcag ttgagtaaaa acaggccatg caaataactg cttttaattc   22020
gtgttggtta aacggtattt agagaagtgc tagccttcca tttaaagctc attcatgcat   22080
gggcaaatga tttgctaaag actaaactga ttttaaaaag agaagaaata aattttaaaa   22140
taccaggttg ggaggtggta taaaattacg gatatagagc cttaaagaat cactaagaag   22200
ggggaagatt tgcaactttg tgacccagaa agagtgtgga agccaatgta gcaggaaaag   22260
cctgctaaaa aggcaagatg ggaacaaaga ggacatgaca caaaagcatt atgagacttt   22320
caaattttaa attatatttt aaatcaaaat ataagcatat gctagatttt tatcatgact   22380
tcaatatggc tcatctagaa cttctaaaag aatgtgaaat cttaaataag agaccctttc   22440
acaggtgttg tacagcttgc cacctaaaat cactgttatg tacatacgaa aaaaaaatct   22500
tgtactatta tcattaagta tttttagtatc tgtctaaatg agtctcgggt agatcaaaca   22560
cttcagattg gcttacatca gtacatagaa tataaaccac aatcagacca ttaacaaacg   22620
gaagtgtgat catgatggaa gtataatcat gtctgtaggt tttttttgttt tttcgttttt   22680
tgttttttta cttttttcctg ctcacctaaa aaggtctcca aatttacttc tgaggtggct   22740
gcaggatacg tagaggtcat agaggtaggc caagatacat ctctctgggg aagaacattc   22800
tgaggggttg acaacgtgct tcaccacacc acacaacctg aggacagaga cacaggaata   22860
aaaaagtcgt gtcttgatag tatgtgaata gtgagtaatg aattctttaa tgtctaccca   22920
gcacttagaa gtatgtatca aacataaaaa gaaactcgat tgctcataaa actatgaagt   22980
tattaaatat caatttttgt tacactgaat actagaaaag ctttaaaaaa ccctcagaaa   23040
catcacttaa aagaaacata tgtaatgaaa tgaattctcc acactgcaat taacactcaa   23100
aactccatca cttaggctga tttgactaga aaaaaaaaag aaaaggctag gcagagaagt   23160
ttaagtcaac acaaagtttc acaacttcca ttagttgaca tggactgcca agttcactag   23220
tttggaaaga agtaactctt cagtgcagga aatctgctga gtttgatgaa gccgtggttt   23280
ggaatcccat tcctcttctt tgtactacag acaaatttat cttggcttct tatgtacgaa   23340
gatgaaaatc cattccctgt agaggcatcc tttataataa tgccagcctt tcaagagtac   23400
caacaccaca gccactttct tcccttccaa accatggctc ctctgtccat acaagatggc   23460
catcagtatg gcatagaaga caacacctgt ggcccatcca tacatgtgtc tgactccacc   23520
accaccctgt atccgacaca ggactccaca taacatgtca cccatagtgt caccaatggc   23580
tgagactctg aaaagagttt aataatattc ttccatctta ccaccatcac tgcacaaaga   23640
aggctattag gtgacctgaa cagagaaagg aaagggagg ctgggtgcat agtggaccac   23700
tctccattat tcagaagata aggaagatca agaggtggta gtctgcaatg ttcaggccca   23760
ctagggacag gcattctcca gcatcagaca tggatgccag gaaaataagg aaccgcagtg   23820
caatatccca ggtagtctga aggatgtcac ctgatgggga acttggtaat tataaaggag   23880
gacaacatgc tgtttgtctg ggttacctca ctcgggatga tttgttgttg ttattattcc   23940
atccatttgc ctgcaaattt tatgatgtca tttttttttc taacagcgaa ctaatacttt   24000
```

```
attgtataaa tgtaccatat tttctttatc tagtttttgg ttaagggaca tctaggttat    24060
ttccagtttc tggctattat gaagaaagcc acaataaaca tagttgagca agtgtccatg    24120
tggtaggagg cagcatcttt tgagcatatg tccagaagtg gttcttgagg tagattctga    24180
gaaacaacca cagtgacttc aatagtggct gtacaagttg gtgctcccac cagcaatgga    24240
ggagtgctcc ccttgctcca catcctcacc agcatgagct gtcacttgtg gggttttgt    24300 ttgtttgttt gtttgtttgt ttgttaccat agtgattctg acagtataag atagaatctc    24360
tagatcattt tgatttgtat ttccctgatg actaaggatg ttgaactttt tttttctcat    24420
ttgatatttt tttttcattt gatattcctc tgttgaaagt tctgtttaga actgtacccc    24480 attttaaat tggataattt ggtttgttga tgtttagttt cttgagttct tttatatatt    24540
ttagatgtaa gctctcggtt agatagagtt ggtggatatc ttttcctatt ctgtagactg    24600
ctgttttgtc ctattgaggt gtgtactcac tcataagtgg atattagctg taaagtaaaa    24660
gacaatcacg ctacaatcca cagacccaga gaggctgagt aacaaggaaa gacacgtgga    24720
cctccctgcg cagaggaaac agaagatttt gcaagggact gaggggagat gggcatggga    24780
acaggaggga tcaggtgtgg gatggagtac taggagagag tactgggaaa gataactatg    24840
gggggggcat ttgaggggca aggtggaaat atagtgcaat gaaaactccc tggaatctac    24900
aagggagacc ctagcgaaga ctcctagtaa taggagattt ggagcctgaa ctggctatct    24960
tccgcaacca ggcaaggcgt ccagaggcag gactgggaca ccgatccagc cacaaatcgt    25020
ccacctacaa tttgtcttgc ttacaagatg tcctggggta aaggtgacac agaacttttg    25080
ggagtggcca accagtgact ggtccagctt aagagccact ctatgagaag cccacacctg    25140
aactgcctgg gtggccaaga accagaggct agatagccca gagacctagg acagaaccaa    25200
acacaactgg aaaaaagtag ggaatgaaat gattcctaag gataattctg ctattgatcg    25260
gagcctagca taactgtcat cagagaggat tcacccggca actaatgggg ccagatacag    25320
agacccatag ccaaagatta ggaagaacac ggggaatcac gcagaagaag aggagggaga    25380
aaggacagga gaagatagag gggtcaaacc attgcataca ctagcaagat tttattgaaa    25440
ggacccagat gtagctgtct cttgtgagac tatgccgggg cctagaaaac acagaagtgg    25500
atgatcacag tcagctaatg gatggatcat agggctccca atggaggagc tagagaaagt    25560
agccaaggag ctaaagggat ctgcaaccct ataggtggat caacattatg aactaaccag    25620
taccccggag ctcttgactc tagctgcata tatatcaaaa gatggcctag tcggccatca    25680
ctggaaagag aggcccattg gacttgcaaa ctttatatgc cccagtacag ggaacacca    25740 gggccaaaaa gggggagtgg gtgggcaggg gagtgggggt gggtggatat ggggactttt    25800
tggtatagca ttggaaatgt aaatgagcta aataccaaat aaaaaatgga aaaaaaaaa    25860 gatagaggga tcaagcacac cgcaagaaca tggcctacat aatcaactaa gcagtgctca    25920 tggggctga cagagactga accagcaatt aagcaacctg gatgagtcgg atctaggtcc    25980
cctgcatata tgttacggtg tgtaactagg tgttctggta ggattcctta tagcaggagt    26040
gcatgctatc tctgactctt ttgcctgctt ttgggaccca ttttctccca ctgagttaac    26100
cttgtccgct ttgatataag ggatgtgcct agttgtgttg taacttgatc atttgatatc    26160
cctgggaggc ctgctctttt ctgaaggaaa atggaaaagg agtggatttg gagggaaggg    26220
cctgataaag gggataactg ggaagagttg agggagggaa aaaaaataaa aagattttt    26280 aaatggaatg ttttttaaaa agggggggg gcaacaggta cagacaatgg aaccatcgtt    26340
taagagggaa gcaacacctg aatctgctgg gtatgcagaa gcaaacaaat cccaacagag    26400
```

```
catggaaagt aaagacttat cctgcgacta aagtaaacaa atgcaaatgg gtaggtgcgt   26460
ccatcttaca gtagttttca cttctaagaa ctaaagcctt ggactgtggt ctgatactct   26520
cagtcacatt aaggggggga ttgtgatttt gaaaaaaaaa aagtcatacg gtgtgtcaat   26580
agttaagaca gctatctatg tgacacaacc tgagtcactt gggaatgacg gggggaggg    26640
ggggggcgga cagacgtgct ttatttctgc ttcacaaggg gagggtccag tttcctgtag   26700
cctgtgccat ctctaggcag gcagacctgg gttgtatagg atagctagct gaccaaggca   26760
aagggagcat gccagtaagt tcctgcatcc agagtttttc ctcgagctct ggtcctggtg   26820
tgcttcaatg atacaactac aggctataaa ctgaaaaaca aacaaaaca aaaaacaaa    26880
aaacaaaaaa acaacctttg ataaagttga atttggtcac agcgtttacc gtagcaacaa   26940
cgagcaaact agggcattat aaataaggta aaatataac aaagttaagc caaatataat    27000
tttatgagta tttaagttaa tattttaaat gttaaaatat taaaacaatt tcaaactaac   27060
aatcaaagaa caaccaaaca aaaacacttt ttccaactaa gtatgtatga gttcatgatc   27120
agtgaatgtg ttgttaaatg aattattatt ttaaaattga atgattttaa aagaatagtg   27180
ctgaaaaaac agtaaggagt caacttcaat ttgcaacata tactagctgt gtaatgaata   27240
tggggcacat cacttccaaa ctcttcacct gtcgaacgat ataaaagagc gaggcctcac   27300
ataaatacac accttctctc actgtaaagc ttttgaggct tgtaatattc tacttcttaa   27360
gttagatgta catgtaaatc aaagaaaagc ctctgcaaag tagatgccac tagagaaata   27420
ctgtttataa attaaatgca tgtgtaaggt tacagagggg atgggtgaaa accaagaaga   27480
caaatgagga gacagaggaa taaagaatag gttgtctttt ttttttttta ataaaaggcc   27540
ctagaaatgc aggtgaggag caggcaacac gatgtttgca cagagctccc tgcatttccc   27600
tggcctttta agcacagcct cttgcagaca gttccttagc ccgactttat gagcgacagc   27660
agaagctttt gtccgttaga cactcagacg aacaactttc atgagtcaga agaagatgg    27720
ccaagtttct acagtgcaaa gaatccttgc agtgttgcaa ggactatgta gtgtctgatt   27780
gttttttcaa aagtacactg aaaatagatg accagatccc agtattcact gctcgcagta   27840
agttgttggg cggcataaat gagaagagag ctgtgcatga ccaggaggtg aagaggaagc   27900
cagtaagtaa gtaaaaaaa aaaaaaatc aaacacactt cctccatta tatctctttc     27960
tctacaaaat attttggtaa gaccattgtt gggatgtttt cattgaaact ttaataagac   28020
atctaaaact tcaaaatgag tggtatcaaa acttcagacc aacagtctaa acaaaaatac   28080
tttttttagaa ctcagtataa ttttttctccc aaatgcactg tatttcacta tgaattctac   28140
cttttaggat aagaaaaaca aacaaacaaa caaacaaaca aacaaacaaa aaacaaaaac   28200
attgctactt atatacccac ccttcaaaca cctgggctgt ctgatcagga tttaggatca   28260
ggcaactatg gtaccgcctg agcacggcca caatgcagac acatagtcct gtagtgtaac   28320
ttcctgccag gctagaagac ttcaagagga gctctgcttc caccacactc agttcattca   28380
gcagctgcag cagaagtggg gttgggggg ggtgaaggg agggttggag gggagggaag     28440
aagacaaaca gggaaaccgt tcagtgaacc cctagtgcac atttcctata cgctacggaa   28500
tcagaaagca cacaagcttt tgctggcatt tacttttaag cctttactaa tttaaacgaa   28560
tgttttttctg tctagacacc agcatgcacc caaccaggat gtagtcagtg ctgaaacagt   28620
caccaaaact ttctgaaagc ccagagcctg gaactaagcg tttaataaac accccatc     28680
tttatttaat tttttttcct ttttttcttt ttttcttttt catttggtt gttgtgcttc     28740
```

```
                                                            -continued
tttttttttt tttcctttca atgcaacaca actgataact ataataacta cattcttatt   28800
tataaagctt ggagtaactg tacaatagaa aaaaatcaaa cctaatgtct atttattaac   28860
acaaggaata aatgatctaa aatgtgtgta actacagtgg gacaaatgaa attataaaga   28920
gtattttaac aatcatttgt gcttttcact gcttaactct actagagaga atatatcatt   28980
tccttattcc caacgcaaaa taataaggta acaacaaccg acaccaaaac aaaaacatct   29040
ttcacgtata catagtttta aataagttgt gtattactaa caccaactat agcttaacag   29100
taaaactatt aactcaaaat gtctcaaaca ctttaaaatg tactaggtgc ttaaaatagt   29160
tttgttttat ttgttttgtt ttagggattt tgttttgttt tgtttttttgg ttttgttttt   29220 ttcgagacag ggtttctctg tgtagccctg gctgtcctgg aactcactct gtagaccagg   29280
ctggcctcaa actcagaaat ctgcctgcct cggcctccca agtgctggga ttaaaggcac   29340
gtgccaccac tgcccagctt aaatagtttt aatgtaacag aactggcaca tgttcaaagg   29400
catgaagttc caagaggcca aagagagttg ggacagagaa gtgattaggg aaagttaatc   29460
agtggggact aagttcttac aggagcaaga tatcttcacg tgtaatatgt atggcagggc   29520
ggctataggt aacaggatgc actgtaccta gcaaacgtag ggaaaaggac tcttgacagt   29580
ttctaccatc aagaaatgat gtttgaagaa taggtatgtt taatttgcta taagaatata   29640
cataacatat acatgttttta tggcatcata tggtatttca taaaactaca ttttttgcata  29700 tttatgcaag tttaaaaaat aagaggcttg agagatgact cagtagttaa gtaccactag   29760
ctgctctttc agaggaccca tgttcagtac ccaacacccc caagatgtct cataagtatc   29820
cgtaacgccc ttccaaggga gccaatgccc tcttttgaac tctgcaggca ccaggcacac   29880
acatagtgca catctgtagg caagacaccc atgcacataa aataaatcta aaatatttc    29940 atataaatgt aagccaggtc acaagcttgt agccttaggt acttggggggc tgagtagggt   30000 ggtcacttca gatggaaagt tcagacaagc tcaacagtaa gggatagcct ggttttttaaa  30060 tcaacaaata aagagtatga agaagcaaga taaactctag tgtctggttg gtttgctttc   30120
ctaaatgtga gaaaggcaca gtatagtctc tgtggcacct gtatggcaaa gtcaatcagc   30180
ccattgatgt tcagcgctgg ctccatgaga tcaaagatga gctgaatatg gtgagccaac   30240
gggaggtgat aggatgttcc agacgcaaag cttgtgattt gttccagcac attgttagag   30300
atctgctcag acaaaagcaa ggaaaatcac acaaccaaca gtctgggtga ggcttcactt   30360
cgatatatca cttcgattgt tttcgtttta ggttttttttc cagcaacaca tatgaattca   30420
tgtgattcta cttagaaatt agtatttccg tggaagtcaa aacatataca aatcagcatt   30480
cttacaaaca tcatttgaaa atttcaatat aatctagata ctggtgaccc caagggaaa    30540 tcactcaaaa gtgtgagtca tcagaaactg acatgttaac tgaataacaa tggatttctt   30600
ctaaatttcc cagtatttta attaaatcat caaaaagttt ctccttcacc aatagtgatg   30660
ctgggtcagc atgttatata ataagtatat taggaattac ctttatgaat taataattac   30720
tataaagcaa aaatacttac ataataaaaa caggtgttga aggaaacacc taatactcac   30780
aaatgaagct tgttctgctt ccaagtctat aagggtcatt tgtaaaagtt aaggctggaa   30840
gtacactgct tgagctttta agggaggaat attcaaagca tgtgacaaac agccctgaat   30900
ggatacctga gatgttactt gatgctgatc gaagtatgag aggagttgga gtttcgtgaa   30960 cacatttttcc ggggttggaa aaacttcctg cttggtcttc ctggctttct gtccttcgtc   31020
cccaactaaa gaaacatcag atgtattact ttccatttaa attaatctct tcatatttct   31080
aaagattttt ttgatgtgtg tgtgtgtgtg tgtgtgtgtg tatgtgtgtg catgttcact   31140
```

-continued

```
tgtttgtaca cgtgtgtgga ggccagaggg aaatacctgg tgtcatcctt caggcaatca    31200
caccattgga gtttaccctc tctgatggta ctctacaaca gagtctctta ctggccaaaa    31260
ctcaccaagt gagcttgcct ggctgtttaa ggaacacaag gggtctgcct atatccatac    31320
ctccacagca atgggattac aaccctgctc catcatgccc agctattttt atgtgggact    31380
tggaacgtta ctgagttacc tccccatccc atctttatat gggtattttt tactgaagta    31440
tggcacaata atagatgaaa gcaatatata ctctatgcat tttgacaaac agaatgagat    31500
ccaaatcgtg aaatagtacc tcaaaagtcc acctacctga ctctaatctc ctctccctcc    31560
ccaaggggcc aaaggtttgg acagcttcca tcgtgggtgg gtggaaactt tcactcaaca    31620
ctatgtttta agatagcctc attatttagg taattttaat gtgtactaat tgttagtaat    31680
tttcacatac tttattccaa tgcataaaaa tatgccacta cttattcttg caaataatga    31740
cttgattctg gctattataa agtgtctttg caagcattca tcattaagta actttaaaga    31800
tatagtaatg aatcaccacg gttgggtggg gaacaccaag gcccactgtg actaaacagg    31860
atacattaca ggcttttta aaaaatatgg attatttatt tattttgtat tcatatgcac    31920
tcatcaggga acatttcggt aaaccaagaa aaatttaagg gtgttctctc ctccagacat    31980
caaattcaga ggatgaggct tggtagcaag atcctttgcc ttctgagcca tttcactgac    32040
ttttagactc acctctgtac ttttataaat cagtaaatat atgtatattt ttgcttattt    32100
gaggaaaact ggttttctta acaactaaga gcaaaattaa agtctctgga acaggatttt    32160
catctatgta tatacaaaga caaattttta atgaaagta atggttgggt tacagtactt    32220
ctacagcact gtgcgccatc tggttagagg gagcactcca actcagtttc atgtgggaat    32280
tgttagctca gaaaacaaaa tgtttcttat tgctctagag gttggcaaga ctccaagctc    32340
ctccacatca aaagtggacc tcccttgaa cagtaagtga gatacaaat ccaagtgagt    32400 tgtcacgttt ctgctttgta caatggatgg tgataccaga atgaacagag tagtaaaaag    32460
agctggtact gggcagggga gatagcacgg ttagcaaatg gcttgccctg caagcatgag    32520
gctctgagtg cggaatccag aacccatgtt taaaaaaaaa aaaaaaaaaa aaaaagcta    32580 ggcgtagtga caccggcctg cgatcacagc ccctgggagg cagagatggg acaagtcatg    32640
cttcgctgag ttcaagcca ataaaagacc ctgtttcaaa gtacaaacaa cacagtggag    32700
gacactagaa gaatgacatt tgagtttgtt ttctgaccct ccatgctcac atacattaag    32760
gaagtgctgg taaaacacat gacaaaaact tccttctgtc attagacctc cttctcttcc    32820
agcatctatt ctcataagca caagttaaac gtgggatgag gccttctctc tcactgctct    32880
tatatgtatc ataagtatag ttgagatacc caagttttga cttagttttc aattccctag    32940
aatcattgct ccaaaactga aagggtccaa cctactactg tcttgtgttc atattaatca    33000
tttagtctcc cttggatcga aataaacaca gaagacttgg ggaagtaggc ctagctcaga    33060
actcccaagt gcatttttcct ttgctcattt gtataaacag gttccattac tgaacatgta    33120
aggtcataaa agctcaactt gatataactg ggtcttgtaa cctagaaagg aaaccactga    33180
taactaatga tgctttgaaa tgaaagattt cagtgtcgtt tgcataagta acaatacact    33240
ggggatataa agaggtttg ttttgtattg ttttattctt ttgcccgttt ccttgttttc    33300
ctggcatgca ccactgctct ttcaatactt aatttttaca taaaaaaatt aagcctttaa    33360
attctgaaag tattgccctt tttagacaat gttatagtga agttgacatg aaatttggct    33420
gtttaactgg aaatagtgtt taagctttaa gttaggggag cagaggttgc tcaggcagca    33480
```

```
gactgtctgc ttagcatcac acaggcctga ggtcaaccct tagcagcaca taaacaggca   33540
tggtggtggg agcccataat cctagcacat gggagacaga agcaggggga agagactttc   33600
gggttcatcc ctcaaattcc agcctgcctg gaaaacagaa gactccatct caaaaagaga   33660
caaaacataa caacagactt ccagttacaa atcccctagg ggaagactgg ctggttctgt   33720
aagtgtccta aagggttctt caaaagtcta attttgtttt tctcaacatt aaagcacatg   33780
ctagtccaag ggatagtttc cttttttcct ttccaatctt cacattgcta agtaaagtag   33840
ttgtgtgtgt gtgtgtgtgt gtgtgtgtgt gtgtgtgtgt atacaagttt cctgtagcct   33900
caaatacagt tggctaactt cttgtataca aagtcttaaa taataactta aaatgaagac   33960
tgtttaccaa gtggctgtgc actgtggctg agattaaatc gaggaagatg tcagtttgaa   34020
gtggtgtttg tgtgactaat actttgaaag cccgcacagt gaatatctct tttgtagtcc   34080
atacggaaga atatctactt aaggggttgg cacaaagaca aaacaagact agtttggcat   34140
taaagcaaaa ctgtgaagga aggaaggaag gaaggaagct tgacagcaag actgcttctt   34200 tcccttccc acttcctttg gtctttctcc accataaact tcagaaatct gcaaaggccc   34260
tctacactaa tttagatgaa ttaagcgtga ctgtgcctct tatagacatc agcacctccc   34320
accgcattcc aactcccccg aaagctactt caaatgccct tggctaggga cttgtgagcc   34380
ttccatattc aggcttctat cgcaacttat ttcctgtttt ctctgaggga gaaaaaaaat   34440
agcacaagga gagttttctt agacagagca gtttcttttt caagctcaat gagaagaagc   34500
caacagaaga cagtttcatt tccctttctc ggctcttggt tgcttcttgt ggcgctggca   34560
tattgaaggt cctaaacagg caagggaagg gagccagggg tggagacaga tcacatgagg   34620
gcaacttccc cacagtgttc tccaaagccc atccagcaga cagcctgcgc tcaggtaggc   34680
ttacccatgc tgatggcaga caaaagttac aattgtttcc acctgtaggg aaaaaatcta   34740
gcatacacaa acaagcccta ataatgcacc ccattaacgt cataaaaatg gaaaggttcc   34800
taggggtttc tactcaagta ggaaaaccag ctgtgaacat agggcaaacg caaccctgtc   34860
ctccttcata ggaatgacca tgctagagag ggagcgagca gtggcagggc taaggtagaa   34920
aatgatgcca tgtttaaac catgattatg aaatgacgta aaccttaaag agagtaacta   34980
ggcaaatatg ataatagata atagataatt ataggacttc aattatgcaa cacaatgacg   35040
cactatgagg gccaagctct gaaagaaaca acaacaacaa caacaaaaac atgtgagaag   35100
aacagggaaa gaaaattcca agtcaaaaag atcaaattgc ctctttcact tttctgtggt   35160
gacagactta gccatggcta ctatggcaat taggttttgg ctaatgtgga atcagcatct   35220
atatgatgac ctgccactca tgtgaaacac agagcaaaaa caatggtgc aaaggaaagg   35280 tgaactggct gtttgcaggc agagtatttc tcctcctcgt cactcagaac atcacccaca   35340
gcaatgacca tagaaagctt ggcacccaga tgacaaagta caaatctcac ctgtatctcc   35400
ctacaaaagg cggtcaatgc gaatgctact aataatgaac gcaaggcctt agagtgtaaa   35460
tgtgcctatt catatttcag tgtgacagtc attcatgaga ggaaacactg gggacagtga   35520
catggagcgc tctgataagg cctgtgggca gagggagcac aaacgcaatg ggagccaggg   35580
cactgaggcg ccttaccccc tgattctgtg gtgcccttct tgttcaggat tttgaggata   35640
tctttggtaa tcttcttcag ctgatgcctg gcttcatcac gctcttttcc gactccatag   35700
agaaggattg tgcgctggtt acattcatga cttgaagatt catcctgaaa aacagcaaca   35760 gccctgaaa ccagtttgca gagctggggg tacatttct tctcctgcac cacactaatc   35820
acatcctttc catgcctgct tgcaggggtg gcatctacct gcttggcaac tcaccttcac   35880
```

```
cggcaccacc cctgtttttc cagtttggaa catgctaaag taaaataata acgtgctacc    35940
cgacctgaag cacttgatgt gggcgtaccc tacagagtaa gttctggctg ttcaaagact    36000
ttttgttgtc gctgtcgtct aaatttgacc atggcataag atgatgttac tatgtcctta    36060
aggaaaatgc catttcctta gtgagcttgg tcttagatat atggcattag catgtgtttt    36120
ataattagga aaaaaaatat cttgctagga ccttcaagca tcttcagaaa aaaaatgtac    36180
gacacttacg tcaacatgac cgtataaggt atattagtat ttatttccag atgacaaaaa    36240
gcaaagtgtt gggatcacta ggcgtgagct aagtggctag gaattcagaa tcggagatga    36300
tcgagtgagg ttttagacct cggtctcctc taatgatcac tgcaaatgca agcactcctt    36360 ttttccttg tgtgaaaata aatgacctga gtaatgggca ggaatccaac acagaactcc    36420
atttaccttt agccaaatgt aagtatccaa ggcagagcct cactcttatg actgccttaa    36480
atctctcagt gctaatctct ccctgggatc ttttgttttc cattttctga gcaaagttat    36540
ttacttttct gttggacctt tcaatatacc tcccccttttg tcattctttg tataaagccc    36600 tctaaaggc atcacctctt atcctaaaga actcctccca gggaaaatgg attgcatatg    36660
ttcaccatta ctgatggctg caactataga acgaaccctt cagaagtggg ggagccacag    36720
tgacactcac tggtagaact ctgtgtgtcc tgtgaacaca gttatcagta ccatccttct    36780
gcagctgagg aagcaccatg tccactctcc aattctgtca ggttttatat ttccttgaag    36840
tacacacttg ccttcaggcc ccaactcagt taccctagtt ttattttttt atatatatac    36900
agtgctagaa ataatacaca tatttgcata tcctgttgac ttatctttct ctaccctct    36960 gctaattctt catgttccaa gtatttacag aggcctacgg agatcctaac agggatggtg    37020
agagataaaa gatccatgta ccaataacaa ctcaagacag ccccatccca atagtacacc    37080
atacttaggg aagaaggagc tttgtaattt atcctagtca tgacattcaa caccccata    37140 ctcctgagta ataataagcc tagtaccttg cctcagatcc ctctcctgaa acagtgtga    37200 tgccaccttc catttaagga tctgtgagaa taaacaagac ataacaatac acgcaatgcc    37260
caagagtact gtgtacatac agggtgctca ctcttcacat tatagactcc cattcttcca    37320
catgcatcca gagtccacac tgttttgcat tagccaatac ctcccataac ccactatgcc    37380
tttcctgcca tctaagatgc atgatttcaa tggctgacat ctgtctacag gtgcagtgtt    37440
atggccccat caatgtccac agcacatggg gattaggaaa ggaaagaaga gtttgcagca    37500
ttcatcagac acaattcagt gattttctag gttattggag aagggggtggc aggcatcaat    37560 ggctatcttc cctgagtcct ctatttattc tcttttgtaa gcacaaagtt ggcaagcaca    37620
gcaagcacaa aggaagccag tagactaagg aacaaactca tggacagaag acagagggga    37680
agaaaagaag acaaaaatca ttgttttata ggaaacaatt aggttgctaa agtgctgaga    37740
agactgaaga agtgagagac aggtagacag ctcatgtctg tgtagtgcat taagtcttag    37800
ttgtgaggat gaggaactga agcagaatt tcagaggcac ttggggaaga aagagtcag    37860 acattagggt ccaatgagtg aacatgcatc tctctgaatt tcactgatcc actttgaaaa    37920
agttgttgga gaaaaccat gaaaatgttt agttttttt ttaaaggaa aatgtatagt    37980 taatatgtat ttagtgtgat gtagaaccaa tgcaggtcag aagtgaggca gtaagggaac    38040
actgagttct gagggaagtg caaaccatcc acatcctaca agaacagtag gtaggtagct    38100
aaggtagtgg ggaatacaag caagccatta aatgatgctt atgcgtgctt cttcatttac    38160
taggatgctc taaccataca aagcctagaa attaggcagg gagacacagt aataggaacc    38220
```

```
atcaaccaat gatccaatag gtaatagagg taaggagtca gtttagatgg gatgtctttg    38280
ggttttgtag tttgtggttt ttcttttgat ttgtttgttt tcataaaaac acctgaatgt    38340
ctcaaaagag gagtttctcc agactagttg tgaagatagc acaacaggaa gtgatggggt    38400
gaagtaacgg ctactatgac aggagtaagg aacaggggt ggcagagagt ttactagaag     38460
ctgggcatga agtacaaatg aagggaaaag agaaccttga cttgggtaat aagcaggaaa    38520
tccagtttca aagatatgac acagataaag aagtctccat agaggacatc acgtttgcag    38580
agcagattac tggtaagagc tgggacacaa tggagtattg tttcgattaa caggagagac    38640
aaggacactg ctttacccaa ccacagggaa tggggagaa caaactaagg aaaatagaag     38700
tatggagatg aagaagtgag aaacttcaaa ttctaattag cctactgatg tccttgggca    38760
actgagccag gaagcacagc cctgatggag agagatgaaa ttgagccact ccagatcagc    38820
atgcaatgaa aagggaggga tttgccaggg agaagaccat actgacttaa tatcaggaaa    38880
atagtagtaa cgattactgg ctttccacca gcaagggaga gacattttga agttcccagc    38940
aggctaaatg attcatttat gtctattttt ttgtacaaat agaaagtgt acaaaccctc     39000 aaactgaatt gatcagataa gcagctcaac ttacaattat atattaaata cttgcaaatg    39060
tggcagtgga tttctactat ttcatcttag catccccata ctgcattctt tgagtaacat    39120
taatgatctg agaccagaac caaaaattat cctagtatct gtttcctgaa gagtatattc    39180
actgggcata aaaggaccaa ccgaaccttc tacagaagtc caagtcttta tttttaaggt    39240
aaatgctgag agtttaccat gtctctgtta actgagcttt gataagaaca tcctccagat    39300
caatgacttc attctctagg cattacatca tgctcacagg gacctatctg gctatgaagc    39360
tagaaggctg aaccttgaga atcacagcac tctcacccac catagaaagt ctgacagagt    39420
cttctcgggt agacatcctt aggaggaaat aatagagctg gccaaattaa ggtcttctct    39480
aagtcacctt gatttcttta aaataaatgt cgataataac tgccaaaata tacatatttg    39540
tggtgtgtgt gtgtgtgtgt gtgtgtgtct cacattgtgt gataataggg ttgagaccaa    39600
cagaaagatg tgttctgctt cccctggtcc tactttctat atatattttt atttataaag    39660
agattctatg agcaaagaat attagaatta gtggttatgg ataagtcttt gaaaaatatt    39720
ctgagtctgt tcctttctct gggacactta ggacagatga gttattgcaa ttatcctcat    39780
aacacactac gtagaagtcg catcttaaga ttgtatttct gaatattcaa gtgggagccc    39840
accatgaacc acagtaaata cgaacaaaga attagggaca gagagtaaag cacagcatta    39900
gagcatctgt caagcatctg agaagatctg ggttcaattc cctgtactac atgagtaatg    39960
tatacattat attcatgaat gaacaaaaaa gcaaacatct acatcttcaa atataaatta    40020
ttaaaacaaa ttattaaaaa cttgccattg aacatgacct ctttcggctg aatctcacta    40080
taaccacact aatttgttca agaaataact caaatgtttt attcgtagtt agccttgtgc    40140
tggaagagtg aatgagtaca cagaaggata atggctgtac cataggacaa tgtaactgtc    40200
agcttctttt tattggtaac tgttcctaaa tggtagtgcc ctttctcata aatcaagaaa    40260
gcagataaca tatttttgaa ggaaatacct gttctccagt agcagagtct gtgatacact    40320
atttctattc tttccagcaa agacaatgtt ggctctttct aaatattccc aatgcccaag    40380
atgacttatt tttgaaagct attgtttata taacctaaat tactatgatc aataaagcta    40440
agcaacacta atatatgtcc tcaataaaaa aaatcattga tataaaaata aaagtcatga    40500
caattgcaag atcccaactg ataatcaaat gtccaattag ctcttcattc tccctctgaa    40560
acctagattt tcaaggacca catgcacttc aaggcatggc ctctttggct tagagtaagt    40620
```

```
aagctatgag ttatgtatga gctgtaagtt gtaagcataa gtaagtcata tgccatgtat    40680
gagttgaata gatttcagat gaacaggaag tattgcttat cttcaaggga tttgtcaaat    40740
aattaaccat ttaaaataaa aattctcctc aattttccaa attatcttgg ttagaaatga    40800
tcaaattaaa tttcatttcc ctataataca gttataaacc gtatgtgatg atgctgttta    40860
ctgatggggg aagatggtgt gtccgactaa ttatgctata tgataatgga gttttaggat    40920
gagtcacttt ctatctaaag ctttcagttg ctttcatggt ggtcaaaggg gaaattggca    40980
attgtctaca aggagaaaat gtgataagtt cagaaagagg tgtttgtggt tgtcacttca    41040
attctcagga aagatgaagc tagcttaggt cctaagtttg ttttattact tcaaatgcct    41100
gctgagaatt ttttagggat ttgaaatata tataaatata catatacata cacacacaca    41160
cacacacaca cacacacaca cacacacaca catattctca gtaaagaaag acttagaaat    41220
cttgaattga ttttctttta atgtgggaga ctaattcact gaagaaacct gtaattcccc    41280
ttcagaagac tggtttcaac cgagatctca gaaatactat aaatatccca gagtttagaa    41340
tttgttataa aggcagttat agtggttatt tgatcaaaac agagtgcagc cacttcacga    41400
gccattcatc cctcagtcct gggccctgaa ggggaaagag actacagaga tggcatgagg    41460
atggactcag agacaagggt ggctccagag cagactttgt aggtttgagt agggcctcca    41520
attaacctgg ctattctact aagttccctt cattctgatg ggaaaaactg aagataaaat    41580
gagtactagc taatatgata aatgtgggtt atttcatggc agcataagaa atgaaatgtt    41640
gccaattatc gttttgaagc ataaagctcc tttaaaaaat atttcagggg ctggagagat    41700
ggctcagcgg tcaggaaaat tggctgctct tccagaggac ctgggttcat tccccagtac    41760
ccacatggca actcacaaat aactataact ccagttgcag agtatctgac accttcacac    41820
aaatatccat gcaggaaaaa caccaatgca catgaaataa agtaaatta ttttttaaaa    41880 agtatctcaa atatccaaac caacaaataa gacaagttta attgactgtt tatgtacaaa    41940
ggtaaagcag cccatataaa ctttctgaaa agtttaaaat caaaccaata cttctttcta    42000
ggtaaaaaat attgcaccta ctatgtattt gaatgttgct aaagtgaatg agatcaatag    42060
cttgccctca aattttagtg acaataaaag tccaatgtcc atttaatcaa gtggtcagca    42120
ctctttactg tgcctaggca tcacatagaa gggaggttaa acacaaatgg gggtttctgg    42180
ttcacagaaa ctaggcagtg gcccctaagc atgtttttaa aaaaatgttc aagtgatgct    42240
gagcttccat gatacatcat taaattgatt taataggtat aaacacactc aaaattcaga    42300
atatatggaa tatatgttcc aagtagcagc acctcctcat gtggtttat agctaacggc    42360 catttcagtt ggaaatactg tgcttgtgcc ttttctccat cgcgggagcc agaaatagtt    42420
acgcaaatat acagcagtaa caaacttaac ctacaatttc actccaagtg tatcttgcct    42480
ttttcgttta aaagttaaaa actgcatgta atagttacca agctgattaa ttcaatatta    42540
tctttaacag taaactcaat tcataaagaa acactgtctg ttacctaagt tctgttcacg    42600
gaaaccatga aggccgcttc acacaatcag cctggcactg tatacaactg ttttttccct    42660
aatgtaattt ggggaactaa taatttataa tgggatgatg gtgttgtttt acccacaaag    42720
acaataatca aacccagatt gcaaataatg aaattatgaa ctaggataaa acgagaagca    42780
gaaggcttac cctcccccca tgggagcaca tattttgaga tgatacaatt acttgtcaga    42840
cagtgacaca tcgtccactt tgagcatagt atgctttcag gtgaacagtc atctgcgaaa    42900
gcgagcctgc agcattctcc aggaacacat ttagaagaca tcctctcaac ttggatttat    42960
```

```
catttatgga aaatagccaa accaaccaac caaacaaaca aacaaacaaa caaaccccct   43020
ctactttaat gatactattt caagttttag aaaaaaaatt tataaaaaca aaaacccaca   43080
atatcttaaa ttgcttttta aaagacaact tctcagccac cttcgcctca atgttttcta   43140
cagaataaaa ggagaagtcc taaaaacaga cagactggag tctgcagagc tctgaatatt   43200
cacagaaggt aaacaatctt ctactggggg ctgttttcct cccctctctg cagacagaca   43260
cggagtctgc actgctctga gcctgcatgg aaggtgtgct ttcttccctt cttcctttct   43320
ctttctctag aacactcaag gctgccttgc tgaagtctct gcagagtctc tatcacagag   43380
ggctttggga acttatgcaa gtcactgaga agaaagcaac agatgccagt ctgcaagttc   43440
cactaactag tattcccgga cacactcata tccttcagat tcagcagaac caggtaatgt   43500
tgttatatta gcatttaaca gaaatctact tatattctga aaaaatatgt tatatacata   43560
tatatattat atacactcaa gtttgttctt gaaattgaaa gccttatata gcaattaata   43620
aaaccagaag catatgtttg gaatggcatt aagttaatta aaccaagata taagtctcag   43680
tggtgtggga gacgaaattc ttcaatgaaa atatgctaag catggagaaa tattgatgct   43740
ttgaccctaa aatgagaatt aaaaatagat gaaaggagtg gaaactccca aagtcaagaa   43800
cattgttaaa tgatttgcct actctacaca aggagcattc ttaaggtaga gtggtcagaa   43860
ctatccagga aatgagtaat taaaaggaac taacaattgc aaagaggttt gaactcagtg   43920
gtgaactcag tcactctgag gtgttggatg aggggctgag gactgagctc atacttctgg   43980
tattattctt aactgtatcg ttttcagtaa ttaaaggatc ccattgacat tagagggaag   44040
tatgtgctat cttcagttat cacgttaaat ctcccatgag agttttgtgg ggttttcaaa   44100
ctgtatattt gaatatgagg aatcccattt tatgaaaaat catttttattt atttgatgga   44160 aatttgaaaa gttttaaatt tcatcttaaa tttcaagtta gatacaagac agccaagtca   44220
actgctccta ttccttcccc cgtctgttgt gtgataatct aggatatcag ataaggatcc   44280
gattctgcta tttatttta gctaccatta aatatgccag gaatgatgct ctggctgcct   44340
tgagaaatat caagtaatga tcacagatag agaatctatt gcctgcatca tcattattac   44400
cattttagga ttcactctga atgatattca aaaacatata caaacttcaa atataatgaa   44460
tgagctgaaa atgagaaatg catgggctaa aagcactcta aatcatgagt ctctgtgagg   44520
ctaatatttt attgcatgac tgaacacagg caaagatatt tctcaatgca aggaaaatt   44580 ttttggatta ttattttcta ctatttacta tttaatatat gaattcattt cccagaagtg   44640
attttatacc aatctctttg aaattctcca tttatgattc caactcataa ttaatcactc   44700
ctctattgaa ttcatcaatg atactaaaga gtgaaaccag gaatatgggc agagaaggaa   44760
aggcagctgt aaacagacac aaaaggctac tcggccatgt aaaagaagat gcaggggaaa   44820
taggcaaagc atcactagag tgcctgtcat taggcttttc gaaattaaca cagggggtgct   44880 gacaccaaga ccacagtgtt gtaaaataca gccttcaacc aaaacaagca caaagctctc   44940 atgcacatctc acaacacacc acctcgtttt aagttgctag agatggaatt cttgtgtaga   45000
tgagatattc agggattcgg ttgtctattc acccctacta actgccacag taaagataaa   45060
aaaaactcaa gttttaagca acgctgtaat tctaaaatgt atgtatgaag ataacaacca   45120
aaccaatgac ctgtgatcac cctccctctc tctctttctt tctactacag gaccatggat   45180
gtgcctggtg tcaacaccac ctcagccaat accaccttct cccctgggac cagcaccctg   45240
tgcgtcagag actacaagat cacccaggtt ctcttcccat tgctgtacac cgtcctgttc   45300
tttgctgggc tcatcacgaa cagcttggca atgaggattt tctttcagat ccgcagtaaa   45360
```

-continued

```
tccaacttca tcattttcct taagaacacg gtcatctctg atctactaat gattctaact    45420
tttccattta aaattcttag tgatgctaaa ctgggagccg ggcctctgag aaccttggtg    45480
tgccaagtta cttcagtcac attttatttt acaatgtata tcagtatatc gttcctgggg    45540
ttgataacca ttgaccgcta cctgaagacc accaggccat ttaaaacgtc cagccccagc    45600
aatctcttgg gtgcaaagat tctttctgtt gtcatctggg ccttcatgtt cttaatttca    45660
ctgcctaaca tgattctcac caacaggagg ccaaaagata aggacgtaac aaaatgttct    45720
ttcttaaagt cagagtttgg tctagtttgg cacgaaatag tcaattacat ctgccaagtc    45780
attttctgga ttaatttttt aattgtcatc gtttgttata gcctcattac caaagaactc    45840
tatcggtctt atgtcagaac aagggggttca gccaaagttc ccaagaaaaa ggtaaacgtc    45900
aaggttttca tcatcattgc tgtattcttt atttgctttg ttcccttcca ctttgcacgg    45960
attccctaca ccctgagcca aactcgggcc gtctttgact gcagtgctga aacaccctg    46020 ttctacgtga aggagagcac cctatggctg acgtcactga acgcctgcct tgatccattc    46080
atctactttt ttctttgcaa gtctttcaga aattccttga caagcatgct gaggtgctca    46140
aactctacat caacatctgg gacaaacaag aagaaaggac aagaaggtgg cgaaccaagc    46200
gaagagaccc caatgtagaa cattacccaa ggggctgctt cagtctttaa tatccagact    46260
gctccaagga aatcaccata caaatatatt aacattcact aaaaagaagt tgagttaatg    46320
attctttaaa taatcaataa agtaagaaaa taattttt                            46358
```

<210> SEQ ID NO 2
<211> LENGTH: 347
<212> TYPE: PRT
<213> ORGANISM: Mus musculus

<400> SEQUENCE: 2

```
Met Asp Val Pro Gly Val Asn Thr Thr Ser Ala Asn Thr Thr Phe Ser
1               5                   10                  15

Pro Gly Thr Ser Thr Leu Cys Val Arg Asp Tyr Lys Ile Thr Gln Val
            20                  25                  30

Leu Phe Pro Leu Leu Tyr Thr Val Leu Phe Phe Ala Gly Leu Ile Thr
        35                  40                  45

Asn Ser Leu Ala Met Arg Ile Phe Phe Gln Ile Arg Ser Lys Ser Asn
    50                  55                  60

Phe Ile Ile Phe Leu Lys Asn Thr Val Ile Ser Asp Leu Leu Met Ile
65                  70                  75                  80

Leu Thr Phe Pro Phe Lys Ile Leu Ser Asp Ala Lys Leu Gly Ala Gly
                85                  90                  95

Pro Leu Arg Thr Leu Val Cys Gln Val Thr Ser Val Thr Phe Tyr Phe
            100                 105                 110

Thr Met Tyr Ile Ser Ile Ser Phe Leu Gly Leu Ile Thr Ile Asp Arg
        115                 120                 125

Tyr Leu Lys Thr Thr Arg Pro Phe Lys Thr Ser Ser Pro Ser Asn Leu
    130                 135                 140

Leu Gly Ala Lys Ile Leu Ser Val Val Ile Trp Ala Phe Met Phe Leu
145                 150                 155                 160

Ile Ser Leu Pro Asn Met Ile Leu Thr Asn Arg Arg Pro Lys Asp Lys
                165                 170                 175

Asp Val Thr Lys Cys Ser Phe Leu Lys Ser Glu Phe Gly Leu Val Trp
            180                 185                 190
```

```
His Glu Ile Val Asn Tyr Ile Cys Gln Val Ile Phe Trp Ile Asn Phe
        195                 200                 205
Leu Ile Val Ile Val Cys Tyr Ser Leu Ile Thr Lys Glu Leu Tyr Arg
        210                 215                 220
Ser Tyr Val Arg Thr Arg Gly Ser Ala Lys Val Pro Lys Lys Lys Val
225                 230                 235                 240
Asn Val Lys Val Phe Ile Ile Ala Val Phe Phe Ile Cys Phe Val
                245                 250                 255
Pro Phe His Phe Ala Arg Ile Pro Tyr Thr Leu Ser Gln Thr Arg Ala
                260                 265                 270
Val Phe Asp Cys Ser Ala Glu Asn Thr Leu Phe Tyr Val Lys Glu Ser
            275                 280                 285
Thr Leu Trp Leu Thr Ser Leu Asn Ala Cys Leu Asp Pro Phe Ile Tyr
        290                 295                 300
Phe Phe Leu Cys Lys Ser Phe Arg Asn Ser Leu Thr Ser Met Leu Arg
305                 310                 315                 320
Cys Ser Asn Ser Thr Ser Thr Ser Gly Thr Asn Lys Lys Lys Gly Gln
                325                 330                 335
Glu Gly Gly Glu Pro Ser Glu Glu Thr Pro Met
            340                 345

<210> SEQ ID NO 3
<211> LENGTH: 59
<212> TYPE: DNA
<213> ORGANISM: Mus musculus

<400> SEQUENCE: 3
gtcacacagc aggagctgcc gcacggacac tttcccgtat ccagggtcac agtgcaagg    59

<210> SEQ ID NO 4
<211> LENGTH: 133
<212> TYPE: DNA
<213> ORGANISM: Mus musculus

<400> SEQUENCE: 4
aggggtggca tctacctgct tggcaactca ccttcaccgg caccacccct gttttttccag   60 tttggaacat gctaaagtaa aataataacg tgctacccga cctgaagcac ttgatgtggg   120
cgtaccctac aga                                                      133

<210> SEQ ID NO 5
<211> LENGTH: 164
<212> TYPE: DNA
<213> ORGANISM: Mus musculus

<400> SEQUENCE: 5
aacactcaag gctgccttgc tgaagtctct gcagagtctc tatcacagag ggctttggga   60
acttatgcaa gtcactgaga agaaagcaac agatgccagt ctgcaagttc cactaactag   120
tattcccgga gacactcata tccttcagat tcagcagaac cagg                   164

<210> SEQ ID NO 6
<211> LENGTH: 1190
<212> TYPE: DNA
<213> ORGANISM: Mus musculus

<400> SEQUENCE: 6
caggaccatg gatgtgcctg gtgtcaacac cacctcagcc aataccacct ctcccctgg    60 gaccagcacc ctgtgcgtca gagactacaa gatcacccag ttctcttcc cattgctgta   120
```

-continued

```
caccgtcctg ttctttgctg ggctcatcac gaacagcttg gcaatgagga ttttctttca      180
gatccgcagt aaatccaact tcatcatttt tcttaagaac acggtcatct ctgatctact      240
aatgattcta acttttccat ttaaaattct tagtgatgct aaactgggag ccgggcctct      300
gagaaccttg gtgtgccaag ttacttcagt cacattttat tttacaatgt atatcagtat      360
atcgttcctg gggttgataa ccattgaccg ctacctgaag accaccaggc catttaaaac      420
gtccagcccc agcaatctct tgggtgcaaa gattctttct gttgtcatct gggccttcat      480
gttcttaatt tcactgccta acatgattct caccaacagg aggccaaaag ataaggacgt      540
aacaaaatgt tctttcttaa agtcagagtt tggtctagtt tggcacgaaa tagtcaatta      600
catctgccaa gtcattttct ggattaattt tttaattgtc atcgtttgtt atagcctcat      660
taccaaagaa ctctatcggt cttatgtcag acaaggggt tcagccaaag ttcccaagaa      720
aaaggtaaac gtcaaggttt tcatcatcat tgctgtattc tttatttgct ttgttccctt      780
ccactttgca cggattccct acaccctgag ccaaactcgg gccgtctttg actgcagtgc      840
tgagaacacc ctgttctacg tgaaggagag caccctatgg ctgacgtcac tgaacgcctg      900
ccttgatcca ttcatctact ttttctttgc aagtctttca gaaattcctt gacaagcatg      960
ctgaggtgct caaactctac atcaacatct gggacaaaca agaagaaagg acaagaaggt     1020
ggcgaaccaa gcgaagagac cccaatgtag aacattaccc aaggggctgc ttcagtcttt     1080
aatatccaga ctgctccaag gaaatcacca tacaaatata ttaacattca ctaaaaagaa     1140
gttgagttaa tgattcttta aataatcaat aaagtaagaa ataatttttt              1190
```

```
<210> SEQ ID NO 7
<211> LENGTH: 29
<212> TYPE: DNA
<213> ORGANISM: Mus musculus

<400> SEQUENCE: 7
aaggatccaa aatggatgtg cctggtgtc                                           29

<210> SEQ ID NO 8
<211> LENGTH: 28
<212> TYPE: DNA
<213> ORGANISM: Mus musculus

<400> SEQUENCE: 8
aactcgagct acattggggt ctcttcgc                                            28

<210> SEQ ID NO 9
<211> LENGTH: 24
<212> TYPE: DNA
<213> ORGANISM: Mus musculus

<400> SEQUENCE: 9
cagagactac aagatcaccc aggt                                                24

<210> SEQ ID NO 10
<211> LENGTH: 25
<212> TYPE: PRT
<213> ORGANISM: Mus musculus
```

```
-continued

<400> SEQUENCE: 10

Gly Ala Ala Gly Gly Cys Cys Cys Ala Gly Ala Thr Gly Ala Cys Ala
1               5                   10                  15

Ala Cys Ala Gly Ala Ala Ala Gly Ala
            20              25
```